US011340231B2

(12) United States Patent
Szewczak et al.

(10) Patent No.: US 11,340,231 B2
(45) Date of Patent: May 24, 2022

(54) METHODS OF SCREENING FOR CONDENSATE-ASSOCIATED SPECIFICITY AND USES THEREOF

(71) Applicant: Dewpoint Therapeutics, Inc., Boston, MA (US)

(72) Inventors: Alexander Szewczak, Needham, MA (US); Ina Poser, Dresden (DE); Mark Andrew Murcko, Holliston, MA (US); Stephen Paul Hale, Belmont, MA (US); Bruce Aaron Beutel, Needham, MA (US)

(73) Assignee: DEWPOINT THERAPEUTICS, INC., Boston, MA (US)

( * ) Notice: Subject to any disclaimer, the term of this patent is extended or adjusted under 35 U.S.C. 154(b) by 0 days.

(21) Appl. No.: 17/203,005

(22) Filed: Mar. 16, 2021

(65) Prior Publication Data

US 2021/0208153 A1 Jul. 8, 2021

Related U.S. Application Data

(63) Continuation of application No. PCT/US2020/051331, filed on Sep. 17, 2020.

(60) Provisional application No. 62/902,316, filed on Sep. 18, 2019.

(51) Int. Cl.
| | | |
|---|---|---|
| G01N 33/68 | (2006.01) | |
| G01N 33/50 | (2006.01) | |
| G01N 33/58 | (2006.01) | |
| G01N 33/60 | (2006.01) | |

(52) U.S. Cl.
CPC ......... *G01N 33/68* (2013.01); *G01N 33/5005* (2013.01); *G01N 33/582* (2013.01); *G01N 33/60* (2013.01); *G01N 2496/00* (2013.01)

(58) Field of Classification Search
CPC .. G01N 33/68; G01N 33/5005; G01N 33/582; G01N 33/60; G01N 2496/00; G01N 33/6896
See application file for complete search history.

(56) References Cited

U.S. PATENT DOCUMENTS

| | | |
|---|---|---|
| 2007/0054353 A1 | 3/2007 | White et al. |
| 2007/0178537 A1 | 8/2007 | Chiosis et al. |
| 2007/0214509 A1 | 9/2007 | Langston |
| 2009/0143433 A1 | 6/2009 | Hendrix |
| 2009/0298910 A1 | 12/2009 | Griffey |
| 2014/0121122 A1 | 5/2014 | Li |
| 2014/0242602 A1 | 8/2014 | Chiosis et al. |
| 2014/0287932 A1 | 9/2014 | Hnisz |
| 2016/0235731 A1 | 8/2016 | Bradner |
| 2016/0348180 A1 | 12/2016 | Al-murrani |
| 2017/0233762 A1 | 8/2017 | Zalatan |
| 2017/0355977 A1 | 12/2017 | Brangwynne |
| 2018/0009779 A1 | 1/2018 | Bradner |
| 2018/0133168 A1 | 5/2018 | Hong et al. |
| 2018/0251497 A1 | 9/2018 | Brangwynne |
| 2018/0313827 A1 | 11/2018 | Baldwin et al. |
| 2019/0127428 A1 | 5/2019 | Taylor |
| 2019/0352648 A1 | 11/2019 | Young |
| 2019/0382346 A1 | 12/2019 | Dalfo Capella |
| 2020/0150107 A1 | 5/2020 | Hyman et al. |
| 2020/0284801 A1* | 9/2020 | Beutel ............... G01N 33/6848 |

FOREIGN PATENT DOCUMENTS

| | | |
|---|---|---|
| ES | 2338392 A1 | 5/2010 |
| KR | 20150112415 A | 10/2015 |
| WO | 2002038734 A2 | 5/2002 |
| WO | 2005099745 A2 | 10/2005 |
| WO | 2007071060 A1 | 6/2007 |
| WO | 2011093782 A1 | 8/2011 |
| WO | 2011100374 A2 | 8/2011 |
| WO | 2012006551 A2 | 1/2012 |
| WO | 2012162249 A1 | 11/2012 |
| WO | 2012167086 A2 | 12/2012 |
| WO | 2014062686 A1 | 4/2014 |
| WO | 2014066848 A1 | 5/2014 |
| WO | 2014145975 A2 | 9/2014 |
| WO | 2017207460 A1 | 12/2017 |
| WO | 2018006074 A2 | 1/2018 |
| WO | 2018129544 A1 | 7/2018 |
| WO | 2018170794 A1 | 9/2018 |

(Continued)

OTHER PUBLICATIONS

Hu et al. ("Screening novel stress granule regulators from a natural compound library," Protein Cell 2017, vol. 8, No. 8, pp. 618-622, published Jul. 10, 2017, Supplementary Materials, pp. 1-9). (Year: 2017).*

International Search Report and Written Opinion of the International Searching Authority dated Nov. 26, 2020, for International Application No. PCT/US2020/051331, filed Sep. 17, 2020, 20 pages.

Adams, V.H. et al. (May 18, 2007). "Intrinsic Disorder and Autonomous Domain Function in the Multifunctional Nuclear Protein, MeCP2," Journal of Biological Chemistry 282(20):15057-15064.

Aguzzi, A. et al. (Jul. 2016). "Phase Separation: Linking Cellular Compartmentalization to Disease," Trends in Cell Biology 26(7):547-558.

Alberti, S. (2017). "The Wisdom of Crowds: Regulating Cell Function Through Condensed States of Living Matter," J. Cell Sci. 130(17):2789-2796.

(Continued)

*Primary Examiner* — Tracy Vivlemore
*Assistant Examiner* — Nam P Nguyen
(74) *Attorney, Agent, or Firm* — Morrison & Foerster LLP

(57) ABSTRACT

Methods of identifying a compound, such as a test compound, and applications thereof are provided. For example, methods of identifying a compound that preferentially affects, increases, or decreases a level of association of a macromolecule with one or more target condensates or methods of identifying a compound that preferentially causes a macromolecule to associate or disassociate with one or more target condensates are provided. Additionally, methods of designing and/or identifying and/or making a compound, or portion thereof, with a desired characteristic are provided.

26 Claims, 11 Drawing Sheets

(56) References Cited

FOREIGN PATENT DOCUMENTS

| | | | |
|---|---|---|---|
| WO | 2019032613 A1 | 2/2019 | |
| WO | 2019084362 A2 | 5/2019 | |
| WO | 2019109017 A1 | 6/2019 | |
| WO | 2019171068 A1 | 9/2019 | |
| WO | 2019183552 A2 | 9/2019 | |
| WO | 2020037234 A1 | 2/2020 | |
| WO | 2020078924 A1 | 4/2020 | |
| WO | 2020163795 A1 | 8/2020 | |
| WO | 2020232416 A1 | 11/2020 | |
| WO | 2021055642 A2 | 3/2021 | |
| WO | 2021055644 A1 | 3/2021 | |

OTHER PUBLICATIONS

Alberti, S. (Oct. 23, 2017). "Phase Separation in Biology," Curr Biol. 27(20):R1097-R1102.

Alberti, S. et al. (Nov. 2, 2018). "A User's Guide for Phase Separation Assays With Purified Proteins." Journal of Molecular Biology 430(23):4806-4820.

Ali, M. et al. (May 22, 2018). "High-Throughput Discovery of Functional Disordered Regions," Molecular Systems Biology 14(5):e8377, 2 pages.

Allshire, R.C. et al. (Apr. 2018, e-pub. Dec. 13, 2017). "Ten Principles of Heterochromatin Formation and Function," Nature Reviews Molecular Cell Biology 19(4):229-244, 39 pages.

Amir, R.E. et al. (Oct. 1999). "Rett Syndrome is Caused by Mutations in X-Linked MECP2, Encoding Methyl-CpG-Binding Protein 2," Nature Genetics, 23(2):185-188.

An, W.F. et al. (2009). "Introduction: Cell-Based Assays for High-Throughput Screening," Methods Mol Biol. 486:1-12.

Anderson, E.N. et al. (2018). "Traumatic Injury Induces Stress Granule Formation and Enhances Motor Dysfunctions in ALS/FTD Models," Hum. Mol. Genet. 27(8):1366-1381.

Ausio, J. et al. (Sep. 2014). "MeCP2: The Long Trip From a Chromatin Protein to Neurological Disorders," Trends in Molecular Medicine 20(9):487-498.

Babu, M.M. et al. (Oct. 15, 2016). "The Contribution of Intrinsically Disordered Regions to Protein Function, Cellular Complexity, and Human Disease," Biochemical Society Transactions 44(5):1185-1200.

Bailey, J.K. et al. (2017, Aug. 9, 2017). "Nucleic Acid Binding Proteins Affect the Subcellular Distribution of Phosphorothioate Antisense Oligonucleotides." Nucleic Acids Research 45(18):10649-10671.

Bajar, B.T. et al. (Sep. 2016). "A Guide To Fluorescent Protein FRET Pairs," Sensors 16(9):1488, 24 pages.

Banani S.F. et al. (Jul. 28, 2016, e-pub. Jun. 30, 2016). "Compositional Control of Phase-Separated Cellular Bodies," Cell 166(3):651-663.

Banani, S.F. et al. (2017, e-pub. Feb. 22, 2017). "Biomolecular Condensates: Organizers of Cellular Biochemistry," Nat Rev Mol Cell Biol 18(5):285-298, 14 pages.

Bannister, A.J. et al. (Mar. 1, 2017). "Selective Recognition of Methylated Lysine 9 on Histone H3 by the HP1 Chromo Domain," Nature 410(6824):120-124.

Baron, D.M. et al. (Aug. 31, 2013). "Amyotrophic Lateral Sclerosis-Linked FUS/TLS Alters Stress Granule Assembly and Dynamics," Molecular Neurodegeneration 8(1):30, 18 pages.

Basturea, G.N. et al. (Jul. 1, 2019). "Biological Condensates," Material Methods 9, 17 pages.

Berry, J. et al. (Sep. 22, 2015, e-pub. Sep. 8, 2015). "RNA Transcription Modulates Phase Transition-Driven Nuclear Body Assembly," Proc Natl Acad Sci USA 112(38):E5237-E5245.

Best, R.B. (Feb. 2017). "Computational and Theoretical Advances in Studies of Intrinsically Disordered Proteins," Current Opinion in Structural Biology 42:147-154.

Boeynaems, S. et al. (Jun. 2018, e-pub. Mar. 27, 2018). "Protein Phase Separation: A New Phase in Cell Biology," Trends in Cell Biology 28(6):420-435, 26 pages.

Boija, A. et al. (Dec. 13, 2018, e-pub. Nov. 15, 2018). "Transcription Factors Activate Genes through the Phase-Separation Capacity of Their Activation Domains," Cell 175(7):1842-1855.

Bojcsuk, D. et al. (Apr. 20, 2017; e-pub. Dec. 19, 2016). "Inducible super-enhancers are organized based on canonical signal-specific transcription factor binding elements," Nucleic Acids Res. 45(7): 3693-3706.

Borggrefe, T. et al. (2011). "Interactions Between Subunits of the Mediator Complex With Gene-Specific Transcription Factors," Semin. Cell Dev. Biol. 22(7):759-768.

Bouchard J.J. et al. (Oct. 4, 2018, e-pub Sep. 20, 2018). "Cancer Mutations of the Tumor Suppressor SPOP Disrupt the Formation of Active," Phase-Separated Compartments. Mol Cell 72(1):19-36, 43 pages.

Boulay, G. et al. (2017). "Cancer-Specific Retargeting of BAF Complexes by a Prion-like Domain," Cell 171(1):163-178, 36 pages.

Boyd, J.D. et al. (Jan. 2014). "A High-Content Screen Identifies Novel Compounds That Inhibit Stress-Induced TDP-43 Cellular Aggregation and Associated Cytotoxicity." J Biomol Screen 19(1):44-56, 18 pages.

Bradner, J.E. et al. (Feb. 9, 2017). "Transcriptional Addiction in Cancer," Cell 168(4):629-643.

Brangwynne C.P. et al. (2013). "Phase Transitions and Size Scaling of Membrane-Less Organelles," J Cell Biol. 203(6):875-881.

Brangwynne, C.P. et al. (Jun. 26, 2009). "Germline P Granules are Liquid Droplets That Localize By Controlled Dissolution/Condensation," Science 324:1729-1732.

Buckley D.L. et al. (2012). "Targeting the Von Hippel-Lindau E3 Ubiquitin Ligase Using Small Molecules to Disrupt the VHL/HIF-1 A Interaction," J Am Chem Soc. 134(10):4465-4468.

Burke, K.A. et al. (2015). "Residue-by-Residue View of in Vitro FUS Granules that Bind the C-Terminal Domain of RNA Polymerase II," Molecular Cell 60(2):231-241.

Carmony, K.C. et al. (2012). Chapter 44 in "PROTAC-Induced Proteolytic Targeting," Methods Mol Biol. 832, 11 pages.

Carpenter, A.E. et al. (Oct. 31, 2006). "Cellprofiler: Image Analysis Software for Identifying and Quantifying Cell Phenotypes," Genome Biology 7(10):R100, 11 pages.

Carroll J.S. et al. (Nov. 2006). "Genome-Wide Analysis of Estrogen Receptor Binding Sites," Nat Genet 38(11):1289-1297.

Che, D.L. et al. (Oct. 16, 2015). "The Dual Characteristics of Light-Induced Cryptochrome 2, Homo-oligomerization and Heterodimerization, for Optogenetic Manipulation in Mammalian Cells," ACS Synth Biol. 4 (10):1124-1135, 26 pages.

Chen Y. et al. (Apr. 2019). "Genome Organization Around Nuclear Speckles," Current Opinion in Genetics & Development 55:91-99.

Cheutin, T. et al. (Jan. 31, 2003). "Maintenance of Stable Heterochromatin Domains By Dynamic HP1 Binding," Science 299(5607)721-725.

Chiolo, I. et al. (Mar. 4, 2011). "Double-Strand Breaks in Heterochromatin Move Outside of A Dynamic HP1a Domain to Complete Recombinational Repair," Cell 144(5)732-744.

Cho W.K. et al. (2018). "Mediator and RNA Polymerase II Clusters Associate in Transcription-Dependent Condensates," Science 361(6400):412-415, 13 pages.

Cho, W.K. et al. (May 3, 2016). "RNA Polymerase II Cluster Dynamics Predict Mrna mRNA Output in Living Cells, RNA Polymerase II Cluster Dynamics Predict Mrna Output in Living Cells." Elife 5. pii: e13617, 31 pages.

Chong, S. et al. (2018). "Imaging Dynamic and Selective Low-Complexity Domain Interactions That Control Gene Transcription," Science 361(6400):eaar2555, 25 pages.

Cisse, I.I. et al. (Aug. 9, 2013). "Real-Time Dynamics of RNA Polymerase II Clustering in Live Human Cells," Science 341(6146):664-667.

Conway, E.L. (Jan. 1, 1998). "A Review of the Randomized Controlled Trials of Tacrine in the Treatment of Alzheimer's Disease: Methodologic Considerations," Clinical Neuropharmacol 21(1):8-17.

(56) References Cited

OTHER PUBLICATIONS

Conway, J.W. et al. (Feb. 7, 2005). "The Mammalian Mediator Complex," FEBS Lett. 579(4):904-908.

Cooper M.S. et al. (Feb. 1, 2010, e-pub Sep. 5, 2009). "Visualizing Green Oil in Live Algal Cells", Journal of Bioscience and Bioengineering 109(2):198-201.

Dolgin, E. (Mar. 15, 2018). "Cell Biology's New Phase," Nature 555(7696):300-302, posted Dec. 17, 2018 on bioRXIV,http://www.cbeslm.cpaneldev.princeton.edu/wp-content/uploads/2019/01/NaturePhase.pdf.

Duan, L. et al. (Sep. 2017). "Understanding CRY2 Interactions for Optical Control of Intracellular Signaling," Nature Communications 8(1):1-10547, 10 pages.

Dubik D. et al. (Dec. 15, 1987). "Stimulation of C-Myc Oncogene Expression Associated With Estrogen-Induced Proliferation of Human Breast Cancer Cells," Cancer Res 47(24):6517-6521.

Ebmeier, C.C. et al. (Aug. 1, 2017). "Human TFIIH Kinase CDK7 Regulates Transcription-Associated Chromatin Modifications," Cell Rep 20(5):1173-1186.

Fang, M.Y. et al. (Sep. 4, 2019). "Small-Molecule Modulation of TDP-43 Recruitment to Stress Granules Prevents Persistent TDP-43 Accumulation in ALS/FTD," Neuron 103(5):802-819.

Fanning, S.W. et al. (2016). "Estrogen Receptor Alpha Somatic Mutations Y537S and D538G Confer Breast Cancer Endocrine Resistance by Stabilizing the Activating Function-2 Binding Conformation," Elife 5:e12792, 25 pages.

Feric, M. et al. (2016). "Coexisting Liquid Phases Underlie Nucleolar Subcompartments," Cell 165(7):1686-1697.

Festenstein, R. et al. (Jan. 31, 2003). "Modulation of Heterochromatin Protein 1 Dynamics in Primary Mammalian Cells," Science 299(5607):719-721.

Fu, D. et al. (Jul. 2014). "Imaging the Intracellular Distribution of Tyrosine Kinase Inhibitors in Living Cells With Quantitative Hyperspectral Stimulated Raman Scattering," Nature Chemistry 6(7):614-622, 18 pages.

Fukaya, T. et al. (Jul. 14, 2016). "Enhancer Control of Transcriptional Bursting," Cell 166(2):358-368.

Galdeano, C. (Oct. 23, 2014). "Structure-Guided Design and Optimization of Small Molecules Targeting the Protein-Protein Interaction Between the Von Hippel-Lindau (VHL) E3 Ubiquitin Ligase and the Hypoxia Inducible Factor (HIF) Alpha Subunit With in Vitro Nanomolar Affinities," J. Med. Chem. 57(20):8657-8663.

Germain, P. et al. (Dec. 2006). "Overview of Nomenclature of Nuclear Receptors," Pharmacological Reviews 58(4):685-704.

Ghosh, R.P. et al. (May 25, 2010). "Unique Physical Properties and Interactions of the Domains of Methylated DNA Binding Protein 2 (MeCP2)," Biochemistry 49(20):4395-4410, 38 pages.

Gibson, B.A. et al. (Oct. 3, 2019). "Organization of Chromatin by Intrinsic and Regulated Phase Separation," Cell 179(2):470-484, 15 pages.

Grewal, S.I.S. et al. (Jan. 2007). "Heterochromatin Revisited," Nature Reviews Genetics 8(1):35-46.

Gu, B. et al. (Mar. 2, 2018, e-pub. Jan. 25, 2018). "Transcription-Coupled Changes in Nuclear Mobility of Mammalian Cis-Regulatory Elements," Science 359(6379):1050-1055, 15 pages.

Guo, W. et al. (Mar. 9, 2018). "Splicing Factor RBM20 Regulates Transcriptional Network of Titin Associated and Calcium Handling Genes in the Heart," Int J Biol Sci. 14(4): 369-380.

Guo, W. et al. (May 2012). "RBM20, A Gene for Hereditary Cardiomyopathy, Regulates Titin Splicing," Nat Med. 18(5):766-773, 20 pages.

Guo, Y.E. et al. (Mar. 9, 2018, e-pub. Aug. 7, 2019). "Pol II Phosphorylation Regulates A Switch Between Transcriptional and Splicing Condensates," Nature 572(7770):543-548, 41 pages.

Guy, J. et al. (2011, e-pub. Jun. 29, 2011). "The Role of MeCP2 in the Brain," Annual Review of Cell and Developmental Biology 27(1):631-652.

Hager, K. et al. (Jan. 1, 2007). "Alpha-Lipoic Acid as a New Treatment Option for Alzheimer's Disease—A 48 Months Follow-Up Analysis," Journal of Neural Transmission Suppl 72:189-193.

Hahn, S. et al. (Nov. 2011). "Transcriptional Regulation in *Saccharomyces Cerevisiae*: Transcription Factor Regulation and Function, Mechanisms of Initiation, and Roles of Activators and Coactivators," Genetics 189(3):705-736.

Han, T.W. et al. (May 11, 2012). "Cell-Free Formation of RNA Granules: Bound RNAs Identify Features and Components of Cellular Assemblies," Cell 149(4):768-779.

Harmon, T.S. et al. (Nov. 1, 2017). "Intrinsically Disordered Linkers Determine the Interplay Between Phase Separation and Gelation in Multivalent Proteins." Elife 6:e30294, 31 pages.

Hendrich, B. et al. (Nov. 1998). "Identification and Characterization of a Family of Mammalian Methyl-CpG Binding Proteins," Molecular and Cellular Biology 18(11):6538-6547.

Hnisz, D. et al. (Mar. 23, 2017). "A Phase Separation Model for Transcriptional Control," Cell 169(1):13-23, 23 pages.

Hnisz, D. et al. (Nov. 7, 2013, e-pub. Oct. 10, 2013). "Super-enhancers in the control of cell identity and disease," Cell 155(4):934-947.

Hu, L.D. et al. (Aug. 2017, e-pub Jul. 10, 2017) "Screening Novel Stress Granule Regulators From a Natural Compound Library," Protein & Cell 8(8):618-622.

Hyman, A.A. et al. (2014) "Liquid-Liquid Phase Separation in Biology," Annual Review of Cell and Developmental Biology 30:39-58.

Imbeault, M. et al. (Mar. 23, 2017). "KRAB Zinc-Finger Proteins Contribute to the Evolution of Gene Regulatory Networks," Nature 543(7646):550-554.

International Preliminary Report on Patentability, dated Sep. 29, 2020, for PCT Application No. PCT/US2019/023694, filed on Mar. 22, 2019, 11 pages.

International Search Report and Written Opinion of the International Searching Authority dated Jan. 27, 2020, for International Patent Application No. PCT/EP2019/077818, filed Oct. 14, 2019, 12 pages.

International Search Report and Written Opinion of the International Searching Authority dated Jul. 3, 2020, for International Application No. PCT/US2020/017333, filed Feb. 7, 2020, 10 pages.

International Search Report and Written Opinion of the International Searching Authority dated Jul. 29, 2020, for International Application No. PCT/US2020/033295, filed May 15, 2020, 17 pages.

International Search Report and Written Opinion of the International Searching Authority dated Sep. 23, 2019, for International Patent Application No. PCT/US2019/023694, filed Mar. 22, 2019, 11 pages.

Ip, J.P.K. et al. (Jun. 2018, e-pub. Mar. 6, 2019). "Rett Syndrome: Insights Into Genetic, Molecular and Circuit Mechanisms," Nature Reviews Neuroscience 19(6):368-382, 36 pages.

Janicki, S.M. et al. (Mar. 5, 2004). "From Silencing to Gene Expression: Real-Time Analysis in Single Cells," Cell 116(5):683-698.

Kang, Y. K. et al. (Mar. 5, 2002). "The TRAP/Mediator Coactivator Complex Interacts Directly With Estrogen Receptors Alpha and Beta Through the TRAP220 Subunit and Directly Enhances Estrogen Receptor Function in Vitro," Proc Natl Acad Sci U.S.A. 99(5):2642-2647.

Kato, M. et al. (May 11, 2012). "Cell-Free Formation of RNA Granules: Low Complexity Sequence Domains Form Dynamic Fibers Within Hydrogels." Cell 149(4):753-767.

Klein, I.A. et al. (Jun. 19, 2020). "Partitioning of Cancer Therapeutics in Nuclear Condensates," Science 368 (6497):1386-1392, 18 pages.

Kornberg, R.D. (May 2005). "Mediator and the Mechanism of Transcriptional Activation," Trends in Biochemical Sciences 30(5):235-239.

Kwon, I. et al. (Nov. 21, 2013). "Phosphorylation-Regulated Binding of RNA Polymerase II to Fibrous Polymers of Low-Complexity Domains," Cell 155(5):1049-1060.

Lachner, M. et al. (2001). "Methylation of Histone H3 Lysine 9 Creates a Binding Site for HP1 Proteins," Nature 410(6824):116-120.

Lambert, S.A. et al. (Feb. 8, 2018). "The Human Transcription Factors," Cell 172(4):650-665.

(56) References Cited

OTHER PUBLICATIONS

Lanni, E.J. et al. (Aug. 1, 2012, e-pub Aug. 30, 2013). "Mass Spectrometry Imaging and Profiling of Single Cells," Journal of Proteomics 75(16):5036-5051.
Larson, A.G. et al. (Jul. 13, 2017). "Liquid Droplet Formation by HP1α Suggests a Role for Phase Separation in Heterochromatin," Nature 547(7662):236-240, 29 pages.
Lei, J.T. et al. (Aug. 7, 2018). "Functional Annotation of ESR1 Gene Fusions in Estrogen Receptor-Positive Breast Cancer," Cell Rep 24(6):1434-1444.
Leroi, I. et al. (Oct. 25, 2006, e-pub. Jun. 27, 2006). "Non-Dopaminergic Treatment of Cognitive Impairment and Dementia in Parkinson's Disease: A Review," Journal of Neurological Sciences 248(1-2):104-114.
Lewis, J.D. et al. (Jun. 12, 1992). "Purification, Sequence, and Cellular Localization of a Novel Chromosomal Protein That Binds to Methylated DNA," Cell 69(6):905-914.
Li, P. et al. (Mar. 15, 2012). "Phase Transitions in the Assembly of Multivalent Signalling Proteins." Nature 483 (7389):336-340, 13 pages.
Li, S. et al. (2013, e-pub Jan. 9, 2013). "Rbm20 Regulates Titin Alternative Splicing as a Splicing Repressor," Nucleic Acids Research 41(4):2659-2672.
Li, X-H. et al. (May 1, 2018, e-pub. Feb. 12, 2018). "Function and Regulation of Phase-Separated Biological Condensates," Biochemistry 57(17):2452-2461.
Lin, Y. et al. (Oct. 15, 2015). "Formation and Maturation of Phase-Separated Liquid Droplets by RNA-Binding Proteins," Mol. Cell 60(2):208-219.
Lin, Y. et al. (Oct. 20, 2016)."Toxic PR Poly-Dipeptides Encoded by the C9orf72 Repeat Expansion Target LC Domain Polymers," Cell 167(3):789-802.
Liss, M. et al. (Jun. 11, 2018). "Drug Discovery With an RBM20 Dependent Titin Splice Reporter Identifies Cardenolides as Lead Structures to Improve Cardiac Filling," PLoS One 13(6): e0198492, 1-19.
Loven, J. et al. (Apr. 11, 2013). "Selective Inhibition of Tumor Oncogenes by Disruption of Super-Enhancers," Cell 153(2):320-334, 27 pages.
Lyst, M.J. et al. (May 2013). "Rett Syndrome: A Complex Disorder With Simple Roots. Nature Reviews Genetics," 16(5):261-274.
Macarron, R. et al. (2009, e-pub Jun. 5, 2009). "Design and Implementation of High-Throughput Screening Assays," in High Throughput Screening, Janzen W., Bernasconi P. (eds) Humana Press: Totowa, NJ, vol. 565, 1-32., 12 pages (Abstract only).
Mackenzie, I.R. et al. (Aug. 16, 2017): "TIAI Mutations in Amyotrophic Lateral Sclerosis and Frontotemporal Dementia Promote Phase Separation and Alter Stress Granule Dynamics," Neuron 95(4):808-816.
Maharana, S. et al. (May 25, 2018, e-pub. Apr. 12, 2018). "RNA Buffers the Phase Separation Behavior of Prion-Like RNA-Binding Proteins," Science 360(6391):918-921.
Malik, S. et al. (Oct. 13, 2010). "The Metazoan Mediator Co-Activator Complex as an Integrative Hub for Transcriptional Regulation," Nature Reviews Genetics 11(11) 761-772, 23 pages.
Mangelsdorf, I. et al. (Jan. 1, 2017, e-pub Jun. 12, 2017). "Healing of Amyotrophic Lateral Sclerosis: A Case Report," Complementary Medicine Research 24(3):175-181.
Mansour, M.R. et al. (Dec. 12, 2014, e-pub Jan. 20, 2016). "An Oncogenic Super-Enhancer Formed Through Somatic Mutation of a Noncoding Intergenic Element," Science 346(6215):1373-1377, 11 pages.
Mateju, D.E. et al. (Jun. 14, 2017). "An Aberrant Phase Transition of Stress Granules Triggered by Misfolded Protein and Prevented by Chaperone Function", The EMBO Journal 36(12):1669-1687.
Meehan, R.R. et al. (1992). "Characterization of Mecp2, a Vertebrate DNA-Binding Protein With Affinity for Methylated DNA," Nucleic Acids Research 20(19):5085-5092.

Mitchell, P.J. et al. (Jul. 28, 1989). "Transcriptional Regulation in Mammalian Cells by Sequence-Specific DNA Binding Proteins," Science 245(4916):371-378.
Mitrea, D.M. et al. (Feb. 26, 2018). "Self-Interaction of Npm1 Modulates Multiple Mechanisms of Liquid-Liquid Phase Separation," Nature Communications 9(1):1-13.
Muiznieks, L.D. et al. (Nov. 2, 2018). "Role of Liquid-Liquid Phase Separation in Assembly of Elastin and Other Extracellular Matrix Proteins," Journal of Molecular Biology 430(23):4741-4753.
Nabet, B, et al. (May 2018, e-pub Dec. 17, 2018). "The Dtag System for Immediate and Target-Specific Protein Degradation," Nature Chemical Biology 14(5):431-441, 31 pages.
Nagalingam A. et al. (Apr. 2012, e-pub Feb. 16, 2012). "Med1 Plays a Critical Role in the Development of Tamoxifen Resistance," Carcinogenesis 33(4):918-930.
Nakano, M. et al. (Apr. 15, 2008). "Inactivation of a Human Kinetochore by Specific Targeting of Chromatin Modifiers," Developmental Cell, 14(4):507-522.
Nan, X. et al. (1993). "Dissection of the Methyl-Cpg Binding Domain From the Chromosomal Protein Mecp2," Nucleic Acids Research 21(21):4886-4892.
Naumann, M. et al. (Jan. 23, 2018). "Impaired DNA Damage Response Signaling by FUS-NLS Mutations Leads to Neurodegeneration and FUS Aggregate Formation," Nature Communications 9(1):1-17.
Nesbit C.E. et al. (May 13, 1999). "MYC Oncogenes and Human Neoplastic Disease," Oncogene 18(19):3004-3016.
Nott, T.J. et al. (Mar. 5, 2015). "Phase Transition of a Disordered Nuage Protein Generates Environmentally Responsive Membraneless Organelles," Mol. Cell 57(5):936-947.
Oates, M.E. et al. (2013, e-pub. Nov. 29, 2012). "$D^2P^2$: Database of Disordered Protein Predictions," Nucleic Acids Res. 41(D1):D508-D516.
Osborne, C.K. et al. (Feb. 11, 2011). "Mechanisms of Endocrine Resistance in Breast Cancer," Annu Rev Med 62:233-247, 17 pages.
Ozers, M.S. et al. (Jan. 1, 2005). "Analysis of Ligand-Dependent Recruitment of Coactivator Peptides to Estrogen Receptor Using Fluorescence Polarization," Mol Endocrinol 19(1):25-34.
Patel, A. et al. (Aug. 27, 2015). "A Liquid-to-Solid Phase Transition of the ALS Protein Accelerated by Disease Mutation" Cell 162:1066-1077.
Patel, A. et al. (May 19, 2017). "ATP as a Biological Hydrotrope," Science 356(6339):753-756.
Patel, B.P. et al. (Dec. 1, 2009). "Nutritional and Exercise-Based Interventions in the Treatment of Amyotrophic Lateral Sclerosis," Clinical Nutrition 28(6):604-617.
Pessina, F. et al. (Oct. 2019). "Functional Transcription Promoters at DNA Double-Strand Breaks Mediate RNA-Driven Phase Separation of Damage-Response Factors," Nature Cell Biology 21(10):1286-1299, 29 pages.
Plys, A.J. et al. (Jul. 1, 2019). "Phase Separation of Polycomb-Repressive Complex 1 is Governed by a Charged Disordered Region of CBX2." Genes & Development 33(13-14):799-813.
Posey, A.E. et al. (Mar. 9, 2018, e-pub. Jan. 22, 2018). "Profilin Reduces Aggregation and Phase Separation of Huntingtin N-Terminal Fragments by Preferentially Binding to Soluble Monomers and Oligomers," Journal of Biological Chemistry 293(10):3734-3746.
Potenza, E. et al. (2015, e-pub. Oct. 31, 2014). "MobiDB 2.0: An Improved Database of Intrinsically Disordered and Mobile Proteins," Nucleic Acids Res. 43(D1):D315-D320.
Rahman, S. et al. (Jun. 15, 2017). "Activation of the LMO2 Oncogene Through a Somatically Acquired Neomorphic Promoter in T-Cell Acute Lymphoblastic Leukemia," Blood 129(24):3221-3226, 5 pages.
Robb, C.M. et al. (Jul. 4, 2017). "Chemically Induced Degradation of CDK9 by a Proteolysis Targeting Chimera (PROTAC)," Chem Commun (Camb). 53(54)7577-7580, 12 pages.
Roberts, S.G.E. (Aug. 2000). "Mechanisms of Action of Transcription Activation and Repression Domains," Cell. Mol. Life Sci. 57(8-9):1149-1160.

(56) References Cited

OTHER PUBLICATIONS

Roe J. S. et al. (Aug. 24, 2017). "Enhancer Reprogramming Promotes Pancreatic Cancer Metastasis," Cell 170 (5):875-888, e820, 35 pages.
Sabari, B.R. et al. (Jul. 27, 2018, e-pub Jun. 21, 2018). "Coactivator Condensation at Super-Enhancers Links Phase Separation and Gene Control," Science, 361(6400): eaar3958, 1-24.
Saha, S. et al. (Sep. 8, 2016, e-pub. Sep. 1, 2016). "Polar Positioning of Phase-Separated Liquid Compartments in Cells Regulated by an Mrna Competition Mechanism," 166(6):1572-1584.
Sakamoto, K.M. et al. (Jul. 17, 2001). "Protacs: Chimeric Molecules That Target Proteins to the Skp1-Cullin-F Box Complex for Ubiquitination and Degradation," Proceedings of the National Academy of Sciences 98 (15):8554-8559.
Sever, R. et al. (Mar. 1, 2013). "Signaling by Nuclear Receptors," Cold Harbor Perspectives in Biology 5(3):1-4.
Shang, Y. et al. (Dec. 8, 2000). "Cofactor Dynamics and Sufficiency in Estrogen Receptor-Regulated Transcription," Cell 103(6):843-852.
Shin, Y. et al. (Sep. 22, 2017). "Liquid Phase Condensation in Cell Physiology and Disease," Science 357 (6357):eaaf4382, 13 pages.
Shrinivas, K. et al. (Dec. 17, 2018). "Enhancer Features That Drive Formation of Transcriptional Condensates," Molecular Cell 75(3):549-561, 28 pages.
Sigler, P.B. (May 19, 1988). "Acid Blobs and Negative Noodles," Nature 333(6170):210-212.
Skene, P.J. et al. (Feb. 26, 2010). "Neuronal MeCP2 is Expressed at Near Histone-Octamer Levels and Globally Alters the Chromatin State," Molecular Cell 37(4):457-468.
Smith, R. et al. (2016). "Raman Spectroscopy: An Evolving Technique for Live Cell Studies," Analyst 141 (12):3590-3600.
Soufi, A. et al. (Nov. 21, 2012). "Facilitators and Impediments of the Pluripotency Reprogramming Factors' Initial Engagement With the Genome," Cell 151(5):994-1004.
Staby, L. et al. (Aug. 2017). "Eukaryotic Transcription Factors: Paradigms of Protein Intrinsic Disorder," Biochem. J. 474(15):2509-2532.
Strom, A.R. et al. (Jul. 13, 2017). "Phase Separation Drives Heterochromatin Domain Formation," Nature 547 (7662):241-245, 19 pages.
Tate, P. et al. (Feb. 1996). "The Methyl-Cpg Binding Protein Mecp2 is Essential for Embryonic Development in the Mouse," Nat Genet 12(2):205-208.
Triezenberg, S.J. (Apr. 1995). "Structure and Function of Transcriptional Activation Domains," Curr. Opin. Genet. Dev. 5(2):190-196.
Tsai, A. et al. (Nov. 2, 2017). "Nuclear Microenvironments Modulate Transcription From Low-Affinity Enhancers," Elife 6:e28975, 18 pages.
Tuttle, L.M. et al. (Mar. 20, 2018). "Gcn4-Mediator Specificity is Mediated by a Large and Dynamic Fuzzy Protein-Protein Complex," Cell Rep. 22(12):3251-3264.
U.S. Appl. No. 17/040,967, filed Mar. 22, 2019, for Young et al.(U.S. Patent Application is not submitted herewith pursuant to the waiver of 37 C.F.R. § 1.98(a)(2)(iii) issued by the Office on Sep. 21, 2004.).
Van Esch, H. et al. (Sep. 2005). "Duplication of the MECP2 Region is a Frequent Cause of Severe Mental Retardation and Progressive Neurological Symptoms in Males," The American Journal of Human Genetics 77(3):442-453.
Wakefield, R.I.D. et al. (Sep. 3, 1999). "The Solution Structure of the Domain From Mecp2 That Binds to Methylated DNA," Journal of Molecular Biology 291(5):1055-1065.
Waks A.G. et al. (Jan. 22, 2019). "Breast Cancer Treatment: A Review," JAMA 321(3):288-300.
Wang Y. et al. (Sep. 24, 2015). "CDK7-Dependent Transcriptional Addiction in Triple-Negative Breast Cancer," Cell 163(1):174-186.
Wang, J. et al. (May 2016). "New Insights into the Regulation of Heterochromatin," Trends in Genetics 32(5):284-294, 19 pages.
Wang, T. et al. (2018, e-pub. May 26, 2018). "α-Lipoic Acid Attenuates Oxidative Stress and Neurotoxicity Via the ERK/Akt-Dependent Pathway in the Mutant hSOD1 Related *Drosophila* Model and the NSC34 Cell Line of Amyotrophic Lateral Sclerosis," Brain Research Bulletin 140(26):299-310.
Wegmann, S. et al. (Apr. 3, 2018, e-pub. Feb. 22, 2018). "Tau Protein Liquid-Liquid Phase Separation Can Initiate Tau Aggregation," The EMBO Journal 37(7):e98049, 21 pages.
Wheeler R.J. et al. (Dec. 15, 2017). "M128: Small Molecules for Modulating Protein Driven Liquid-Liquid Phase Separation in Neurodegenerative Disease," Molecular Biology of the Cell; Annual Joint Meeting of American Society for Cell Biology/European Molecular Biology Organization (ASCB/EMBO), American Society for Cell Biology Philadelphia, PA, 28(26):M128, 2 pages (Abstract only).
Wheeler, R.J. et al. (Aug. 21, 2019) "Small Molecules for Modulating Protein Driven Liquid-Liquid Phase Separation in Treating Neurodegenerative Disease," BioRxiv 721001, 48 pages.
Wheeler, R.J. et al. (May 26, 2018). "Controlling Compartmentalization by Non-Membrane-Bound Organelles," Philosophical Transactions of the Royal Society B: Biological Sciences 373(1747):20170193, 9 pages.
Winter, G.E. et al. (Jun. 19, 2015). "Selective Target Protein Degradation via Phthalimide Conjugation," Science 348 (6241):1376-1381, 13 pages.
Zamudio, A.V. et al. (Dec. 5, 2015). "Mediator Condensates Localize Signaling Factors to Key Cell Identity Gene," Mol Cell 76(5):753-766.
Zhang, P. et al. (Jun. 18, 2018). "Optogranules Reveal the Evolution of Stress Granules to ALS-FTD Pathology," bioRxiv 348870, 35 pages, as retrieved from https://www.biorxiv.org/content/biorxiv/early/2018/06/18/348870.full.pdf.
Andreassen, O.A. (Apr. 2001). "Effects of an Inhibitor of Poly(ADP-Ribose) Polymerase, Desmethylselegiline, Trientine, and Lipoic Acid in Transgenic ALS Mice," Exp Neurol. 168(2):419-424.
Gill, S.J. et al. (Jun. 25, 1980). "Ligand-Linked Phase Equilibria of Sickle Cell Hemoglobin," J Mol Biol. 140 (2):299-312.
International Preliminary Report on Patentability dated Aug. 10, 2021 for Patent Application No. PCT/US2020/017333, filed Feb. 7, 2020, 7 pages.
Li, C.H. et al. (Oct. 2020, e-pub. Jul. 22, 2020). "Mecp2 Links Heterochromatin Condensates and Neurodevelopmental Disease," Nature 586(7829):440-444, 40 pages.
Martin, E.W. et al. (Feb. 7, 2020). "Valence and Patterning of Aromatic Residues Determine the Phase Behavior of Prion-Like Domains," Science 367(6478):694-699, 16 pages.
Riback, J.A. et al. (2020, e-pub May 6, 2020). "Composition-Dependent Thermodynamics of Intracellular Phase Separation," Nature 581(7807):209-214, 21 pages.
Riback, J.A. et al. (Oct. 22, 2019). "Composition Dependent Phase Separation Underlies Directional Flux Through the Nucleolus," bioRxiv 809210:26 pages.
Tisel, W.A. et al. (Oct. 10, 1980). "Polyphasic Linkage Between Protein Solubility and Ligand Binding in the Hemoglobin-Polyethylene Glycol System," J Biol Chem 255(19):8975-8978.
Vuignier, K. et al. (Sep. 2010). "Drug-Protein Binding: A Critical Review of Analytical Tools," Anal Bioanal Chem. 398(1):53-66.
Guo, W. et al. (Feb. 10, 2018). "RBM20, A Potential Target for Treatment of Cardiomyopathy via Titin Isoform Switching," Biophysical Reviews 10(1):15-25.
Handoko, L. et al. (Apr. 3, 2018). "JQ1 Affects BRD2-Dependent and Independent Transcription Regulation Without Disrupting H4-Hyperacetylated Chromatin States," Epigenetics 13(4):410-431.
International Preliminary Report on Patentability dated Apr. 14, 2021 for Patent Application No. PCT/EP2019/077818, filed Oct. 14, 2019, 8 pages.
International Preliminary Report on Patentability dated Aug. 25, 2021 for Patent Application No. PCT/US2020/015329, filed Jan. 28, 2020, 6 pages.
International Search Report and Written Opinion of the International Searching Authority dated Apr. 2, 2020, for International Application No. PCT/US2020/015329, filed Jan. 28, 2020, 9 pages.
Lee, T.H. et al. (2017, e-pub. Jul. 17, 2017). "Molecular Mechanism of PD-1/PD-L1 Blockade via Anti-PD-L1 Antibodies Atezolizumb and Durvalumab," Scientific Reports 7(1):1-12.

(56) References Cited

OTHER PUBLICATIONS

Murayama, R. et al. (2018, e-pub Jun. 12, 2018). "Phosphorylation of the RSRSP Stretch is Critical for Splicing Regulation by RNA-Binding Motif Protein 20 (RBM20) Through Nuclear Localization," Scientific Reports 8(1):1-14.
Schneider, J.W. et al. (Nov. 2020, e-pub. Nov. 13, 2020). "Dysregulated Ribonucleoprotein Granules Promote Cardiomyopathy in RBM20 Gene-Edited Pigs," Nature Medicine 26(11):1788-1800, 2 pages. (Abstract Only).
White, M. R. et al. (May 16, 2019). "C9orf72 Poly (PR) Dipeptide Repeats Disturb Biomolecular Phase Separation and Disrupt Nucleolar Function," Molecular Cell 74(4):713-728.
Zhu, C. et al. (Feb. 1, 2015, e-pub Jan. 8, 2015). "RBM20 is an Essential Factor for Thyroid Hormone-Regulated Titin Isoform Transition," Journal of Molecular Cell Biology 7(1):88-90.

\* cited by examiner

METHODS OF SCREENING FOR CONDENSATE-ASSOCIATED SPECIFICITY AND USES THEREOF

CROSS-REFERENCE TO RELATED APPLICATIONS

This application is a continuation application of International Application No. PCT/US2020/051331, filed on Sep. 17, 2020, which claims the priority benefit of U.S. Provisional Application No. 62/902,316, filed on Sep. 18, 2019, the contents of each of which are incorporated herein by reference in their entirety.

FIELD OF THE INVENTION

The present invention relates to the field of biological condensates.

BACKGROUND

Cells contain membrane-bound organelles such as mitochondria, lysosomes, and the endoplasmic reticulum, to, in part, localize various cellular functions. In addition to membrane-bound organelles, cells contain distinct sub-compartments that do not comprise a membrane between them and their immediate surrounding solution. Numerous of these membrane-less molecular assemblies have been shown to be formed through a process termed liquid-liquid phase separation or condensation, in a manner analogous to the partitioning of oil droplets in water. During this process, e.g., a solution comprising biological macromolecules separates into different phases, namely, a condensate dense phase that is enriched in at least some of the biological macromolecules and a surrounding light phase. A number of cellular condensates have been recognized that play important roles in biology (Banani et al., 2017, *Nat Rev Mol Cell Biol*, 18:285-298).

Various condensates are known to be important for modulating specific cellular processes in different cell types. Mechanistically, for example, a condensate can bring together molecules at an elevated concentration to accelerate reactions inside the condensate, or can sequester molecules in the condensate thereby reducing their concentration and preventing their activity in the surrounding medium. Aberrant condensate function has also been implicated in various human diseases, such as neurodegenerative, proliferative, immunological, cardiac, or metabolic disease (Naumann et al., 2018, *Nat Commun*, 9(1):335; Wegmann et al., 2018, *EMBO J*, 37(7): e98049; and Aguzzi et al., 2016, 26(7): 547-558). However, there is a lack of understanding of the mechanisms governing partitioning of a single macromolecule into or out of a condensate, and there is little or nothing known regarding whether a compound can selectively alter the partitioning of a single macromolecule into or out of a condensate.

All references cited herein, including patent applications and publications, are incorporated by reference in their entirety.

BRIEF SUMMARY

Provided herein are methods of identifying a compound that preferentially affects a level of association of a first macromolecule with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially affects the level of association of the first macromolecule with the one or more target condensates if the compound alters the level of the first macromolecule as compared to a first reference level more than the compound alters the level of each additional macromolecule as compared to a reference level for each additional macromolecule. In some embodiments, the compound does not measurably alter the level of each additional macromolecule compared to the reference level for each additional macromolecule.

Also provided herein are methods of identifying a compound that preferentially increases a level of association of a first macromolecule with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially increases the level of association of the first macromolecule with the one or more target condensates if the compound increases the level of the first macromolecule as compared to a first reference level more than the compound increases the level of each additional macromolecule as compared to a reference level for each additional macromolecule. In some embodiments, the compound does not measurably increase the level of each additional macromolecule compared to the reference level for each additional macromolecule.

Also provided herein are methods of identifying a compound that preferentially decreases a level of association with one or more target condensates of a first macromolecule, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially decreases the level of association of the first macromolecule with the one or more target condensates if the compound alters the level of the first macromolecule as compared to a first reference level more than the compound decreases the level of each additional macromolecule as compared to a reference level for each additional macromolecule. In some embodiments, the compound does not measurably decrease the level of each additional macromolecule compared to the reference level for each additional macromolecule.

In some embodiments, the first reference level is a level of association of the first macromolecule with one or more reference condensates determined in the absence of the compound. In some embodiments, the reference level for each additional macromolecule is a level of association for each additional macromolecule with one or more reference condensates determined in the absence of the compound.

Also provided herein are methods of identifying a compound that preferentially causes a first macromolecule to associate with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining if a first macromolecule and at least one additional macromolecule are associated with the one or more target condensates, wherein the compound preferentially causes the first macromolecule to associate with the one or more target condensates if: (1) the compound causes the first macromolecule to associate with the one or more target condensates; (2) the compound does not cause each additional macromolecule to associate with the one or more target condensates; and (3) the first macromolecule would not be associated with the one or more target condensates in the absence of the compound.

In some embodiments, the compound preferentially causes the first macromolecule to associate with the one or more target condensates if (4) one or more of the at least one additional macromolecule would not be associated with the one or more target condensates in the absence of the compound. In some embodiments, the compound preferentially causes the first macromolecule to associate with the one or more target condensates if (4) each of the at least one additional macromolecule would not be associated with the one or more target condensates in the absence of the compound.

Also provided herein are methods of identifying a compound that preferentially causes a first macromolecule to disassociate with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining if a first macromolecule and at least one additional macromolecule are associated with the one or more target condensates, wherein the compound preferentially causes the first macromolecule to disassociate with the one or more target condensates if: (1) the compound causes the first macromolecule not to associate with the one or more target condensates; (2) the compound does not cause each additional macromolecule not to associate with the one or more target condensates; and (3) the first macromolecule would be associated with the one or more target condensates in the absence of the compound.

In some embodiments, the compound preferentially causes the first macromolecule to associate with the one or more target condensates if (4) one or more of the at least one additional macromolecule would be associated with the one or more target condensates in the absence of the compound. In some embodiments, the compound preferentially causes the first macromolecule to associate with the one or more target condensates if (4) each of the at least one additional macromolecule would be associated with the one or more target condensates in the absence of the compound.

In some embodiments, step (a) comprises contacting a cellular composition with a compound, wherein the cellular composition comprises the one or more target condensates, and the method further comprises causing the formation of the one or more target condensates prior to step (a). In some embodiments, step (a) comprises contacting a cellular composition with a compound, wherein the one or more target condensates form after contacting the cellular composition with the compound, and the method further comprises causing the formation of the one or more target condensates.

In some embodiments, the at least one additional macromolecule is 2 or more, 3 or more, 4 or more, or 5 or more macromolecules. In some embodiments, the at least one additional macromolecule is 1-10 macromolecules.

In some embodiments, the first macromolecule is aberrantly expressed in a disease state. In some embodiments, a disease state level of association of the first macromolecule with the one or more target condensates is altered compared to a normal state level of association of the first macromolecule with the one or more target condensates. In some embodiments, one or more of the at least one additional macromolecule is aberrantly expressed in a disease state.

In some embodiments, the first macromolecule is DNA or RNA. In some embodiments, the first macromolecule is a protein. In some embodiments, the first macromolecule comprises a mutation that alters the level of association of the first macromolecule with the one or more target condensates compared to a related protein that does not comprise the mutation. In some embodiments, the first macromolecule is FUS or eIF3.

In some embodiments, one or more of the at least one additional macromolecule is DNA or RNA. In some embodiments, one or more of the at least one additional macromolecule is a protein. In some embodiments, one or more of the at least one additional macromolecule comprise a mutation that alters its corresponding level of association with the one or more target condensates compared to a related protein that does not comprise the mutation. In some embodiments, one or more of the at least one additional macromolecule is FUS, eIF3, G3BP1, FUS and G3BP1, or eIF3 and G3BP1.

In some embodiments, the first macromolecule and/or one or more of the at least one additional macromolecule is a fusion protein. In some embodiments, the first macromolecule and/or one or more of the at least one additional macromolecule comprises a label. In some embodiments, the method further comprises labeling the first macromolecule and/or one or more of the at least one additional macromolecule. In some embodiments, the labeling comprises contacting the cellular composition with an antibody or antigen-binding fragment thereof comprising a label. In some embodiments, the label is a radioactive label, a colorimetric label, or a fluorescent label.

In some embodiments, the cellular composition comprises a microorganism or an animal cell. In some embodiments, the cellular composition comprises an animal cell. In some embodiments, the animal cell that has one or more features of a neurodegenerative, proliferative, immunological, cardiac, or metabolic disease. In some embodiments, the animal cell is a HeLa cell, a HEK293 cell, an induced pluripotent stem cell (iPSC cell), a cardiomyocyte, a myocyte, a stem cell-derived cell, a neuron, a cancer cell, an immune cell, or an adipocyte.

In some embodiments, the one or more target condensates is a cellular condensate. In some embodiments, the one or more target condensates is a nuclear condensate or a cytoplasmic condensate. In some embodiments, the cellular condensate is a cleavage body, a p-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

In some embodiments, the one or more target condensates is a single target condensate. In some embodiments, the compound does not measurably alter one or more of: size of the target condensate, location of the target condensate, surface area of the target condensate, and dissolution of the target condensate.

In some embodiments, the one or more target condensates is a plurality of target condensates. In some embodiments, the compound does not measurably alter one or more of: total number of the plurality of target condensates; size of the plurality of target condensates, location of the plurality of target condensates, surface area of the plurality of target condensates, and dissolution of the plurality of target condensates.

In some embodiments, the one or more target condensates is a plurality of target condensates. In some embodiments, the plurality of target condensates is all or a subset of a class of condensates in a portion of the cellular composition. In some embodiments, the plurality of target condensates is all or a subset of a class of condensates in a cell in the cellular composition. In some embodiments, the plurality of target condensates is all or a subset of a class of condensates in a portion of a cell in the cellular composition. In some embodiments, the portion of the cell is the cytoplasm, the nucleus, or an organelle.

In some embodiments, the class of condensates comprises condensates which comprise a specific macromolecule. In some embodiments, the class of condensates comprises condensates which are cleavage bodies; wherein the class of condensates comprises condensates which are p-granules; wherein the class of condensates comprises condensates which are histone locus bodies; wherein the class of condensates comprises condensates which are multivesicular bodies; wherein the class of condensates comprises condensates which are neuronal RNA granules; wherein the class of condensates comprises condensates which are nuclear gems; wherein the class of condensates comprises condensates which are nuclear pores; wherein the class of condensates comprises condensates which are nuclear speckles; wherein the class of condensates comprises condensates which are nuclear stress bodies; wherein the class of condensates comprises condensates which are nucleoli; wherein the class of condensates comprises condensates which are Oct1/PTF/transcription (OPT) domains; wherein the class of condensates comprises condensates which are paraspeckles; wherein the class of condensates comprises condensates which are perinucleolar compartments; wherein the class of condensates comprises condensates which are PML nuclear bodies; wherein the class of condensates comprises condensates which are PML oncogenic domains; wherein the class of condensates comprises condensates which are polycomb bodies; wherein the class of condensates comprises condensates which are processing bodies; wherein the class of condensates comprises condensates which are Sam68 nuclear bodies; wherein the class of condensates comprises condensates which are stress granules; or wherein the class of condensates comprises condensates which are splicing speckles.

Also provided herein are methods of identifying a plurality of compounds that preferentially affect the level, decrease the level, or increase the level of association of a first macromolecule with one or more target condensates, or that preferentially cause the first macromolecule to associate or disassociate with one or more target condensates, the method comprising performing a method of identifying a compound disclosed herein with a plurality of compounds.

In some embodiments, the method further comprises identifying a characteristic that a subset or all of the identified compounds have in common in addition to ability to preferentially affect the level, decrease the level, or increase the level of association of the first macromolecule with the one or more target condensates, or the ability to preferentially cause the first macromolecule to associate or disassociate with one or more target condensates. In some embodiments, the method further comprises performing a method of identifying a compound disclosed herein for one or more additional test compounds that comprise the identified characteristic. In some embodiments, the method further comprises performing a method of identifying a compound disclosed herein for one or more additional test compounds that do not comprise the identified characteristic.

Also provided herein are methods of identifying a compound characteristic associated with preferentially affecting the level, decreasing the level, or increasing the level of association of a first macromolecule with one or more target condensates, or with preferentially causing the first macromolecule to associate or disassociate with one or more target condensates, the method comprising: (a) performing a method of identifying a plurality of compounds disclosed herein; and (b) identifying a characteristic that a subset or all of the identified compounds have in common in addition to the ability to preferentially affect the level, decrease the level, or increase the level of association of the first macromolecule with one or more target condensates, or the ability to preferentially cause the first macromolecule to associate or disassociate with one or more target condensates.

Also provided herein are methods of designing a compound that preferentially affects the level, decreases the level, or increases the level of association of a first macromolecule with one or more target condensates, or that preferentially causes the first macromolecule to associate or disassociate with one or more target condensates, the method comprising: (a) performing a method of identifying a plurality of compounds disclosed herein; (b) identifying a characteristic that a subset or all of the identified compounds have in common in addition to the ability to preferentially affect the level, decrease the level, or increase the level of association of the first macromolecule with one or more target condensates, or the ability to preferentially cause the first macromolecule to associate or disassociate with one or more target condensates; and (c) designing a compound that comprises the identified characteristic, thereby designing a compound that preferentially affects the level, decreases the level, or increases the level of association of the first macromolecule with one or more target condensates or preferentially causes the first macromolecule to associate or disassociate with one or more target condensates.

Also provided herein are methods of identifying a compound useful for treating a disease in an individual in need thereof, the method comprising: performing a method of identifying a compound disclosed herein, wherein the one or more target condensates is associated with the disease, and identifying the compound that preferentially affects the level, decreases the level, or increases the level of association of the first macromolecule with the one or more target condensates or that that preferentially causes the first macromolecule to associate or disassociate with one or more target condensates for being useful for treating the disease. In some embodiments, the disease is a neurodegenerative, proliferative, immunological, cardiac, or metabolic disease.

Also provided herein are methods of identifying a compound that preferentially affects a level of association of a first macromolecule with a first set of one or more target condensates, the method comprising: performing a method of identifying a compound disclosed herein with the first set of one or more target condensates; and performing a method of identifying a compound disclosed herein with a second set of one or more target condensates wherein the compound preferentially affects the level of association of the first macromolecule with the first set of one or more target condensates if the compound preferentially affects the level of association of the first macromolecule with the first set of one or more target condensates more than the compound preferentially affects the level of association of the first macromolecule with the second set of one or more target condensates. In some embodiments, the compound does not affect the level of association of the first macromolecule with the second set of one or more target condensates.

Also provided herein are methods of identifying a compound that preferentially increases a level of association of a first macromolecule with a first set of one or more target condensates, the method comprising: performing a method of identifying a compound disclosed herein with the first set of one or more target condensates; and performing a method of identifying a compound disclosed herein with a second set of one or more target condensates wherein the compound preferentially increases the level of association of the first macromolecule with the first set of one or more target condensates if the compound preferentially increases the level of association of the first macromolecule with the first set of one or more target condensates more than the compound preferentially increases the level of association of the first macromolecule with the second set of one or more target condensates. In some embodiments, the compound does not increase the level of association of the first macromolecule with the second set of one or more target condensates.

Also provided herein are methods of identifying a compound that preferentially decreases a level of association of a first macromolecule with a first set of one or more target condensates, the method comprising: performing a method of identifying a compound disclosed herein with the first set of one or more target condensates; and performing a method of identifying a compound disclosed herein with a second set of one or more target condensates wherein the compound preferentially decreases the level of association of the first macromolecule with the first set of one or more target condensates if the compound preferentially decreases the level of association of the first macromolecule with the first set of one or more target condensates more than the compound preferentially decreases the level of association of the first macromolecule with the second set of one or more target condensates. In some embodiments, the compound does not decrease the level of association of the first macromolecule with the second set of one or more target condensates.

Also provided herein are methods of identifying a compound that preferentially causes a first macromolecule to associate with a first set of one or more target condensates, the method comprising: performing a method of identifying a compound disclosed herein with the first set of one or more target condensates; and performing a method of identifying a compound disclosed herein with a second set of one or more target condensates wherein the compound preferentially causes the first macromolecule to associate with the first set of one or more target condensates if the compound preferentially causes the first macromolecule to associate with the first set of one or more target condensates more than the compound preferentially causes the first macromolecule to associate with the second set of one or more target condensates.

Also provided herein are methods of identifying a compound that preferentially causes a first macromolecule to disassociate with a first set of one or more target condensates, the method comprising: performing a method of identifying a compound disclosed herein with the first set of one or more target condensates; and performing a method of identifying a compound disclosed herein with a second set of one or more target condensates wherein the compound preferentially causes the first macromolecule to disassociate with the first set of one or more target condensates if the compound preferentially causes the first macromolecule to associate with the first set of one or more target condensates more than the compound preferentially causes the first macromolecule to associate with the second set of one or more target condensates.

In some embodiments, the first and/or second set of one or more target condensates is a cellular condensate. In some embodiments, the first and/or second set of one or more target condensates is a nuclear condensate or a cytoplasmic condensate.

In some embodiments, the first and/or second set of one or more target condensates is a cleavage body, a p-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

In some embodiments, the first and/or second set of one or more target condensates is a single target condensate.

In some embodiments, the first and/or second set of one or more target condensates is a plurality of target condensates. In some embodiments, the first and/or second set of one or more target condensates is all or a subset of a class of condensates in a portion of the cellular composition. In some embodiments, the first and/or second set of one or more target condensates is all or a subset of a class of condensates in a cell in the cellular composition. In some embodiments, the first and/or second set of one or more target condensates is all or a subset of a class of condensates in a portion of a cell in the cellular composition. In some embodiments, the portion of the cell is the cytoplasm, the nucleus, or an organelle.

In some embodiments, the class of condensates comprises condensates which comprise a specific macromolecule. In some embodiments, the class of condensates comprises condensates which are cleavage bodies; wherein the class of condensates comprises condensates which are p-granules; wherein the class of condensates comprises condensates which are histone locus bodies; wherein the class of condensates comprises condensates which are multivesicular bodies; wherein the class of condensates comprises condensates which are neuronal RNA granules; wherein the class of condensates comprises condensates which are nuclear gems; wherein the class of condensates comprises condensates which are nuclear pores; wherein the class of condensates comprises condensates which are nuclear speckles; wherein the class of condensates comprises condensates which are nuclear stress bodies; wherein the class of condensates comprises condensates which are nucleoli; wherein the class of condensates comprises condensates which are Oct1/PTF/ transcription (OPT) domains; wherein the class of condensates comprises condensates which are paraspeckles; wherein the class of condensates comprises condensates which are perinucleolar compartments; wherein the class of condensates comprises condensates which are PML nuclear bodies; wherein the class of condensates comprises condensates which are PML oncogenic domains; wherein the class of condensates comprises condensates which are polycomb bodies; wherein the class of condensates comprises condensates which are processing bodies; wherein the class of condensates comprises condensates which are Sam68 nuclear bodies; wherein the class of condensates comprises condensates which are stress granules; or wherein the class of condensates comprises condensates which are splicing speckles.

In some embodiments, the class of the first set of one or more target condensates is the same as the class of second set of one or more target condensates. In some embodiments, the class of the first set of one or more target condensates is different than the class of second set of one or more target condensates.

In some embodiments, the first set of one or more target condensates is in the same cellular composition as the second set of one or more target condensates. In some embodiments, the cellular composition comprises a cell comprising the first set of condensate of one or more target condensates and the second set of one or more target condensates. In some embodiments, the first set of condensate of one or more target condensates is in a first cellular composition, and the second set of one or more target condensates is in a second cellular composition.

In some embodiments, the first set of condensate of one or more target condensates are in a cell in the cellular composition, and the cell has one or more features of a disease. In some embodiments, the disease is a neurodegenerative, proliferative, immunological, cardiac, or metabolic disease.

Also provided herein are methods of identifying a plurality of compounds that preferentially affect the level, decrease the level, or increase the level of association of a first macromolecule with a first set of one or more target condensates, or that preferentially cause the first macromolecule to associate or disassociate with the first set of one or more target condensates, the method comprising performing a method of identifying a compound disclosed herein with a plurality of compounds.

In some embodiments, the method further comprises identifying a characteristic that a subset or all of the identified compounds have in common in addition to ability to preferentially affect the level, decrease the level, or increase the level of association of the first macromolecule with the first set of one or more target condensates, or the ability to preferentially cause the first macromolecule to associate or disassociate with the first set of one or more target condensates.

In some embodiments, the method further comprises performing a method of identifying a compound disclosed herein for one or more additional test compounds that comprise the identified characteristic. In some embodiments, the method further comprises performing a method of identifying a compound disclosed herein for one or more additional test compounds that do not comprise the identified characteristic.

Also provided herein are methods of identifying a compound characteristic associated with preferentially affecting the level, decreasing the level, or increasing the level of association of a first macromolecule with a first set of one or more target condensates, or with preferentially causing the first macromolecule to associate or disassociate with the first set of one or more target condensates, the method comprising: (a) performing a method of identifying a plurality of compounds disclosed herein; and (b) identifying a characteristic that a subset or all of the identified compounds have in common in addition to the ability to preferentially affect the level, decrease the level, or increase the level of association of the first macromolecule with the first set of one or more target condensates, or the ability to preferentially cause the first macromolecule to associate or disassociate with the first set of one or more target condensates.

Also provided herein are methods of designing a compound that preferentially affects the level, decreases the level, or increases the level of association of a first macromolecule with a first set of one or more target condensates, or that preferentially causes the first macromolecule to associate or disassociate with the first set of one or more target condensates, the method comprising: (a) performing a method of identifying a plurality of compounds disclosed herein; (b) identifying a characteristic that a subset or all of the identified compounds have in common in addition to the ability to preferentially affect the level, decrease the level, or increase the level of association of the first macromolecule with the first set of one or more target condensates, or the ability to preferentially cause the first macromolecule to associate or disassociate with the first set of one or more target condensates; and (c) designing a compound that comprises the identified characteristic, thereby designing a compound that preferentially affects the level, decreases the level, or increases the level of association of the first macromolecule with the first set of one or more target condensates or preferentially causes the first macromolecule to associate or disassociate with the first set of one or more target condensates.

Also provided herein are methods of identifying a compound useful for treating a disease in an individual in need thereof, the method comprising: performing a method of identifying a compound disclosed herein, wherein the first set of one or more target condensates is associated with the disease, and identifying the compound that preferentially affects the level, decreases the level, or increases the level of association of the first macromolecule with the first set of one or more target condensates or that that preferentially causes the first macromolecule to associate or disassociate with the first set of one or more target condensates for being useful for treating the disease. In some embodiments, the disease is a neurodegenerative, proliferative, immunological, cardiac, or metabolic disease.

DETAILED DESCRIPTION

Figure 1:
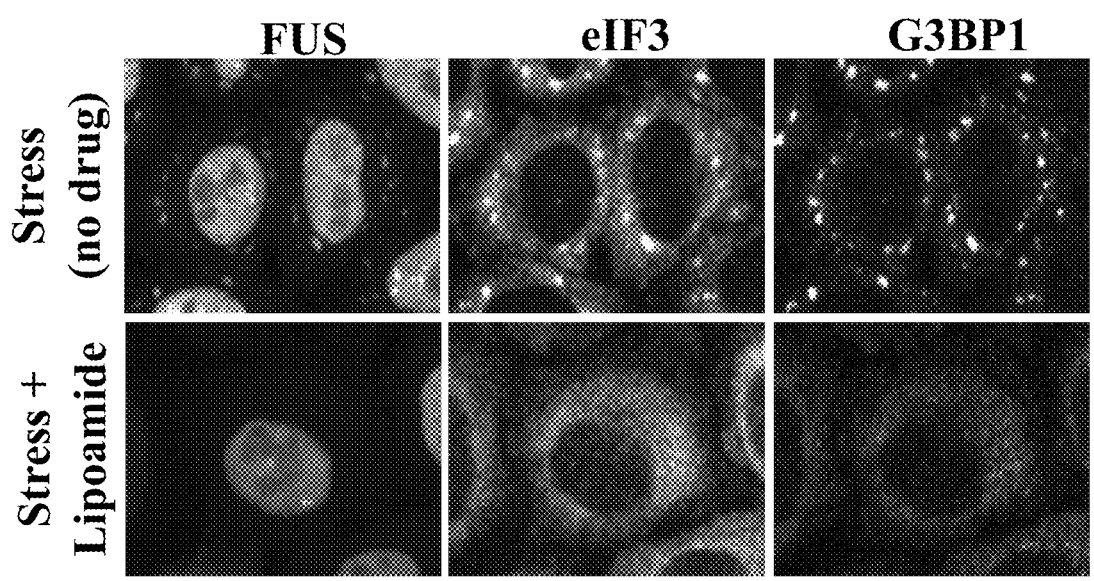
FIG. 1 is fluorescent micrographs showing the levels of FUS, eIF3, and G3BP1 in stressed cells with or without treatment with lipoamide.

Aberrant condensate formation and/or solidification have been associated with some diseases, including neurodegenerative diseases such as ALS. Previously, drug screening for a compound useful in treating a disease associated with aberrant condensates was focused on screening for drugs that prevent formation and/or completely dissolve the condensates. The disclosure of the present application is based, at least in part, on the inventors' unique insights and unexpected findings that screens can be developed to identify compounds that selectively alter a condensate, such as the composition of the condensate, without disrupting the entire condensate or disrupting certain other condensates. The methods disclosed herein enable techniques for screening and identifying compounds, or portions thereof, having any one or more of the following specificities: selectivity modulating the inclusion or exclusion of a macromolecule in a condensate (macromolecule specificity); selectivity affecting one type of a condensate and not another type of a condensate (condensate specificity); and selectively affecting condensates in one type of tissue and not another type of tissue (tissue specificity). Identifying and developing compounds having selective control of a specific macromolecule's behavior with respect to a condensate and/or selective control of an impacted condensate and/or selective control of an impacted tissue types are powerful strategies for therapeutic intervention to reverse a disease phenotype while minimizing off target activity. For example, compounds that can selectively alter the composition of a condensate, specific types of condensates, and/or condensates in specific tissue types could be useful for specifically inhibiting or activating biological pathways depending precisely on the needs associated with the treatment of the disease.

Thus, in some aspects, provided herein are methods of identifying a compound having any one or more of the following specificities: macromolecule specificity, condensate specificity, and tissue specificity, the method comprising determining a level of association of a first macromolecule with one or more target condensates, and comparing the level of association with a reference level to identify the compound having the one or more of the specificities. In some embodiments, the method identifies a compound having macromolecule specificity. In some embodiments, the method identifies a compound having condensate specificity. In some embodiments, the method identifies a compound having tissue (e.g., cell type) specificity. In some embodiments, the method identifies a compound having macromolecule specificity and condensate specificity. In some embodiments, the method identifies a compound having macromolecule specificity and tissue (e.g., cell type) specificity. In some embodiments, the method identifies a compound having condensate specificity and tissue (e.g., cell type) specificity. In some embodiments, the method identifies a compound having macromolecule specificity, condensate specificity, and tissue (or cell type) specificity.

In other aspects, provided herein are methods of identifying a compound that preferentially affects, such as preferentially increases or preferentially decreases, a level of association of a first macromolecule with one or more target condensates.

Also provided herein are methods of identifying a compound that preferentially causes a first macromolecule to associate or disassociate with one or more target condensates.

As described herein, the methods of identifying compounds may be useful for, e.g., identifying, characterizing, and developing compounds or moieties thereof, capable of altering the behavior of the macromolecule with a condensate, including for use in the treatment of a disease in an individual.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-translational modifications of the polypeptide, for example, glycosylation, sialylation, acetylation, phosphorylation, and the like.

As used herein, "cellular composition" is a composition comprising at least one cell. Exemplary compositions include a tissue sample or cultured cells.

As used herein a "condensate" means a non-membrane-encapsulated compartment formed by phase separation of one or more of proteins and/or other macromolecules (including all stages of phase separation).

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

The section headings used herein are for organizational purposes only and are not to be construed as limiting the subject matter described.

Methods of Identifying Compounds

Provided herein are methods of identifying a compound having any one or more of the following specificities: macromolecule specificity, condensate specificity, and tissue specificity.

In some embodiments, the method of identifying comprises (a) contacting a composition with a compound, wherein (i) the composition comprises one or more target condensates; and/or (ii) the one or more target condensates form simultaneously with and/or after contacting the composition with the compound; (b) determining a level of association of a first macromolecule with the one or more target condensates; and (c) comparing the level of association of the first macromolecule with the one or more target condensates and a reference level to identify the compound having one or more of the following specificities: macromolecule specificity, condensate specificity, and tissue specificity. In some embodiments, the composition is a cellular composition, e.g., a cell culture. In some embodiments, the one or more target condensates are in a particular type of tissue (e.g., cell type).

In some embodiments, provided is a method of identifying a compound having macromolecule specificity. In some embodiments, the method comprises (a) contacting a composition with a compound, wherein (i) the composition comprises one or more target condensates; and/or (ii) the one or more target condensates form simultaneously with and/or after contacting the composition with the compound; (b) determining a level of association of a first macromolecule with the one or more target condensates; and (c) comparing the level of association of the first macromolecule with the one or more target condensates and a reference level to identify the compound having macromolecule specificity, wherein the reference level comprises any one or more of (i) a level of association of the first macromolecule with the one or more target condensates when the composition is not contacted with the compound, (ii) a level of association of one or more other macromolecules with the one or more target condensates in the composition contacted with the compound, (iii) a level of association of one or more other macromolecules with the one or more target condensates when the composition is not contacted with the compound. In some embodiments, the reference level is a level of association of a second macromolecule with the one or more target condensates in the composition. In some embodiments, the reference level is a level of association of the first macromolecule with a reference condensate. In some embodiments, the first macromolecule, the one or more target condensates, and the reference condensate are in the same composition. In some embodiments, the one or more target condensates and the reference condensate are in different compositions. In some embodiments, the reference level is a level of association of the first macromolecule with the one or more target condensates in a reference system not treated with the compound. In some embodiments, the reference system is treated with a vehicle control. In some embodiments, the composition is a cellular composition. In some embodiments, wherein the composition is a cellular composition, the composition and the reference system comprise the same cell type. In some embodiments, the methods described herein are useful for identifying a compound that exhibits specificity for a single macromolecule (such as exhibits an action and/or activity associated with the single macromolecule in regards to interactions with a condensate). In some embodiments, the methods described herein are useful for identifying a compound that exhibits specificity for a set of macromolecules (such as exhibits an action and/or activity associated with the set of macromolecules in regards to interactions with a condensate). In some embodiments, the one or more target condensates are in a particular type of tissue (e.g., cell type). In some embodiments, the method further comprises assessing the compound for condensate specificity and/or tissue specificity.

In some embodiments, provided is a method of identifying a compound having condensate specificity. In some embodiments, the method comprises (a) contacting a composition with a compound, wherein (i) the composition comprises one or more target condensates; and/or (ii) the one or more target condensates form simultaneously with and/or after contacting the composition with the compound; (b) determining a level of association of a first macromolecule with the one or more target condensates; and (c) comparing the level of association of the first macromolecule with the one or more target condensates and a reference level to identify the compound having condensate specificity, wherein the reference level comprises any one or more of (i) a level of association of the first macromolecule with another condensate (in the presence or absence of the compound), (ii) a level of association of one or more other macromolecules with another condensate (in the presence or absence of the compound), (iii) a level of association of one or more other macromolecules with the one or more target condensates (in the presence or absence of the compound), (iv) a characteristic, such as size, number, volume, of the one or more target condensates (or characteristic, such as distribution, amount, diffusion coefficient, of a condensate component), and (v) a characteristic, such as size, number, volume, of another condensate (or characteristic, such as distribution, amount, diffusion coefficient, of a condensate component). In some embodiments, the reference level is a level of association of a second macromolecule with a reference condensate. In some embodiments, the first macromolecule and the second macromolecule are the same. In some embodiments, the first macromolecule and the second macromolecule are different. In some embodiments, the second macromolecule and the reference condensate are in the same composition as the first macromolecule and the one or more target condensates. In some embodiments, the composition is a cellular composition. In some embodiments, wherein the composition is a cellular composition, the composition and the reference system comprise the same cell type. In some embodiments, the method comprises (a) contacting a composition with a compound, wherein (i) the composition comprises one or more target condensates; and/or (ii) the one or more target condensates form simultaneously with and/or after contacting the composition with the compound; (b) determining a characteristic of the one or more target condensates; and (c) comparing the characteristic of the one or more target condensates with a characteristic of a reference condensate to identify the compound having condensate specificity. In some embodiments, the characteristic of the one or more target condensates is one or more of: (i) amount of the first macromolecule present in the one or more target condensates; (ii) size of the one or more target condensates; (iii) surface area of the one or more target condensates; (iv) volume of the one or more target condensates; (v) amount, such as total amount, of the one or more target condensates; (vi) number of the one or more target condensates; and (vii) number and size of the one or more target condensates. In some embodiments, the characteristic of the reference condensate is one or more of: (i) amount of a component, such as a macromolecule, present in the reference condensate; (ii) size of the reference condensate; (iii) surface area of the reference condensate; (iv) volume of the reference condensate; (v) amount, such as total amount, of the reference condensate; (vi) number of the reference condensate; and (vii) number and size of the reference condensate. In some embodiments, the compared characteristic is the same characteristic for both the one or more target condensates and the reference condensate. In some embodiments, the methods described herein are useful for identifying a compound that exhibits specificity in a single condensate type (such as exhibits an action and/or activity associated with a single condensate type). In some embodiments, the methods described herein are useful for identifying a compound that exhibits specificity in a set of condensate types (such as exhibits an action and/or activity associated with the set of condensate types), such as a set of condensate types that all comprise the first macromolecule. In some embodiments, the one or more target condensates are in a particular type of tissue (e.g., cell type). In some embodiments, the method further comprises assessing the compound for macromolecule specificity and/or tissue specificity.

In some embodiments, provided is a method of identifying a compound having tissue (or cell type) specificity. In some embodiments, the method comprises (a) contacting a composition comprising a cell with a compound, wherein (i) the composition comprises one or more target condensates; and/or (ii) the one or more target condensates form simultaneously with and/or after contacting the composition with the compound; (b) determining a level of association of a first macromolecule with the one or more target condensates; and (c) comparing the level of association of the first macromolecule with the one or more target condensates and a reference level to identify the compound having tissue specificity, wherein the reference level comprises any one or more of (i) a level of association of the first macromolecule with the one or more target condensates in another cell of a different cell type than the cell of the composition (in the presence or absence of the compound), (ii) a level of association of the first macromolecule with another condensate in the cell of the composition (in the presence or absence of the compound), (iii) a level of association of the first macromolecule with another condensate in another cell of a different cell type than the cell of the composition (in the presence or absence of the compound), (iv) a level of association of one or more other macromolecules with the one or more target condensates in the cell of the composition (in the presence or absence of the compound), (v) a level of association of one or more other macromolecules with another condensate in the cell of the composition (in the presence or absence of the compound), (vi) a level of association of one or more other macromolecules with the one or more target condensates in another cell of a different cell type than the cell of the composition (in the presence or absence of the compound), (vii) a level of association of one or more other macromolecules with another condensate or more other macromolecules with another condensate in another cell of a different cell type than the cell of the composition (in the presence or absence of the compound), (viii) a characteristic, such as size, number, volume, of the one or more target condensates (or characteristic, such as distribution, amount, diffusion coefficient, of a condensate component) in the cell of the composition, (ix) a characteristic, such as size, number, volume, of the one or more target condensates (or characteristic, such as distribution, amount, diffusion coefficient, of a condensate component) in another cell of a different cell type than the cell of the composition, (x), a characteristic, such as size, number, volume, of another condensate (or characteristic, such as distribution, amount, diffusion coefficient, of a condensate component) in the cell of the composition, and (xi) a characteristic, such as size, number, volume, of another condensate (or characteristic, such as distribution, amount, diffusion coefficient, of a condensate component) in another cell of a different cell type than the cell of the composition. In some embodiments, the reference level is a level of association of the first macromolecule with the one or more target condensates in a reference system, wherein the reference system is a model for a different tissue (or cell) type than the composition comprising the one or more target condensates. In some embodiments, the reference system is contacted with the compound. In some embodiments, the composition is a cellular composition. In some embodiments, wherein the composition is a cellular composition, the composition and the reference system comprise different cell types. In some embodiments, the methods described herein are useful for identifying a compound that exhibits specificity in a single tissue or cell type (such as exhibits an action and/or activity associated with a condensate in the single tissue or cell type). In some embodiments, the methods described herein are useful for identifying a compound that exhibits specificity in a set of tissue or cell types (such as exhibits an action and/or activity associated with a condensate in the set of tissue or cell types), such as a set of tissue of cell types that all comprise the first macromolecule and the one or more target condensates. In some embodiments, the one or more target condensates are in a particular type of tissue (e.g., cell type). In some embodiments, the method further comprises assessing the compound for macromolecule specificity and/or condensate specificity.

For example, in some embodiments, the methods described herein are useful for identifying a compound that preferentially affects the association of one or more macromolecules (e.g., a first macromolecule, one or more other macromolecules, and/or one or more reference molecules) with one or more target condensates in a first cell type compared to a second cell type, such as the association of any macromolecule with a target condensate in a first cell type compared to a second cell type (hereinafter also referred to as "condensate+cell type selectivity"). In some embodiments, the method comprises: 1) comparing the level of association of the one or more macromolecules with the one or more target condensates in the first cell type composition in the presence of the compound, with the level of association of the one or more macromolecules with the one or more target condensates in the second cell type composition in the presence of the compound, and 2) comparing the level of association of the one or more macromolecules with the one or more other condensates in the first cell type composition in the presence of the compound, with the level of association of the one or more macromolecules with the one or more other condensates in the second cell type composition in the presence of the compound, if a) the level of association of the one or more macromolecules with the one or more target condensates in the first cell type composition is altered more (e.g., at least about 2 fold more) than the level of association of the one or more macromolecules with the one or more target condensates in the second cell type composition, and b) the level of association of the one or more macromolecules with the one or more other condensates in the first cell type composition is not altered, or not significantly altered (e.g., altered less than about 2 fold) compared to the level of association of the one or more macromolecules with the one or more other condensates in the second cell type composition, the compound is identified as preferentially affecting the association of one or more macromolecules with one or more target condensates in a first cell type compared to a second cell type. In some embodiments, the method further comprises comparing: 1) the level of association of a first macromolecule with the one or more target condensates in the first cell type composition in the presence of the compound, with the level of association of the first macromolecule with the one or more target condensates in the second cell type composition in the presence of the compound; and 2) the level of association of a second macromolecule with the one or more target condensates in the first cell type composition in the presence of the compound, with the level of association of the second macromolecule with the one or more target condensates in the second cell type composition in the presence of the compound; if a compound preferentially affects the association of the first macromolecule with one or more target condensates in a first cell type compared to a second cell type similarly to (e.g., within about 2 fold range) how the compound preferentially affects the association of the second macromolecule with one or more target condensates in a first cell type compared to a second cell type, the compound is not identified as with preferential selectivity over macromolecule type.

In some embodiments, the methods described herein are useful for identifying a compound that preferentially affects the association of a first macromolecules with one or more condensates (e.g., one or more target condensates, one or more other condensates, and/or one or more reference condensates) in a first cell type compared to a second cell type, such as the association of a first macromolecule with any condensates in a first cell type compared to a second cell type (hereinafter also referred to as "macromolecule+cell type selectivity"). In some embodiments, the method comprises: 1) comparing the level of association of the first macromolecule with the one or more condensates in the first cell type composition in the presence of the compound, with the level of association of the first macromolecule with the one or more condensates in the second cell type composition in the presence of the compound, and 2) comparing the level of association of one or more other macromolecules with the one or more condensates in the first cell type composition in the presence of the compound, with the level of association of the one or more other macromolecules with the one or more condensates in the second cell type composition in the presence of the compound, if a) the level of association of the first macromolecule with the one or more condensates in the first cell type composition is altered more (e.g., at least about 2 fold more) than the level of association of the first macromolecule with the one or more condensates in the second cell type composition, and b) the level of association of the one or more other macromolecules with the one or more condensates in the first cell type composition is not altered, or not significantly altered (e.g., altered less than about 2 fold) compared to the level of association of the one or more other macromolecules with the one or more condensates in the second cell type composition, the compound is identified as preferentially affecting the association of the first macromolecules with one or more condensates in a first cell type compared to a second cell type.

In some embodiments, the methods described herein comprise comparing a level of association of a first macromolecule with one or more target condensates and a reference level. As described herein, the reference level provides the comparison needed to identify whether a compound exhibits any one or more of the following specificities: selectivity modulating the inclusion or exclusion of a macromolecule in a condensate (macromolecule specificity); selectivity affecting one type of a condensate and not another type of a condensate (condensate specificity); and selectively affecting condensates in one type of tissue and not another type of tissue (tissue specificity). In some embodiments, the level of association of a first macromolecule with one or more target condensates is obtained/assessed via any one or more of the following: (i) the amount (such as quantity, e.g., absolute quantity) of the first macromolecule in the one or more target condensates; (ii) the amount (such as quantity, e.g., absolute quantity) of the first macromolecule not in the one or more target condensates; (iii) the intensity of signal from the first macromolecule in the one or more target condensates; (iv) the number of the one or more target condensates comprising the first macromolecule; (v) the size of the one or more target condensates comprising the first macromolecule; (vi) the surface area of the one or more target condensates comprising the first macromolecule; (vii) the volume of the one or more target condensates comprising the first macromolecule; and (vii) the number and size of the one or more target condensates comprising the first macromolecule. The references levels described herein can be obtained/assessed in a similar manner as described for the other macromolecules described herein (such as the first macromolecule).

In any of the embodiments described herein, the level of association, such as a level of association of a first macromolecule with one or more target condensates, is assessed at more than one compound concentration. In some embodiments, the method comprises determining a dose-response curve (similar to an $IC_{50}$ curve) using the information obtained from the analysis at the more than one compound concentration. In some embodiments, the method comprises determining a potency (similar to an $IC_{50}$) of the compound using the dose-response curve. In some embodiments, the method comprises identifying a compound having any one or more of the following specificities: macromolecule specificity, condensate specificity, and tissue specificity, wherein the method comprises comparing the dose-response curve obtained for a compound with one or more target condensates and a reference dose-response curve. In some embodiments, the method comprises identifying a compound having any one or more of the following specificities: macromolecule specificity, condensate specificity, and tissue specificity, wherein the method comprises comparing the potency obtained for a compound with one or more target condensates and a reference potency.

In some embodiments, provided herein are methods of identifying a compound comprising: (a) contacting a cellular composition with a compound, wherein (i) the cellular composition comprises one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates. In some embodiments, the method is a method of identifying a compound that preferentially affects the level of association of a first macromolecule with one or more target condensates. In some embodiments, the method is a method of identifying a compound that preferentially increases a level of association of a first macromolecule with one or more target condensates. In some embodiments, the method is a method of identifying a compound that preferentially decreases a level of association of a first macromolecule with one or more target condensates. In some embodiments, the method is a method of identifying a compound useful for treating a disease in an individual in need thereof, wherein the one or more target condensates is associated with the disease. In some embodiments, the disease is a neurodegenerative, proliferative, immunological, cardiac, or metabolic disease.

In some embodiments, the one or more target condensates are only present under the disease (or stressed) status. In some embodiments, the one or more target condensates have changes in one or more of the following characteristics under the disease (or stressed) status compared to healthy (or non-stressed) status: (i) location of the one or more target condensates; (ii) distribution of the one or more target condensates and/or its component (e.g., the first macromolecule); (iii) number of the one or more target condensates; (iv) size of the one or more target condensates; (v) ratio of the amount of one or more target condensates and a reference condensate; (vi) a functional activity associated with the one or more target condensates; (vii) composition of the one or more target condensates; (viii) co-localization of the one or more target condensates with a biomolecule; (ix) diffusion coefficient of a component (e.g., the first macromolecule) of the one or more target condensates; (x) stability of the one or more target condensates; (xi) dissolution or reduction in size of the one or more target condensates; (xii) surface area of the one or more target condensates; (xiii) sphericity of the one or more target condensates; (xiv) liquidity of the one or more target condensates; (xv) solidification of the one or more target condensates; (xvi) location of a condensate component (e.g., the first macromolecule); (xvii) amount of a condensate component (e.g., the first macromolecule) or a precursor thereof; (xviii) condensate partitioning of a biomolecule (e.g., the first macromolecule) into the one or more target condensates; (xix) a functional activity associated with a condensate component (e.g., the first macromolecule); (xx) aggregation of a condensate component (e.g., the first macromolecule); (xxi) post-translational modification status of a condensate component (e.g., the first macromolecule); and (xxii) amount of a degradation product of a condensate component (e.g., the first macromolecule). In some embodiments, the first macromolecule has an increased level of association with the one or more target condensates under a disease (or stressed) status, and the methods described herein are used to identify a compound that selectively reduces the association of the first macromolecule with the one or more target condensates compared to a reference level. For example, the methods described herein are useful for identifying a compound that preferentially reduces the association of the first macromolecule with the one or more target condensates, compared to the association of another biomolecule (e.g., a condensate component that is not the first macromolecule) with the one or more target condensates. In some embodiments, the methods described herein are useful for identifying a compound that preferentially reduces the association of the first macromolecule with the one or more target condensates, compared to the association of the first macromolecule to another condensate, or the association of a second macromolecule to another condensate. In some embodiments, the methods described herein are useful for identifying a compound that preferentially reduces the association of the first macromolecule with the one or more target condensates in the diseased (or stressed) tissue or cell type, compared to the association of the first macromolecule with the one or more target condensates or another condensate in a healthy (or non-stressed) tissue or cell type, or compared to the association of a second macromolecule with the one or more target condensates or another condensate in a healthy (or non-stressed) tissue or cell type. In some embodiments, the second macromolecule and the first macromolecule are different. In some embodiments, the second macromolecule is a reference macromolecule (e.g., a macromolecule known to be associated with a target condensate, or known not to be associated with a target condensate under healthy or non-stressed condition or cell/tissue type).

Also provided herein are methods of identifying a plurality of compounds comprising: (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates, and (c) performing steps (a) and (b) for a plurality of compounds. In some embodiments, the method is a method of identifying a plurality of compounds that preferentially affects the level of association of a first macromolecule with one or more target condensates. In some embodiments, the method is a method of identifying a plurality of compounds that preferentially increases a level of association of a first macromolecule with one or more target condensates. In some embodiments, the method is a method of identifying a plurality of compounds that preferentially decreases a level of association of a first macromolecule with one or more target condensates. In some embodiments, the method further comprises comparing the level of association of the first macromolecule with the one or more target condensates when contacted with different compounds. In some embodiments, the method further comprises ranking the plurality of compounds identified based on their actions and/or activity in preferentially increasing (or decreasing) the level of association of the first macromolecule with the one or more target condensates. In some embodiments, the comparison or ranking is based on the absolute action and/or activity of the compound in increasing (or decreasing) the level of association of the first macromolecule with the one or more target condensates. In some embodiments, the comparison or ranking is based on the relative action and/or activity in preferentially increasing (or decreasing) the level of association of the first macromolecule with the one or more target condensates compared to that of the at least one additional macromolecule with the one or more target condensates. In some embodiments, the method is a method of identifying a plurality of compounds useful for treating a disease in an individual in need thereof, wherein the one or more target condensates is associated with the disease. In some embodiments, the disease is a neurodegenerative, proliferative, immunological, cardiac, or metabolic disease.

In some embodiments, the method further comprises identifying a characteristic that a subset or all of the identified compounds have in common in addition to the ability to preferentially affect the level, decrease the level, or increase the level of association of the first macromolecule with the one or more target condensates. In some embodiments, the method further comprises identifying a characteristic that a subset or all of the identified compounds have in common in addition to the ability to preferentially affect the level of association of the first macromolecule with the one or more target condensates. In some embodiments, the method further comprises identifying a characteristic that a subset or all of the identified compounds have in common in addition to the ability to preferentially decrease the level of association of the first macromolecule with the one or more target condensates. In some embodiments, the method further comprises identifying a characteristic that a subset or all of the identified compounds have in common in addition to the ability to preferentially increase the level of association of the first macromolecule with the one or more target condensates. In some embodiments, the method further comprises performing step (a) contacting a cellular composition with a compound, wherein (i) the cellular composition comprises one or more target condensates; and/or (ii) the one or more target condensates form simultaneously with and/or after contacting the cellular composition with the compound and step (b) determining the level of association of the first macromolecule with the one or more target condensates and a level of association of at least one additional macromolecule with the one or more target condensates, for one or more additional test compounds that comprise the identified characteristic. In some embodiments, the method further comprises performing steps (a) and (b) for one or more additional test compounds that do not comprise the identified characteristic. In some embodiments, the characteristic is a compound moiety.

In some embodiments, the first reference level is a level of association of the first macromolecule with one or more reference condensates determined in the absence of the compound. In some embodiments, the reference level for each (or at least one) additional macromolecule is a level of association for each (or at least one) additional macromolecule with one or more reference condensates determined in the absence of the compound.

In some embodiments, the compound preferentially affects the level of association of the first macromolecule with the one or more target condensates if the compound alters the level of association of the first macromolecule with the one or more target condensates as compared to a first reference level more than the compound alters the level of association of each (or at least one) additional macromolecule with the one or more target condensates as compared to a reference level for each (or at least one) additional macromolecule. In some embodiments, the compound preferentially increases the level of association of the first macromolecule with the one or more target condensates if the compound increases the level of association of the first macromolecule with the one or more target condensates as compared to a first reference level more than the compound increases the level of association of each (or at least one) additional macromolecule with the one or more target condensates as compared to a reference level for each (or at least one) additional macromolecule. In some embodiments, the compound preferentially decreases the level of association of the first macromolecule with the one or more target condensates if the compound decreases the level of association of the first macromolecule with the one or more target condensates as compared to a first reference level more than the compound decreases the level of association of each (or at least one) additional macromolecule with the one or more target condensates as compared to a reference level for each (or at least one) additional macromolecule.

In some embodiments, the compound increases the level of association of the first macromolecule with the one or more target condensates compared to the first reference level. In some embodiments, the compound decreases the level of association of the first macromolecule with the one or more target condensates compared to the first reference level. In some embodiments, the compound increases or does not measurably alter the level of association of each (or at least one) additional macromolecule compared to the reference level for each (or at least one) additional macromolecule. In some embodiments, the compound decreases or does not measurably alter the level of association of each (or at least one) additional macromolecule compared to the reference level for each (or at least one) additional macromolecule. In some embodiments, the compound does not measurably alter the level of association of each (or at least one) additional macromolecule compared to the reference level for each (or at least one) additional macromolecule. In some embodiments, the compound does not measurably increase the level of association of each (or at least one) additional macromolecule compared to the reference level for each (or at least one) additional macromolecule. In some embodiments, the compound does not measurably decrease the level of association of each (or at least one) additional macromolecule compared to the reference level for each (or at least one) additional macromolecule. In some embodiments, the method comprises determining the first reference level and the reference level of each (or at least one) additional macromolecule.

In some embodiments, the compound increases the level of association of the first macromolecule with the one or more target condensates increases compared to the first reference level, and the compound does not increase the level of association of each (or at least one) additional macromolecule compared to the reference level for each (or at least one) additional macromolecule; or the compound decreases the level of association of the first macromolecule with the one or more target condensates compared to the first reference level, and the compound does not increase the level of association of each (or at least one) additional macromolecule compared to the reference level for each (or at least one) additional macromolecule. In some embodiments, the compound increases the level of association of the first macromolecule with the one or more target condensates compared to the first reference level, and the compound does not increase the level of association of each (or at least one) additional macromolecule compared to the reference level for each (or at least one) additional macromolecule. In some embodiments, the compound decreases the level of association of the first macromolecule with the one or more target condensates compared to the first reference level, and the compound does not decrease the level of association of each (or at least one) additional macromolecule compared to the reference level for each (or at least one) additional macromolecule.

In some embodiments, the compound preferentially affects the level of association of the first macromolecule with the one or more target condensates if the compound alters the level of the first macromolecule as compared to a first reference level more than the compound alters the level of each (or at least one) additional macromolecule as compared to a reference level for each (or at least one) additional macromolecule, and the difference is statistically significant. In some embodiments, the compound preferentially increases the level of association of the first macromolecule with the one or more target condensates if the compound increases the level of the first macromolecule as compared to a first reference level more than the compound alters the level of each (or at least one) additional macromolecule as compared to a reference level for each (or at least one) additional macromolecule, and the difference is statistically significant. In some embodiments, the compound preferentially decreases the level of association of the first macromolecule with the one or more target condensates if the compound decreases the level of the first macromolecule as compared to a first reference level more than the compound alters the level of each (or at least one) additional macromolecule as compared to a reference level for each (or at least one) additional macromolecule, and the difference is statistically significant. In some embodiments, the difference is statistically significant if p<0.05, such as p<0.025, 0.01, 0.005, or 0.001. Methods of determining statistical significance as known, such as t-tests, ANOVA, and Fisher's method. Selection of the appropriate test can be determined by one of skill in the art.

In some embodiments, the compound preferentially affects the level of association of the first macromolecule with the one or more target condensates if the compound alters the level of the first macromolecule as compared to a first reference level at least about 2 fold more than the compound alters the level of each (or at least one) additional macromolecule as compared to a reference level for each (or at least one) additional macromolecule, such as at least about any of 2.5 fold, 3 fold, 4 fold, 5 fold, or 10 fold. In some embodiments, the compound preferentially increases the level of association of the first macromolecule with the one or more target condensates if the compound increases the level of the first macromolecule as compared to a first reference level at least about 2 fold more than the compound alters the level of each (or at least one) additional macromolecule as compared to a reference level for each (or at least one) additional macromolecule, such as at least about any of 2.5 fold, 3 fold, 4 fold, 5 fold, or 10 fold. In some embodiments, the compound preferentially decreases the level of association of the first macromolecule with the one or more target condensates if the compound decreases the level of the first macromolecule as compared to a first reference level at least about 2 fold more than the compound alters the level of each (or at least one) additional macromolecule as compared to a reference level for each (or at least one) additional macromolecule, such as at least about any of 2.5 fold, 3 fold, 4 fold, 5 fold, or 10 fold. In some embodiments, the compound preferentially affects the level of association of the first macromolecule with the one or more target condensates if the compound alters the level of association of the first macromolecule with the one or more target condensates as compared to a first reference level at least about any of 0.25 fold, 0.5 fold, 0.75 fold, 1 fold, 1.25 fold, 1.5 fold, 1.75 fold, 2 fold, 2.5 fold, 3 fold, 4 fold, 5 fold, or 10 fold more than the compound alters the level of association of each (or at least one) additional macromolecule with the one or more target condensates as compared to a reference level for each (or at least one) additional macromolecule.

In some embodiments, the compound preferentially affects the level of association of the first macromolecule with the one or more target condensates if the compound alters the level of association of the first macromolecule with the one or more target condensates as compared to a first reference level more than (such as at least about any of 0.25 fold, 0.5 fold, 0.75 fold, 1 fold, 1.25 fold, 1.5 fold, 1.75 fold, 2 fold, 2.5 fold, 3 fold, 4 fold, 5 fold, or 10 fold more than) the compound alters the level of association of a second macromolecule with a reference condensate as compared to a reference level. In some embodiments, the first reference level is a level of association of the first macromolecule with the one or more target condensates determined in the absence of the compound. In some embodiments, the reference level is a level of association of the second macromolecule with the reference condensate determined in the absence of the compound. In some embodiments, the first macromolecule and the second macromolecule are the same. In some embodiments, the first macromolecule and the second macromolecule are different.

In some embodiments, the compound preferentially affects the level of association of the first macromolecule with the one or more target condensates in a target cell or tissue type if the compound alters the level of association of the first macromolecule with the one or more target condensates in a target cell or tissue type as compared to a first reference level more than (such as at least about any of 0.25 fold, 0.5 fold, 0.75 fold, 1 fold, 1.25 fold, 1.5 fold, 1.75 fold, 2 fold, 2.5 fold, 3 fold, 4 fold, 5 fold, or 10 fold more than) the compound alters the level of association of the first macromolecule with the one or more target condensates in a reference cell or tissue type as compared to a reference level. In some embodiments, the first reference level is a level of association of the first macromolecule with the one or more target condensates in the target cell or tissue type determined in the absence of the compound. In some embodiments, the reference level is a level of association of the first macromolecule with the one or more target condensates in the reference cell or tissue type determined in the absence of the compound.

In some embodiments, the level is an absolute amount. In some embodiments, the level is a relative level, such as 1) the amount of the macromolecule compared to the amount of another component of the one or more (target or reference) condensates, 2) the amount of the macromolecule associated with the one or more (target or reference) condensates compared to the amount of the macromolecule in the cell or another cellular component, such as another condensate or in an organelle, or 3) the amount of the macromolecule associated with the one or more (target or reference) condensates in one tissue or cell type compared the amount of the macromolecule associated with the one or more (target or reference) condensates in another tissue or cell type.

In some embodiments, the reference is an experimental control. In some embodiments, the reference level of a macromolecule is the level of association of the macromolecule with one or more reference condensates. In some embodiments, the one or more target condensates and the one or more reference condensates are located in different portions of the cellular composition. In some embodiments, the one or more target condensates and the one or more reference condensates are located in different portions of a cell. In some embodiments, the one or more target condensates and the one or more reference condensates are located in different cellular compositions. In some embodiments, the cellular composition that comprises the one or more target condensates is a first cellular composition, and the reference level is determined in a second cellular composition. In some embodiments, the reference level is a level of association of a macromolecule with the one or more target condensates or one or more reference condensates in a cellular composition that has not contacted the compound.

In some embodiments, the reference level is determined in a manner such that a meaningful result can be assessed for the compound. For example, in some embodiments, the reference level is determined in a reference cellular composition, wherein the reference cellular composition is prepared in a similar manner as the cellular composition contacted with the compound, except the reference cellular composition is not subjected to the compound or the step of contacting with the compound.

Provided herein are methods of identifying a compound comprising: (a) contacting a first cellular composition with a compound, wherein (i) the first cellular composition comprises a first set of one or more target condensates; and/or (ii) the first set of one or more target condensates form simultaneously with and/or after contacting the first cellular composition with the compound; (b) determining the level of association of the first macromolecule with the first set of one or more target condensates and a level of association of at least one additional macromolecule with the first set of one or more target condensates; (c) contacting a second cellular composition with the compound, wherein (i) the second cellular composition comprises a second set of one or more target condensates; and/or (ii) the second set of one or more target condensates form simultaneously with and/or after contacting the second cellular composition with the compound; and (d) determining the level of association of the first macromolecule with the second set of one or more target condensates and a level of association of a second macromolecule with the second set of one or more target condensates. In some embodiments, the second macromolecule and the first macromolecule are different. In some embodiments, the second macromolecule is one or more of the at least one additional macromolecule.

Also provided herein are methods of identifying a compound comprising: (a) contacting a cellular composition with a compound, wherein (i) the cellular composition comprises a first set of one or more target condensates and/or a second set of one or more target condensates; and/or (ii) the first set and or second set of one or more target condensates form simultaneously with and/or after contacting the cellular composition with the compound; (b) determining the level of association of the first macromolecule with the first set of one or more target condensates and a level of association of at least one additional macromolecule with the first set of one or more target condensates; (c) determining the level of association of the first macromolecule with the second set of one or more target condensates and a level of association of a second macromolecule with the second set of one or more target condensates. In some embodiments, the second macromolecule and the first macromolecule are different. In some embodiments, the second macromolecule is one or more of the at least one additional macromolecule.

In some embodiments, the macromolecule described herein is the first macromolecule. In some embodiments, the macromolecule is not the first macromolecule. In some embodiments, the macromolecule is one or more of the at least one additional macromolecule. In some embodiments, the macromolecule is a reference macromolecule (e.g., a macromolecule known to be associated with a target condensate, or known not to be associated with a target condensate under healthy or non-stressed condition or cell/tissue type). In some embodiments, the macromolecule is the first macromolecule, and the method further comprises determining the level of association of a second macromolecule with the second set of one or more target condensates. In some embodiments, the second macromolecule and the first macromolecule are different. In some embodiments, the second macromolecule is one or more of the at least one additional macromolecule.

In some embodiments, the method is a method of identifying a compound that preferentially affects the level of association of a first macromolecule with the first set of one or more target condensates. In some embodiments, the method is a method of identifying a compound that preferentially increases a level of association of a first macromolecule with the first set of one or more target condensates. In some embodiments, the method is a method of identifying a compound that preferentially decreases a level of association of a first macromolecule with the first set of one or more target condensates. In some embodiments, the method is a method of identifying a compound useful for treating a disease in an individual in need thereof, wherein the first set of one or more target condensates is associated with the disease. In some embodiments, the disease is a neurodegenerative, proliferative, immunological, cardiac, or metabolic disease.

In some embodiments, the method is a method of identifying a plurality of compounds that preferentially affect the level of association of a first macromolecule with the first set of one or more target condensates, the method comprising performing any of the methods described herein for a plurality of compounds. In some embodiments, the method is a method of identifying a plurality of compounds that preferentially increase a level of association of a first macromolecule with the first set of one or more target condensates, the method comprising performing any of the methods described herein for a plurality of compounds. In some embodiments, the method is a method of identifying a plurality of compounds that preferentially decrease a level of association of a first macromolecule with the first set of one or more target condensates, the method comprising performing any of the methods described herein for a plurality of compounds. In some embodiments, the method is a method of identifying a plurality of compounds useful for treating a disease in an individual in need thereof, wherein the first set of one or more target condensates is associated with the disease, the method comprising performing any of the methods described herein of the method for a plurality of compounds. In some embodiments, the disease is a neurodegenerative, proliferative, immunological, cardiac, or metabolic disease.

In some embodiments, the compound preferentially affects the level of association of the first macromolecule with the first set of one or more target condensates if the compound affects the level of association of the first macromolecule with the first set of one or more target condensates more than the compound affects the level of association of the first macromolecule with the second set of one or more target condensates. In some embodiments, the compound does not affect the level of association of the first macromolecule with the second set of one or more target condensates. In some embodiments, the compound preferentially increases the level of association of the first macromolecule with the first set of one or more target condensates if the compound increases the level of association of the first macromolecule with the first set of one or more target condensates more than the compound increases the level of association of the first macromolecule with the second set of one or more target condensates. In some embodiments, the compound does not increase the level of association of the first macromolecule with the second set of one or more target condensates. In some embodiments, the compound preferentially decreases the level of association of the first macromolecule with the first set of one or more target condensates if the compound decreases the level of association of the first macromolecule with the first set of one or more target condensates more than the compound decreases the level of association of the first macromolecule with the second set of one or more target condensates. In some embodiments, the compound does not decrease the level of association of the first macromolecule with the second set of one or more target condensates.

Also provided herein are methods of identifying a compound comprising (a) contacting a cellular composition with a compound, wherein (i) the cellular composition comprises one or more target condensates; and/or (ii) the one or more target condensates form simultaneously with and/or after contacting the cellular composition with the compound; and (b) determining if a first macromolecule and at least one additional macromolecule are associated with the one or more target condensates. In some embodiments, the method is a method of identifying a compound that causes a first macromolecule to associate or disassociate with one or more target condensates. In some embodiments, the method is a method of identifying a compound that causes a first macromolecule to associate with one or more target condensates. In some embodiments, the method is a method of identifying a compound that causes a first macromolecule to disassociate with one or more target condensates. In some embodiments, the method is a method of identifying a compound that preferentially causes a first macromolecule to associate or disassociate with one or more target condensates. In some embodiments, the method is a method of identifying a compound that preferentially causes a first macromolecule to associate with one or more target condensates. In some embodiments, the method is a method of identifying a compound that preferentially causes a first macromolecule to disassociate with one or more target condensates. In some embodiments, the method is a method of identifying a compound useful for treating a disease in an individual in need thereof, wherein the one or more target condensates is associated with the disease. In some embodiments, the disease is a neurodegenerative, proliferative, immunological, cardiac, or metabolic disease.

Also provided herein are methods of identifying a plurality of compounds comprising (a) contacting a cellular composition with a compound, wherein (i) the cellular composition comprises one or more target condensates; and/or (ii) the one or more target condensates form simultaneously with and/or after contacting the cellular composition with the compound; (b) determining if a first macromolecule and at least one additional macromolecule are associated with the one or more target condensates, and (c) performing steps (a) and (b) for a plurality of compounds. In some embodiments, the method is a method of identifying a plurality of compounds that causes a first macromolecule to associate or disassociate with one or more target condensates. In some embodiments, the method is a method of identifying a plurality of compounds that causes a first macromolecule to associate with one or more target condensates. In some embodiments, the method is a method of identifying a plurality of compounds that causes a first macromolecule to disassociate with one or more target condensates. In some embodiments, the method is a method of identifying a plurality of compounds that preferentially causes a first macromolecule to associate or disassociate with one or more target condensates. In some embodiments, the method is a method of identifying a plurality of compounds that preferentially causes a first macromolecule to associate with one or more target condensates. In some embodiments, the method is a method of identifying a plurality of compounds that preferentially causes a first macromolecule to disassociate with one or more target condensates. In some embodiments, the method is a method of identifying a plurality of compounds useful for treating a disease in an individual in need thereof, wherein the one or more target condensates is associated with the disease. In some embodiments, the disease is a neurodegenerative, proliferative, immunological, cardiac, or metabolic disease.

In some embodiments, the method further comprises identifying a characteristic that a subset or all of the identified compounds have in common in addition to the ability to preferentially cause the first macromolecule to associate or disassociate with one or more target condensates. In some embodiments, the method further comprises identifying a characteristic that a subset or all of the identified compounds have in common in addition to the ability to preferentially cause the first macromolecule to associate with one or more target condensates. In some embodiments, the method further comprises identifying a characteristic that a subset or all of the identified compounds have in common in addition to the ability to preferentially cause the first macromolecule to disassociate with one or more target condensates. In some embodiments, the method further comprises performing step (a) contacting a cellular composition with a compound, wherein (i) the cellular composition comprises one or more target condensates; and/or (ii) the one or more target condensates form simultaneously with and/or after contacting the cellular composition with the compound and step (b) determining if a first macromolecule and at least one additional macromolecule are associated with the one or more target condensates for one or more additional test compounds that comprise the identified characteristic. In some embodiments, the method further comprises performing steps (a) and (b) for one or more additional test compounds that do not comprise the identified characteristic.

In some embodiments, the compound causes the first macromolecule to associate with the one or more target condensates. In some embodiments, the compound does not cause the first macromolecule to associate with the one or more target condensates. In some embodiments, the compound causes the first macromolecule not to associate with the one or more target condensates. In some embodiments, the compound does not cause the first macromolecule not to associate with the one or more target condensates.

In some embodiments, the compound causes one or more of the at least one additional macromolecule to associate with the one or more target condensates. In some embodiments, the compound causes each additional macromolecule to associate with the one or more target condensates. In some embodiments, the compound does not cause one or more of the at least one additional macromolecule to associate with the one or more target condensates. In some embodiments, the compound does not cause each additional macromolecule to associate with the one or more target condensates. In some embodiments, the compound does not cause one or more of the at least one additional macromolecule not to associate with the one or more target condensates. In some embodiments, the compound does not cause each additional macromolecule not to associate with the one or more target condensates.

In some embodiments, the first macromolecule would be associated with the one or more target condensates in the absence of the compound. In some embodiments, the first macromolecule would not be associated with the one or more target condensates in the absence of the compound. In some embodiments, one or more of the at least one additional macromolecule would be associated with the one or more target condensates in the absence of the compound. In some embodiments, each additional macromolecule would be associated with the one or more target condensates in the absence of the compound. In some embodiments, one or more of the at least one additional macromolecule would not be associated with the one or more target condensates in the absence of the compound. In some embodiments, each additional macromolecule would not be associated with the one or more target condensates in the absence of the compound. In some embodiments, the first macromolecule and one or more of the at least one additional macromolecule would be associated with the one or more target condensates in the absence of the compound. In some embodiments, the first macromolecule and each additional macromolecule would be associated with the one or more target condensates in the absence of the compound. In some embodiments, the first macromolecule and one or more of the at least one additional macromolecule would not be associated with the one or more target condensates in the absence of the compound. In some embodiments, the first macromolecule and each additional macromolecule would not be associated with the one or more target condensates in the absence of the compound.

In some embodiments, one or more of the at least one additional macromolecule is associated with the one or more target condensates in the presence of the compound and would be associated with the one or more target condensates in the absence of the compound. In some embodiments, each additional macromolecule is associated with the one or more target condensates in the presence of the compound and would be associated with the one or more target condensates in the absence of the compound. In some embodiments, one or more of the at least one additional macromolecule is not associated with the one or more target condensates in the presence of the compound and would not be associated with the one or more target condensates in the absence of the compound. In some embodiments, each additional macromolecule is not associated with the one or more target condensates in the presence of the compound and would not be associated with the one or more target condensates in the absence of the compound.

In some embodiments, the compound preferentially causes the first macromolecule to associate with the one or more target condensates if: (1) the compound causes the first macromolecule to associate with the one or more target condensates; (2) the compound does not cause each (or at least one) additional macromolecule to associate with the one or more target condensates (or causes less association of each (or at least one) additional macromolecule with the one or more target condensates); and (3) the first macromolecule would not be associated with the one or more target condensates in the absence of the compound. In some embodiments, the compound preferentially causes the first macromolecule to associate with the one or more target condensates if: (1) the compound causes the first macromolecule to associate with the one or more target condensates; (2) the compound does not cause each (or at least one) additional macromolecule to associate with the one or more target condensates (or causes less association of each (or at least one) additional macromolecule with the one or more target condensates); and (3) the first macromolecule and one or more of the at least one additional macromolecule would not be associated with the one or more target condensates in the absence of the compound. In some embodiments, the compound preferentially causes the first macromolecule to associate with the one or more target condensates if: (1) the compound causes the first macromolecule to associate with the one or more target condensates; (2) the compound does not cause each (or at least one) additional macromolecule to associate with the one or more target condensates (or causes less association of each (or at least one) additional macromolecule with the one or more target condensates); and (3) the first macromolecule and each additional macromolecule would not be associated with the one or more target condensates in the absence of the compound.

In some embodiments, the compound preferentially causes the first macromolecule to disassociate with the one or more target condensates if: (1) the compound causes the first macromolecule not to associate with the one or more target condensates; (2) the compound does not cause each (or at least one) additional macromolecule not to associate with the one or more target condensates (or causes less disassociation of each (or at least one) additional macromolecule with the one or more target condensates); and (3) the first macromolecule would be associated with the one or more target condensates in the absence of the compound. In some embodiments, the compound preferentially causes the first macromolecule to disassociate with the one or more target condensates if: (1) the compound causes the first macromolecule not to associate with the one or more target condensates; (2) the compound does not cause each (or at least one) additional macromolecule not to associate with the one or more target condensates (or causes less disassociation of each (or at least one) additional macromolecule with the one or more target condensates); and (3) the first macromolecule and one or more of the at least one additional macromolecule would be associated with the one or more target condensates in the absence of the compound. In some embodiments, the compound preferentially causes the first macromolecule to disassociate with the one or more target condensates if: (1) the compound causes the first macromolecule not to associate with the one or more target condensates; (2) the compound does not cause each (or at least one) additional macromolecule not to associate with the one or more target condensates (or causes less disassociation of each (or at least one) additional macromolecule with the one or more target condensates); and (3) the first macromolecule and each additional macromolecule would be associated with the one or more target condensates in the absence of the compound.

In some embodiments, the compound directly causes the first macromolecule to associate with the one or more target condensates. In some embodiment, the compound indirectly causes the first macromolecule to associate with the one or more target condensates. In some embodiments, the compound directly causes the first macromolecule not to associate with the one or more target condensates. In some embodiment, the compound indirectly causes the first macromolecule not to associate with the one or more target condensates.

In some embodiments, the compound directly causes one or more of the at least one additional macromolecule to associate with the one or more target condensates. In some embodiment, the compound indirectly causes one or more of the at least one additional macromolecule to associate with the one or more target condensates. In some embodiments, the compound directly causes one or more of the at least one additional macromolecule not to associate with the one or more target condensates. In some embodiment, the compound indirectly causes one or more of the at least one additional macromolecule not to associate with the one or more target condensates.

In some embodiments, the compound directly causes each additional macromolecule to associate with the one or more target condensates. In some embodiment, the compound indirectly causes each additional macromolecule to associate with the one or more target condensates. In some embodiments, the compound directly causes each additional macromolecule not to associate with the one or more target condensates. In some embodiment, the compound indirectly causes each additional macromolecule not to associate with the one or more target condensates.

In some embodiments, the compound causes a macromolecule, such as a first macromolecule or an additional macromolecule, to associate with one or more target condensates if the macromolecule is determined to be associated with the one or more target condensates after contacting the cellular composition with the compound, and the macromolecule is determined not to be associated with one or more reference condensates. In some embodiments, the one or more reference condensates are an experimental control. In some embodiments, the one or more target condensates and the one or more reference condensates are located in different portions of the cellular composition. In some embodiments, the one or more target condensates and the one or more reference condensates are located in different portions of a cell. In some embodiments, the one or more target condensates and the one or more reference condensates are located in different cellular compositions. In some embodiments, the cellular composition that comprises the one or more target condensates is a first cellular composition, and the one or more reference condensates are in a second cellular composition. In some embodiments, the second cellular composition has not contacted the compound.

In some embodiments, the determination of the association of the macromolecule with the one or more reference condensates is performed in a manner such that a meaningful result can be assessed for the compound. For example, in some embodiments, the determination of the association of the macromolecule with the one or more reference condensates is performed in a reference cellular composition, wherein the reference cellular composition is prepared in a similar manner as the cellular composition contacted with the compound, except the reference cellular composition is not subjected to the compound or the step of contacting with the compound.

In some embodiments, the compound causes a macromolecule, such as a first macromolecule or an additional macromolecule, to associate with one or more target condensates if the macromolecule is determined to be associated with the one or more target condensates after contacting the cellular composition with the compound, and the macromolecule would not be associated with the one or more target condensates in the absence of contacting the cellular composition with the compound. In some embodiments, the method further comprises determining if the macromolecule is associated with the one or more target condensates in the absence of the compound. In some embodiments, the compound causes a macromolecule, such as a first macromolecule or an additional macromolecule, to associate with one or more target condensates if the macromolecule is determined to be associated with the one or more target condensates after contacting the cellular composition with the compound, and the macromolecule is not associated with one or more reference condensates. In some embodiments, the method further comprises determining if the macromolecule is associated with the one or more reference condensates in the absence of the compound.

Also provided herein are methods of identifying a compound comprising (a) contacting a first cellular composition with a compound, wherein (i) the first cellular composition comprises a first set of one or more target condensates; and/or (ii) the first set of one or more target condensates form simultaneously with and/or after contacting the first cellular composition with the compound; (b) determining if a first macromolecule and at least one additional macromolecule are associated with the first set of one or more target condensates; (c) contacting a second cellular composition with a compound, wherein (i) the second cellular composition comprises a second set of one or more target condensates; and/or (ii) the second set of one or more target condensates form simultaneously with and/or after contacting the second cellular composition with the compound; and (d) determining if a second macromolecule is associated with the second set of one or more target condensates. In some embodiments, the second macromolecule and the first macromolecule are the same. In some embodiments, the second macromolecule and the first macromolecule are different. In some embodiments, the second macromolecule is one or more of the at least one additional macromolecule. In some embodiments, the second macromolecule is a reference macromolecule (e.g., a macromolecule known to be associated with a target condensate, or known not to be associated with a target condensate under healthy or non-stressed condition or cell/tissue type). In some embodiments, the second macromolecule and the first macromolecule are the same, and the method further comprises determining if a third macromolecule (e.g., different from the first and the second macromolecule) is associated with the second set of one or more target condensates. In some embodiments, the third macromolecule is one or more of the at least one additional macromolecule.

Also provided herein are methods of identifying a compound comprising (a) contacting a cellular composition with a compound, wherein (i) the cellular composition comprises a first set of one or more target condensates and/or a second set of one or more target condensates; and/or (ii) the first set and/or the second set of one or more target condensates form simultaneously with and/or after contacting the cellular composition with the compound; and (b) determining if a first macromolecule and at least one additional macromolecule are associated with the first set of one or more target condensates; (c) determining if a second macromolecule is associated with the second set of one or more target condensates. In some embodiments, the second macromolecule and the first macromolecule are the same. In some embodiments, the second macromolecule and the first macromolecule are different. In some embodiments, the second macromolecule is one or more of the at least one additional macromolecule. In some embodiments, the second macromolecule is a reference macromolecule (e.g., a macromolecule known to be associated with a target condensate, or known not to be associated with a target condensate under healthy or non-stressed condition or cell/tissue type). In some embodiments, the second macromolecule and the first macromolecule are the same, and the method further comprises determining if a third macromolecule (e.g., different from the first and the second macromolecule) is associated with the second set of one or more target condensates. In some embodiments, the third macromolecule is one or more of the at least one additional macromolecule.

In some embodiments, the method is a method of identifying a compound that causes a first macromolecule to associate with the first set of one or more target condensates. In some embodiments, the method is a method of identifying a compound that causes a first macromolecule to disassociate with the first set of one or more target condensates. In some embodiments, the method is a method of identifying a compound that preferentially causes a first macromolecule to associate or disassociate with the first set of one or more target condensates. In some embodiments, the method is a method of identifying a compound that preferentially causes a first macromolecule to associate with the first set of one or more target condensates. In some embodiments, the method is a method of identifying a compound that preferentially causes a first macromolecule to disassociate with the first set of one or more target condensates. In some embodiments, the method is a method of identifying a compound useful for treating a disease in an individual in need thereof, wherein the first set of one or more target condensates is associated with the disease. In some embodiments, the disease is a neurodegenerative, proliferative, immunological, cardiac, or metabolic disease.

In some embodiments, the method is a method of identifying a plurality of compounds that cause a first macromolecule to associate with the first set of one or more target condensates, the method comprising performing any of the methods described herein for a plurality of compounds. In some embodiments, the method is a method of identifying a plurality of compounds that cause a first macromolecule to disassociate with the first set of one or more target condensates, the method comprising performing any of the methods described herein for a plurality of compounds. In some embodiments, the method is a method of identifying a plurality of compounds that preferentially cause a first macromolecule to associate or disassociate with the first set of one or more target condensates, the method comprising performing any of the methods described herein for a plurality of compounds. In some embodiments, the method is a method of identifying a plurality of compounds that preferentially cause a first macromolecule to associate with the first set of one or more target condensates, the method comprising performing any of the methods described herein for a plurality of compounds. In some embodiments, the method is a method of identifying a plurality of compounds that preferentially cause a first macromolecule to disassociate with the first set of one or more target condensates, the method comprising performing any of the methods described herein for a plurality of compounds. In some embodiments, the method is a method of identifying a plurality of compounds useful for treating a disease in an individual in need thereof, wherein the first set of one or more target condensates is associated with the disease, the method comprising performing any of the methods described herein for a plurality of compounds. In some embodiments, the disease is a neurodegenerative, proliferative, immunological, cardiac, or metabolic disease, the method comprising performing any of the methods described herein for a plurality of compounds.

In some embodiments, the compound preferentially causes the first macromolecule to associate with the first set of one or more target condensates if the compound causes the first macromolecule to associate with the first set of one or more target condensates more than the compound causes the first macromolecule to associate with the second set of one or more target condensates. In some embodiments, the compound preferentially causes the first macromolecule to disassociate with the first set of one or more target condensates if the compound causes the first macromolecule to disassociate with the first set of one or more target condensates more than the compound causes the first macromolecule to disassociate with the second set of one or more target condensates.

One of ordinary skill in the art will readily recognize that cellular processes, including the state of a condensate and components thereof, are dynamic. The methods described herein thus may encompass contacting a cell with a compound at any point in the life cycle (e.g., various mitosis phases or non-mitosis phase) of the one or more target condensates or components thereof. For example, the methods may encompass, e.g., contacting a cellular composition with a compound when the one or more target condensates are in any location of the cell, are present in any quantity, including being absent, are undergoing a morphological change, such as a change in size or liquidity, or are changing in composition. In some aspects, the methods may also encompass contacting a cellular composition with a compound when a component of the one or more target condensate is in any location of the cell, in any quantity, or has any post-translation modification status.

Compounds

In some embodiments, the compound is a small molecule, a polypeptide, a lipid, or a nucleic acid. In some embodiments, the compound is an approved compound, such as a compound approved for medical treatment by the United States Food and Drug Administration. In some embodiments, the compound is a novel compound. In some embodiments, the compound is a small molecule. In some embodiments, the small molecule is an alkaloid, a glycoside, a phenazine, a phenol, a polyketide, a terpene, or a tetrapyrrole. In some embodiments, test compound is a nucleic acid. In some embodiments, the compound is a siRNA, miRNA, or mRNA. In some embodiments, the compound is a non-naturally occurring compound. In some embodiments, the compound has a molecular weight of less than about 1,000 Da, such as about 500 Da or less. In some embodiments, the compound satisfies Lipinski's rule of five. In some embodiments, the compound is a small molecule (such as a therapeutic small molecule that is about 1,000 Da or less and/or satisfies Lipinski's rule of five). In some embodiments, the compound comprises a detectable characteristic, such as fluorescent characteristic. In some embodiments, the compound comprises a label, such as a fluorescent label. In some embodiments, the compound is further labeled with a detection tag, such as a fluorescein, a fluorescent polypeptide, or a radioisotope label. In some embodiments, the tag does not affect the compound's action and/or activity in preferentially causing association/dissociation of the first macromolecule (or a reference macromolecule) with the one or more target condensates (or a reference condensate). In some embodiments, the label is detectable using a microscopy technique, e.g., a fluorescent microscopy technique.

In some embodiments, the methods herein comprise adding two or more compounds. Accordingly, in some embodiments, provided herein are methods of identifying a combination of compounds that preferentially alter, such as preferentially increase or preferentially decrease, a level of association of a first macromolecule with one or more target condensates or that preferentially cause a first macromolecule to associate or disassociate with one or more target condensates. In some embodiments, the two or more compounds are each selected from any of a small molecule, a polypeptide, a lipid, or a nucleic acid. In some embodiments, the two or more test compounds are added sequentially or simultaneously. In some embodiments, the two or more test compounds are fused together.

Cellular Compositions

Cellular compositions, as disclosed herein, are compositions comprising at least one cell. In some embodiments, the cellular composition comprises a single cell. In some embodiments, the cellular composition comprises at least two, three, four, five, 10, 25, 50, 100, 500, 1000 or more cells. Cellular compositions can be obtained from various different sources, such as in vivo sources, such as a bodily fluid or tissue sample from an animal, or in vitro sources, such as from cultured cells or cultured tissues. Bodily fluid and tissue samples often contain multiple cell types, for example brain tissue may comprise neurons, glial cells, and many other types of cells. Accordingly, in some embodiments, the cellular composition comprises at least two, three, four, or five cell types. Cellular compositions may also comprise media, such as cell culture media. The media may vary depending upon the sample and cell type used. In some embodiments, the cellular composition comprises one or more of: amino acids, vitamins, inorganic salts, glucose, serum, growth factors, hormones, and attachment factors. Exemplary media include Ames' Medium, BGJb Medium with or without the Fitton-Jackson Modification, Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, Dulbecco's Modified Eagle Medium (DMEM) and Eagle's Minimum Essential Medium (EMEM).

For methods that require a first cellular composition and a second cellular composition, any cellular composition disclosed herein may be used. In some embodiments, the first cellular composition and the second cellular composition comprise substantially similar components. For example, the first cellular composition and the second cellular composition may each be samples from a source cellular composition or be each be prepared by combining the same components using the same method. In some embodiments, the first cellular composition and the second cellular composition comprise substantially distinct components. For example, the first cellular composition and the second cellular composition may each be samples from different source cellular compositions or each be prepared by combining different components, such as different cells or media or using components that were prepared using different methods. In some embodiments, the first cellular composition comprise healthy or non-stressed cells or cells expressing a wild type macromolecule, and the second cellular composition comprise diseased (e.g., tumor cells) or stressed cells or cells expressing a mutant macromolecule.

In some embodiments, the cell is a microorganism or an animal cell. In some embodiments, the cell is an animal cell. In some embodiments, the cell is a human cell. In some embodiments, the cell has one or more features of a neurodegenerative, proliferative, immunological, cardiac, or metabolic disease. In some embodiments, the cell is a HeLa cell, a HEK293 cell, an induced pluripotent stem cell (iPSC cell), a cardiomyocyte, a myocyte, a stem cell-derived cell, a neuron, a cancer cell, an immune cell, or an adipocyte. In some embodiments, the cell is a neuron. In some embodiments, the cell is a cancer cell. In some embodiments, the cell is an immune cell. In some embodiments, the cell is an induced pluripotent stem cell (iPS cell), a HeLa cell, or an HEK293 cell. When describing a specific type of cell, it is understood to include cells derived from that type of cell unless explicitly stated otherwise. For example, a HeLa cell comprising a heterologous transgene would be considered a HeLa cell unless explicitly stated otherwise.

In some embodiments, the cell comprises a condensate that is determined to be dysregulated. In some embodiments, the cell comprises a mutation associated with a disease. In some embodiments, the cell has one or more features of a neurodegenerative, proliferative, immunological, cardiac, or metabolic disease. In some embodiments, the cell has been treated with arsenate, a temperature change, or a pH change.

In some embodiments, the method comprises altering the temperature of cellular composition, such as exposing the cellular composition to lower or higher temperatures; altering the salt content of the cellular composition; adding or changing a buffer in the cellular composition; altering the pH of the cellular composition; or adding a crowding agent to the cellular composition, such as PEG or dextran to the cellular composition.

In some embodiments, a cell in the cellular composition comprises a mutation that causes the one or more target condensates to form and/or modifies the one or more target condensates. In some embodiments, the mutation modifies one or more of the following: the size of the one or more target condensates, the shape (e.g., sphericity) of the one or more target condensates, the surface area of the one or more target condensates, the concentration of one or more components of the one or more target condensates, the location of the one or more target condensates, the number of the one or more target condensates, the ratio of the amount of one or more target condensates and a reference condensate, the functional activity associated with the one or more target condensates, the composition of the one or more target condensates, the co-localization of the one or more target condensates with a biomolecule, the diffusion coefficient of a component of the one or more target condensates, the stability of the one or more target condensates, the dissolution or reduction in size of the one or more target condensates, the liquidity of the one or more target condensates, the solidification of the one or more target condensates, the location of a condensate component, the amount of a condensate component or a precursor thereof, condensate partitioning of a biomolecule into the one or more target condensates, the a functional activity associated with a condensate component, the aggregation of a condensate component, post-translational modification status of a condensate component, the amount of a degradation product of a condensate component, and the heterogeneous distribution of components within the one or more target condensates. In some embodiments, a cell in the cellular composition comprises a mutation that causes the condensate to form.

In some embodiments, the cell expresses a protein that is labeled with a fluorescent protein. In some embodiments, the protein is a protein known to concentrate in the one or more target condensates. In some embodiments, the cell expresses a first protein and a second protein, wherein the first protein is labeled with a first label, wherein the first protein is known to concentrate in a first set of one or more target condensates, wherein the second protein is labeled with a second label, wherein the second protein is known to concentrate in a second set of one or more target condensates, and wherein the first label and the second label are distinguishable. In some embodiments, the cell expresses a first protein and a second protein, wherein the first protein is labeled with a first fluorescent protein, wherein the first protein is known to concentrate in a first set of one or more target condensates, wherein the second protein is labeled with a second fluorescent protein, wherein the second protein is known to concentrate in a second set of one or more target condensates, and wherein the first fluorescent protein and second fluorescent protein are distinguishable. In some embodiments, the expression of the protein is induced or conditional, e.g., using a TetOn system. In some embodiments, the expression of the protein is constitutive.

Condensates

In some embodiments, the one or more target condensates are 2 or more, 3 or more, 4 or more, 5 or more, 6 or more, 7 or more, 8 or more, 9 or more, 10 or more target condensates, 25 or more, 50 or more, 75 or more, or 100 or more target condensates. In some embodiments, the one or more target condensates are about 1-1000 condensates, such as about any of 1-750, 1-500, 1-250, 1-100, 10-500, 10-50, 10-20, 25-1000, 25-500, 25-250, 100-1000, or 100-500 condensates. In some embodiments, the one or more target condensates is a single condensate type, e.g., a condensate type that contains a common macromolecule component. In some embodiments, the one or more target condensates is a plurality of condensates types, e.g., certain of the plurality of condensates contains a first macromolecule component and the certain of the plurality of condensates does not contain the first macromolecule component. In some embodiments, the one or more reference condensates are 2 or more, 3 or more, 4 or more, 5 or more, 6 or more, 7 or more, 8 or more, 9 or more, 10 or more reference condensates, 25 or more, 50 or more, 75 or more, or 100 or more reference condensates. In some embodiments, the one or more reference condensates are about any of 1-1000 condensates, such as 1-750. 1-500. 1-250, 1-100, 10-500, 10-50, 10-20, 25-1000, 25-500, 25-250, 100-1000, or 100-500 condensates. In some embodiments, the one or more reference condensates is a single condensate type, e.g., a condensate type that contains a common macromolecule component. In some embodiments, the one or more reference condensates is a plurality of condensates types, e.g., certain of the plurality of condensates contains a first macromolecule component and the certain of the plurality of condensates does not contain the first macromolecule component. In some embodiments, the one or more reference condensates and the one or more target condensates do not contain a common macromolecule component. In some embodiments, the one or more reference condensates and the one or more target condensates contain a common macromolecule component.

Many condensates are well known in the art and many condensates can be identified or analyzed using known methods (see Basturea, G. N. ("Biological Condensates," MATER METHODS 2019; 9:2794) for exemplary methods), such as microscopy. In some embodiments, the methods further comprise identifying the one or more target condensates. In some embodiments, the methods further comprise identifying the one or more reference condensates. In some embodiments, the one or more target condensates are cellular condensates. In some embodiments, the one or more reference condensates are cellular condensates. In some embodiments, the one or more reference condensates are in vitro condensates. Numerous cellular condensates have been described and numerous more are known to form, but have not yet been described or named. In some embodiments, the one or more target condensates are cytoplasmic condensates. In some embodiments, the one or more target condensates are nuclear condensates. In some embodiments, the one or more cellular condensates are cleavage bodies, p-granules, histone locus bodies, multivesicular bodies, neuronal RNA granules, nuclear gems, nuclear pores, nuclear speckles, nuclear stress bodies, nucleoli, Oct1/PTF/transcription (OPT) domains, paraspeckles, perinucleolar compartments, PML nuclear bodies, PML oncogenic domains, polycomb bodies, processing bodies, Sam68 nuclear bodies, stress granules, or splicing speckles. In some embodiments, the one or more cellular condensates are not stress granules.

In some embodiments, the one or more target condensates is a plurality of condensates. In some embodiments, the plurality of target condensates is all or a subset of a class of condensates in a portion of the cellular composition. In some embodiments, the plurality of target condensates is all or a subset of a class of condensates in a cell in the cellular composition. In some embodiments, the plurality of target condensates is all or a subset of a class of condensates in a portion of a cell in the cellular composition. In some embodiments, the one or more reference condensates is a plurality of condensates. In some embodiments, the plurality of reference condensates is all or a subset of a class of condensates in a portion of the cellular composition. In some embodiments, the plurality of reference condensates is all or a subset of a class of condensates in a cell in the cellular composition. In some embodiments, the plurality of reference condensates is all or a subset of a class of condensates in a portion of a cell in the cellular composition. In some embodiments, the plurality of reference condensates is all or a subset of a class of condensates in an in vitro condensate system.

In some embodiments, the portion of the cell is the cytoplasm, the nucleus, an organelle, or a non-membrane bound compartment. In some embodiments, the class of condensates comprises condensates which comprise a specific macromolecule. In some embodiments, the class of condensates comprises condensates which are cleavage bodies; the class of condensates comprises condensates which are p-granules; the class of condensates comprises condensates which are histone locus bodies; the class of condensates comprises condensates which are multivesicular bodies; the class of condensates comprises condensates which are neuronal RNA granules; the class of condensates comprises condensates which are nuclear gems; the class of condensates comprises condensates which are nuclear pores; the class of condensates comprises condensates which are nuclear speckles; the class of condensates comprises condensates which are nuclear stress bodies; the class of condensates comprises condensates which are nucleoli; the class of condensates comprises condensates which are Oct1/PTF/transcription (OPT) domains; the class of condensates comprises condensates which are paraspeckles; the class of condensates comprises condensates which are perinucleolar compartments; the class of condensates comprises condensates which are PML nuclear bodies; the class of condensates comprises condensates which are PML oncogenic domains; the class of condensates comprises condensates which are polycomb bodies; the class of condensates comprises condensates which are processing bodies; the class of condensates comprises condensates which are Sam68 nuclear bodies; the class of condensates comprises condensates which are stress granules; or the class of condensates comprises condensates which are splicing speckles.

In some embodiments, the one or more target condensates and the one or more reference condensates are the same class (or type) of condensate. For example, the one or more target condensates and the one or more reference condensates may comprise one or more of the same macromolecules, may form under the same conditions, may have the same response to a stimuli, may form in the same cell/tissue type, and/or may be present in the same location within cells. In some embodiments, the one or more target condensates and the one or more reference condensates comprise one or more of the same macromolecules and are present in the same location within cells. In some embodiments, the class of condensates comprises condensates which are cleavage bodies; the class of condensates comprises condensates which are p-granules; the class of condensates comprises condensates which are histone locus bodies; the class of condensates comprises condensates which are multivesicular bodies; the class of condensates comprises condensates which are neuronal RNA granules; the class of condensates comprises condensates which are nuclear gems; the class of condensates comprises condensates which are nuclear pores; the class of condensates comprises condensates which are nuclear speckles; the class of condensates comprises condensates which are nuclear stress bodies; the class of condensates comprises condensates which are nucleoli; the class of condensates comprises condensates which are Oct1/PTF/transcription (OPT) domains; the class of condensates comprises condensates which are paraspeckles; the class of condensates comprises condensates which are perinucleolar compartments; the class of condensates comprises condensates which are PML nuclear bodies; the class of condensates comprises condensates which are PML oncogenic domains; the class of condensates comprises condensates which are polycomb bodies; the class of condensates comprises condensates which are processing bodies; the class of condensates comprises condensates which are Sam68 nuclear bodies; the class of condensates comprises condensates which are stress granules; or the class of condensates comprises condensates which are splicing speckles.

In some embodiments, the one or more target condensates and the one or more reference condensates are different classes (or types) of condensate. For example, the one or more target condensates and the one or more reference condensates may comprise one or more different macromolecules, may form under different conditions, may have a different responses to a stimuli, may form in a different cell/tissue type, may have one or more different characteristics described herein (e.g., shape, liquidity, size, composition, etc.), and/or may be present in different locations within cells. In some embodiments, the one or more target condensates and the one or more reference condensates comprise one or more of the same macromolecules and are present in different locations within cells. In some embodiments, the one or more target condensates and the one or more reference condensates comprise one or more of the same macromolecules and comprise one or more different macromolecules. In some embodiments, the different macromolecules are variants. For example, in some embodiments, one macromolecule is a wild-type protein and the other macromolecule is a mutant protein. In some embodiments, one macromolecule is a mature form and the other macromolecule is a pre-mature form. In some embodiments, one macromolecule does not have post-translational modification and the other macromolecule has post-translational modification.

The dysregulation of various condensates can be associated with a disease. For example, based on cellular and cell-free condensate experiments, disease-associated mutations in the protein fused in sarcoma (FUS) have been shown to cause aberrant phase-separation behavior that contributes directly to development of the motor neuron disease, amyotrophic lateral sclerosis (ALS) (Naumann et al., 2018, Nat Commun, 9(1):335). Accordingly, in some embodiments dysregulation of the one or more target condensates is associated with a disease. In some embodiments, the disease is a neurodegenerative, proliferative, immunological, cardiac, or metabolic disease. In some embodiments, the dysregulation comprises an alteration in one or more of: amount of the one or more target condensates; composition of the one or more target condensates; location of the one or more target condensates; distribution of the one or more target condensates; size of the one or more target condensates; liquidity or solidification of the one or more target condensates; dissolution of the one or more target condensates; shape of the one or more target condensates; concentration of one or more components of one or more target condensates; distribution of one or more components of one or more target condensates; diffusion coefficient of one or more components of the one or more target condensates; post-translational modification of the one or more components of the one or more target condensates; and heterogeneous distribution of one or more components within the one or more target condensates, e.g. components located in the core instead of the shell of the condensate. In some embodiments, the alteration is compared to a similar non-dysregulated condensate.

In some embodiments, the one or more target condensates is a plurality of condensates. In some embodiments, the compound does not measurably alter one or more of: total number of the plurality of target condensates, size of the plurality of target condensates, shape of the plurality of target condensates, liquidity or solidification of plurality of target condensates, location of the plurality of target condensates, surface area of the plurality of target condensates, dissolution of the plurality of target condensates, post-translational modification of the one or more components of the plurality of target condensates, and heterogeneous distribution of one or more components within the plurality of target condensates.

In some embodiments, the one or more target or reference condensates is a single condensate, e.g., a single condensate type. In some embodiments, the compound does not measurably alter one or more characteristics selected from: number of the target and/or reference condensate, size of the target and/or reference condensate, location of the target and/or reference condensate, distribution of the target and/or reference condensate, surface area of the target and/or reference condensate, dissolution of the target and/or reference condensate, shape of the target and/or reference condensate, liquidity or solidification of the target and/or reference condensate, post-translational modification of the one or more components of the target and/or reference condensate, and heterogeneous distribution of one or more components within the target and/or reference condensate. In some embodiments, the one or more target or reference condensates is a plurality of condensates, e.g., a plurality of condensate types. In some embodiments, the compound does not measurably alter one or more characteristics selected from: number of the plurality of target and/or reference condensates, size of the plurality of target and/or reference condensates, location of the plurality of target and/or reference condensates, distribution of the plurality of target and/or reference condensates, surface area of the plurality of target and/or reference condensates, dissolution of the plurality of target and/or reference condensates, shape of the plurality of target and/or reference condensates, liquidity or solidification of the plurality of target and/or reference condensates, post-translational modification of the one or more components of the plurality of target and/or reference condensates, and heterogeneous distribution of one or more components within the plurality of target and/or reference condensates.

In some embodiments, the location of the one or more condensates, such as one or more target condensates, one or more reference condensates, a first set of one or more target condensates, a second set of one or more target condensates, is in any portion of a cell, such as any aspect of the cytosol or nucleus of the cell. In some embodiments, the location of the one or more condensates is in an organelle or particles of the cytoplasm, or based on an association thereto. In some embodiments, the location of the one or more condensates describes the association of one or more condensates with another cellular feature, such as the nucleus or centroid. In some embodiments, the location of the one or more condensates is relative to another cellular feature, such as the nucleus or centroid. In some embodiments, the location of the one or more condensates is based on a distance to another cellular feature, such as the nucleus or centroid.

In some embodiments, the number of the one or more condensates is the total number of condensates in the cell or a portion of the cell. In some embodiments, the number of the one or more condensates is the total number of condensates in a cellular portion, such as cytoplasm or nucleus. In some embodiments, the number of the one or more condensates is an estimate of the total number of condensates in the cytoplasm (or nucleus) based on measurements of less than the total cytoplasm (or nucleus). In some embodiments, the number of the one or more condensates is the number of condensates in a portion of the cytoplasm, such as in a field of view or in/associated with a cellular feature. In some embodiments, the number of the one or more target condensates is reflected by the ratio of the total number of one or more target condensates and the total number of one or more reference condensates. In some embodiments, the ratio of the number of one or more target condensates and one or more reference condensates is the ratio of the number of the one or more target condensates and one or more reference condensates that do not comprise the first macromolecule. In some embodiments, the ratio of the number of one or more target condensates and one or more reference condensates is the ratio of the number of one or more target condensates in a portion of the cytoplasm and one or more reference condensates in another portion of the cytoplasm. In some embodiments, the ratio of the number of one or more target condensates and one or more reference condensates is the ratio of the number of one or more target condensates and one or more reference condensates comprising the first macromolecule and located in a location, e.g., nucleus.

In some embodiments, the distribution of the one or more condensates is the distribution of the one or more condensates in a portion of the cytoplasm, such as a cellular feature of the cytoplasm or a field of view. In some embodiments, the distribution of the one or more condensates is the distribution of the one or more condensates relative to a cellular feature, such as the nucleus, an organelle, or particle in the cytoplasm. In some embodiments, the distribution of the one or more condensates is the distribution of the one or more condensates in a portion of the cytoplasm, such as a field of view, relative to a position therein. In some embodiments, the distribution of the one or more condensates is based on the distance of each condensate to a reference point. In some embodiments, the distribution of the one or more condensates is the distribution of the one or more condensates in a portion of the nucleus. The distribution can be uniform or not uniform.

In some embodiments, the size of the one or more condensates is based on the largest condensate-crossing dimension measurement, such as diameter, of each of the one or more condensates. In some embodiments, the size of the one or more condensates is based on the perimeter of each of the one or more condensates. In some embodiments, the size of the one or more condensates is based the cross-sectional area of each of the one or more condensates, or an imaged representation thereof, such as from a top-down view. In some embodiments, the size of the one or more condensates is based on the volume of each of the one or more condensates. In some embodiments, the size of the one or more condensates is based on the average size of the one or more condensates. In some embodiments, the characteristic associated with the one or more condensates is based on the size distribution (such as d5, d10, d90, or d95) of the one or more condensates. In some embodiments, the size of the one or more condensates is determined by a particle size measuring technique, such as a dynamic light scattering technique.

In some embodiments, the stability of the one or more condensates is the stability of the one or more condensates over time, in the presence of a cellular activity, or in the presence of a compound. In some embodiments, the stability is based on the maintenance of, e.g., size, number, shape, or amount of the one or more condensates.

In some embodiments, the diffusion coefficient of a component of the one or more condensates is the diffusion coefficient of the component, such as a first macromolecule, out of the one or more condensates. In some embodiments, the diffusion coefficient of a component of the one or more condensates is the diffusion coefficient of a component that is not the first macromolecule (e.g., other protein, nucleic acid, or compound) out of the one or more condensates.

In some embodiments, the dissolution or reduction in size of the one or more condensates is based on the largest condensate-crossing dimension measurement, such as diameter, of each of the one or more condensates. In some embodiments, the dissolution or reduction in size of the one or more condensates is based on the perimeter of each of the one or more condensates. In some embodiments, the dissolution or reduction in size of the one or more condensates is based on the average size of the one or more condensates. In some embodiments, the dissolution or reduction in size of the one or more condensates is based on the size distribution (such as d5, d10, d90, or d95) of the one or more condensates.

In some embodiments, the surface area of the one or more condensates is an estimated surface area based on the perimeter of each of the one or more condensates.

In some embodiments, the sphericity of the one or more condensates is based on how closely each of the one or more condensates resembles a perfect sphere. In some embodiments, the sphericity of the one or more condensates is an estimate sphericity based on a cross-section or top-down view of each of the one or more condensates. In some, characteristic associated with one or more condensates is the shape of each of the one or more RBM20 condensates. In some embodiments, the characteristic associated with one or more condensates is the portion of the one or more condensates having a shape type or meeting a shape parameter.

In some embodiments, the liquidity and/or solidification of the one or more condensates is based on how the one or more condensates fuse with each other, and/or changes in the structure, size, shape, sphericity, volume, number, and/or or surface area of each of the one or more condensates over time. In some embodiments, the liquidity and/or solidification of the one or more condensates is based on fiber formation.

The characteristic, in some embodiments, may be determined based on any one or more of, e.g., assessment of the one or more condensates in the cell or a portion thereof, such as in the cytoplasm or nucleus or a portion of, assessment of the one or more condensates and/or the macromolecule in any other location inside, outside, or associated with the cell, e.g., the nucleus, or a portion thereof, or assessment of another macromolecule, such as another condensate component.

In some embodiments, determining the characteristic is based on an assessment of at least one cell or at least one portion thereof. In some embodiments, the assessment is of a plurality of cells. In some embodiments, the portion of the cell is a field of view, such as a field of view of a microscope, or a portion thereof. In some embodiments, the portion of the cell is a defined area of an image of the cell, or a portion thereof. In some embodiments, the defined area is based on one or more cellular features (such as by fluorescent fusion protein expression, nuclear dye, or Immunofluorescence (IF) staining), e.g., the boundaries of the nucleus or cell membrane. In some embodiments, the defined area is arbitrarily defined, such as manually or by software. In some embodiments, determining the characteristic is based on replicate assessments. In some embodiments, the replicate assessments are based on more than one portion of an image or more than one image. In some embodiments, determining the characteristic is based on an average or distribution obtained from two or more portions of an image, two or more images, or two or more portions obtained from at least two or more images.

In some embodiments, determining the characteristic is based on an imaging technique. In some embodiments, the imaging technique provides data to assess the characteristic associated with the one or more condensates and/or the macromolecule, including the level of a macromolecule associated with a condensate. In some embodiments, the imaging technique comprises obtaining an image of a composition comprising a cell or a potion thereof. In some embodiments, the image is a two-dimensional image. In some embodiments, the image is a three-dimensional image or rendering thereof. In some embodiments, the imaging technique is coupled with another method feature useful for the methods described herein, such as a fluorescence activated cell sorting (FACS) technique or a fluorescence activated particle sorting (FAPS) technique.

In some embodiments, the methods described herein comprise imaging a sample or a portion thereof, such as the cellular composition, via an imaging technique. In some embodiments, the imaging technique is a fluorescence imaging technique. In some embodiments, the imaging technique comprises a fluorescence imaging technique. In some embodiments, the imaging technique comprises a colorimetric and a fluorescence imaging technique. In some embodiments, the fluorescence imaging technique comprises assessing the fluorescent signal at one or more channels. In some embodiments, the detected light is due to direct labeling of a target, such incorporation or conjugation of a label into a compound or a macromolecule. In some embodiments, the detected light is due to indirect labeling of a target, such a labeled probed that specifically binds to a macromolecule, e.g., a labeled anti-antibody or fragment thereof, a nuclear dye, or Annexin V luciferase that binds to phosphatidylserine (PS) exposed on the outer leaflet of cell membranes during apoptosis. In some embodiments, the label comprises Dendra2, GFP, or mCherry. In some embodiments, determining the characteristic comprises an immunofluorescence technique. In some embodiments, the methods described herein comprise use of a direct labeling technique and an indirect labeling technique.

In some embodiments, the method further comprises determining one or more cellular feature of the cell, such as in addition to a condensate and/or a macromolecule, if present. One or ordinary skill in the art will readily recognize that cellular features can be determined in a number of ways. In some embodiments, the method further comprises contacting at least a portion of the composition or the cell with a stain, such as a nuclear dye. In some embodiments, the stain is a fluorescent stain. In some embodiments, the stain is a histochemical stain. In some embodiments, the stain is an immune-based stain, such as used in an immunohistochemistry or immunocytochemistry technique. In some embodiments, the stain allows for visualization of a cellular feature, if present, such as at least a portion of any one or more of the plasma or cell membrane, cytoplasm, cytoskeleton, nucleus, endoplasmic reticulum (rough and/or smooth), ribosome, Golgi body, lysosomes, mitochondrion, vacuole, or centrosome. In some embodiments, the methods described herein further comprise contacting at least a portion of the cellular composition or the cell with a fixative.

In some embodiments, the characteristic is determined based on the ratio of the number of cells having one or more target condensates with the characteristic and the number of cells not having the one or more target condensates with the characteristic. In some embodiments, the characteristic is determined based on the number of cells having one or more target condensates with the characteristic.

In some embodiments, the characteristic is determined over a period of time, e.g., at two or more time points. In some embodiments, determining the characteristic comprises assessing the change in the characteristic over a period of time. In some embodiments, the characteristic, such as a level of association, is assessed during the life of a condensate. For example, as discussed herein, condensates are dynamic and change over time, and thus the characteristic is assessed at a time when the impact of a compound on a condensate can be accurately measured. In some embodiments, the characteristic, such as a level of association, is assessed during the life of a cell, such as during mitosis or not during mitosis.

In some embodiments, the characteristic is determined using one or more measurements and/or techniques. In some embodiments, more than one characteristic associated with one or more condensates and/or the polypeptide is determined using one or more measurements and/or techniques.

In some embodiments, the methods described herein comprise techniques for, e.g., visualizing, analyzing, and/or quantifying macromolecules and/or precursors thereof. Such techniques are well known by one of ordinary skill in the art. For example, encompassed herein are microscopy techniques for visualizing proteins, such as fluorescently labeled proteins, including those which are compatible with cell systems. Also encompassed herein are mass spectrometry (MS) techniques for analyzing the composition of proteins, including post-translation modifications, quantifying proteins, and studying the composition of condensates (e.g., by a cross-linking MS technique "XL-MS"). Also encompassed herein are functional assays for assessing cellular processes. Also encompassed herein are enrichment and/or isolation techniques, e.g., centrifuge techniques for isolating cell fractions or affinity-based techniques for isolating proteins or nucleic acids. In some embodiments, the technique assesses the characteristic in one or more cells or in a defined area(s) of one or more cells. In some embodiments, the technique assesses one or more of the intensity, area, and condensate count in one or more cells or in a defined area(s) of one or more cells. In some embodiments, the technique assesses the number of cells with or without the characteristic. In some embodiments, the technique assesses the number of condensates within a cell with or without the characteristic. In some embodiments, the method comprises using a z-score to evaluate an assay and results therefrom. Z-scores, and uses thereof, are known in the art. See, e.g., Zhang et al., *J Biomol Screen,* 1999.

In some embodiments, the location of the one or more condensates is determined by assessing the presence, absence, or level of the one or more condensates in at least a portion of the cell, such as a cellular feature, e.g., the cytoplasm or nucleus, or in association with a portion of the cell. In some embodiments, determining the location of the one or more condensates comprises determining a cellular feature.

In some embodiments, the number of the one or more condensates is determined by assessing the total number of condensates in the cell, such as the cytoplasm. In some embodiments, the number of the one or more condensates is determined by assessing the number of condensates in a portion, such as a field of view, of the cell, e.g., the cytoplasm. In some embodiments, the number of the one or more condensates is determined by estimating the total number of condensates in the cell, such as the cytoplasm, or a portion thereof, based on measurements of less than the total of the cell.

In some embodiments, the size of the one or more condensates is determined by assessing the largest condensate-crossing dimension measurement, such as diameter, of each of the one or more condensates. In some embodiments, the size of the one or more condensates is determined by assessing the perimeter of each of the one or more condensates. In some embodiments, the size of the one or more condensates is determined by assessing the cross-sectional area of each of the one or more condensates, or an imaged representation thereof, such as from a top-down view. In some embodiments, the size of the one or more condensates is determined by a particle size measuring technique, such as a dynamic light scattering technique.

In some embodiments, the dissolution or reduction in size of the one or more condensates is determined based on changes in the structure of each of the one or more condensates over time, in the presence of a cellular activity, or in the presence of a compound.

In some embodiments, the surface area of the one or more condensates is determined based on estimating a surface area using measured parameters (e.g., perimeter, largest condensate-crossing dimension measurement) of each of the one or more condensates.

In some embodiments, the method comprises contacting a cellular composition with a compound, wherein the cellular composition comprises the one or more target condensates, and the method further comprises causing the formation of the one or more target condensates prior to step (a). In some embodiments, the method comprises contacting a cellular composition with a compound, wherein the one or more target condensates form after contacting the cellular composition with the compound, and the method further comprises causing the formation of the one or more target condensates. Methods of forming condensates are known. For examples, cellular stress can cause the formation of stress granules. Examples of cellular stress include arsenate treatment, a temperature change, or a pH change. Accordingly, in some embodiments, causing the formation of the one or more target condensates comprises contacting the cellular composition with arsenate, an acid, or a base or altering the temperature of the cellular composition.

For methods that require a first set of one or more target condensates and a second set of one or more target condensates, any target condensates disclosed herein may be used. In some embodiments, the first set of one or more target condensates and the second set of one or more target condensates are different classes of condensates, such as any of the classes of condensates disclosed herein.

In some embodiments, the method comprises analyzing one or more images to assess a characteristic of a condensate. In some embodiments, analyzing comprises mapping cell boundaries, or boundaries of a portion of a cell, such as an organelle. In some embodiments, analyzing comprises mapping boundaries of a condensate. In some embodiments, analyzing the images is completed and/or facilitated by analysis software. In some embodiments, the one or more images are compared, such as in a time course study. In some embodiments, analyzing comprises measuring signal (e.g., signal of fluorescent fusion protein, IF staining, or luminescence) intensity of a condensate, a macromolecule, and/or a compound (e.g., a co-localizing compound with the condensate and/or the macromolecule). In some embodiments, analyzing further comprises calculating enrichment of a measured signal, such as a measured signal within a condensate boundary.

In some embodiments, the co-localization of condensate components, such as a first macromolecule and a second macromolecule, is determined by assessing for the presence, absence, or level of a component (or the compound) in or associated with the condensate. In some embodiments, assessing, such as measuring, is done directly or indirectly. In some embodiments, the condensate component is assessed using a mass spectrometry technique, such as APEX, or XL-MS. In some embodiments, the condensate component is assessed using a FAPS technique. In some embodiments, assessing comprise use of a labeling technique, such as directly conjugating a label to a condensate component or using an immuno-label, such as used in an IF technique. In some embodiments, the condensates are isolated and/or enriched, and then the presence, absence, or level of condensate components in or associated with the condensates is assessed. In some embodiments, the condensates are not isolated and/or enriched, such as from other cellular components, e.g., assessing occurs in situ. In some embodiments, the condensates, or the cell comprising the condensates, are fixed prior to assessing. In some embodiments, the condensates, or the cell comprising the condensates, are not fixed prior to assessing. In some embodiments, known techniques in the art can be used to quantify the amount of a component in a condensate, such as imaging, mass spectrometry, western blot, immunoprecipitation (IP), immunofluorescence (IF) staining, in situ, FISH, northern blot, or qPCR.

Macromolecules

In some embodiments, the macromolecule, such as the first macromolecule, one or more of the at least one additional macromolecule, or reference macromolecule, is a nucleic acid or protein. In some embodiments, the macromolecule, such as the first macromolecule, the one or more of the at least one additional macromolecule, or reference macromolecule, is a protein or protein fragment. In some embodiments, the protein or protein fragment comprises a Low Complexity Domain or an Intrinsically Disordered Sequence. In some embodiments, the macromolecule is a transcription factor or an RNA binding protein. In some embodiments, the macromolecule is a nucleic acid, such as RNA or DNA. In some embodiments, the macromolecule is a RNA.

In some embodiments, the first macromolecule is FUS or eIF3. In some embodiments, the at least one additional macromolecule is FUS, eIF3, G3BP1, FUS and G3BP1, or eIF3 and G3BP1. In some embodiments, the first macromolecule is FUS and the at least one additional macromolecule is eIF3, G3BP1, or eIF3 and G3BP1. In some embodiments, the first macromolecule is eIF3 and the at least one additional macromolecule is FUS, G3BP1, or FUS and G3BP1.

In some embodiments, the first macromolecule comprises a mutation that alters the level of association of the first macromolecule with the one or more target condensates compared to a related macromolecule that does not comprise the mutation. In some embodiments, one or more of the at least one additional macromolecule comprise a mutation that alters its corresponding level of association with the one or more target condensates compared to a related macromolecule that does not comprise the mutation. In some embodiments, each of the at least one additional macromolecule comprise a mutation that alters its corresponding level of association with the one or more target condensates compared to a related macromolecule that does not comprise the mutation. In some embodiments, the first macromolecule comprises a mutation that alters the level of association of the first macromolecule with the one or more target condensates compared to the level of association of the first macromolecule with another condensate. In some embodiments, the first macromolecule does not have an altered association (or has an altered association for at most about 2 fold) with the one or more target condensates, compared to a related macromolecule that does not comprise the mutation. In some embodiments, the first macromolecule comprises a mutation that alters the level of association of a second macromolecule with the one or more target condensates. In some embodiments, the first macromolecule and the second macromolecule are different. In some embodiments, the first macromolecule comprises a mutation that alters the level of association of the first macromolecule with the one or more target condensates only in one or more cell (e.g., neuron) or tissue types, compared to the association of the first macromolecule with the one or more target condensates in another cell (e.g., cardiomyocyte) or tissue type. In some embodiments, the mutation is related to a disease, such as a neurodegenerative, proliferative, immunological, cardiac, or metabolic disease.

In some embodiments, the macromolecule, such as the first macromolecule or one or more of the at least one additional macromolecules is aberrantly expressed in a disease or stress state. In some embodiments, the first macromolecule is aberrantly expressed in a disease or stress state. In some embodiments, one or more of the at least one additional macromolecules is aberrantly expressed in a disease or stress state. In some embodiments, each of the at least one additional macromolecules is aberrantly expressed in a disease state. In some embodiments, a disease or stress state level of association of the macromolecule with the one or more target condensates is altered compared to a normal (e.g., healthy or non-stressed) state level of association of the macromolecule with the one or more target condensates. In some embodiments, a disease or stress state level of association of the first macromolecule with the one or more target condensates is altered compared to a normal state level of association of the first macromolecule with the one or more target condensates. In some embodiments, a disease or stress state level of association of one or more of the at least one additional macromolecule with the one or more target condensates is altered compared to a normal state level of association of one or more of the at least one additional macromolecule with the one or more target condensates. In some embodiments, a disease or stress state level of association of each of the at least one additional macromolecule with the one or more target condensates is altered compared to a normal state level of association of each of the at least one additional macromolecule with the one or more target condensates. In some embodiments, a disease or stress state level of association of the first macromolecule with the one or more target condensates is altered (e.g., altered at least about 2 fold) compared to a normal state level of association of the first macromolecule with the one or more target condensates, while a disease or stress state level of association of one or more of the at least one additional macromolecule with the one or more target condensates is not altered (or altered less than e.g., 2 fold) compared to a normal state level of association of one or more of the at least one additional macromolecule with the one or more target condensates.

In some embodiments, the at least one additional macromolecule is 2 or more, 3 or more, 4 or more, 5 or more, 6 or more, 7 or more, 8 or more, 9 or more, 10 or more macromolecules. In some embodiments, the at least one additional macromolecule is 2 or more macromolecules. In some embodiments, the at least one additional macromolecule is 3 or more macromolecules. In some embodiments, the at least one additional macromolecule is 5 or more macromolecules. In some embodiments, the at least one additional macromolecule is 1-10 macromolecules, such as 1-3, 2-5, 2-9, 3-8, 4-7, 5-10, or 7-10 macromolecules. In some embodiments, the at least one additional macromolecule is a single macromolecule. In some embodiments, the at least one additional macromolecule is 2, 3, 4, 5, 6, 7, 8, 9, or 10 macromolecules. In some embodiments, the at least one additional macromolecule is 2 macromolecules. In some embodiments, the at least one additional macromolecule is 3 macromolecules. In some embodiments, the at least one additional macromolecule is 5 macromolecules.

In some embodiments, the first macromolecule and/or one or more of the at least one additional macromolecule is a fusion protein. In some embodiments, the fusion protein comprises a label. In some embodiments, the label is a fluorescent or luminescent protein. In some embodiments, the first macromolecule is a first fusion protein comprising a first label and one of the at least one additional macromolecule is a second fusion protein comprising a second label. In some embodiments, the at least one additional macromolecule is a plurality of macromolecules. In some embodiments, the plurality comprises a first fusion protein comprising a first label and a second fusion protein comprising a second label. In some embodiments, the first macromolecule is a first fusion protein comprising a first label and the plurality comprises a second fusion protein comprising a second label and a third fusion protein comprising a third label. In some embodiments, the first label and the second label are distinguishable. In some embodiments, the first label, the second label, and the third label are distinguishable.

In some embodiments, the first macromolecule and/or one or more of the at least one additional macromolecule is tagged with a label, e.g., a fluorescein. Additionally or alternatively, the macromolecules may be labeled by contacting the cellular composition with a label. Accordingly, in some embodiments, the method further comprises contacting the cellular composition with a label. In some embodiments, the method further comprises labeling the first macromolecule and/or one or more of the at least one additional macromolecule. In some embodiments, the labeling comprises contacting the cellular composition with an antibody or antigen-binding fragment thereof comprising a label. In some embodiments, the label is a radioactive label, a colorimetric label, or a fluorescent label.

In some embodiments, the method comprises contacting the cellular composition with a fixative. Exemplary fixatives include formaldehyde, glutaraldehyde and paraformaldehyde. In some embodiments, the method comprises contacting the cellular composition with a permeabilizing agent. Exemplary permeabilizing agents include saponin compounds, methanol, acetone, or detergent, such as Triton X-100.

Methods of Identifying Compound Characteristics

Also provided herein are methods of identifying a compound characteristic, such as a moiety, responsible, in whole or in part, for any one or more of the following specificities: macromolecule specificity, condensate specificity, and tissue specificity. In some embodiments, the method of identifying a compound characteristic comprises assessing a plurality of compounds according to the methods described herein and then identifying a compound characteristic that a subset or all of the plurality of compounds contains, wherein the subset or all of the plurality of compounds exhibit a similar specificity.

In some aspects, the method described herein is used in a screen to assay a library of compounds. In some aspects, the method described herein is used in a screen to assay a library of condensates. In some aspects, the method described herein is used in a screen to assay a library of cells, such as disease model cell lines. In some aspects, the method described herein is used in a screen to assay a library of cells, wherein the library of cells comprises cell having different mutations in a macromolecule, such as a disease related mutation. In some embodiments, the methods described herein comprise assessing two or more compounds in a single system, such as a composition comprising a cell.

In some aspects, the method described herein is formatted for any level of throughput, such as high throughput, medium throughput, or low throughput.

In some embodiments, the method described herein further comprises assessing the identified compound using a second cell-based assay, such as in a cell composition of similar disease type (e.g., breast cancer) but with different mutations (e.g., different alleles). In some embodiments, the method described herein further comprises assessing the identified compound using an in vitro assay.

In some embodiments, the method described herein further comprises determining the amount of a compound in a cell, or portion thereof, or one or more target condensates. In some embodiments, determining the amount of the compound comprises quantifiably detecting the compound. In some embodiments, determining the amount of the compound comprises quantifiably detecting a label of the compound. In some embodiments, determining the amount of the compound comprises detecting activity of the compound and calculating the amount of compound needed to cause the amount of activity detected (e.g., causes the dissociation of a macromolecule with the one or more target condensates). In some embodiments, the amount of compound is determined by mass spectrometry, liquid chromatography, and/or ultraviolet-visible spectrophotometry. In some embodiments, the amount of compound is determined by fluorescence microscopy. Standard curves may be used to aid in determining the amount of the compound.

In some embodiments, provided herein are methods of identifying a compound characteristic associated with preferentially affecting the level of association of a first macromolecule with one or more target condensates, comprising: (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; and (d) identifying a characteristic that a subset or all of the identified compounds have in common in addition to the ability to preferentially affect the level of association of the first macromolecule with the one or more target condensates. Also provided herein are methods of identifying a compound characteristic associated with preferentially affecting the level of association of a first macromolecule with a first set of one or more target condensates, wherein the method comprises performing the steps of a method disclosed herein of identifying a plurality of compounds that preferentially affect the level of association of a first macromolecule with the first set of one or more target condensates; and identifying a characteristic that a subset or all of the identified compounds have in common in addition to the ability to preferentially affect the level of association of the first macromolecule with the first set of one or more target condensates.

Also provided herein are methods of identifying a compound characteristic associated with preferentially decreasing the level of association of a first macromolecule with one or more target condensates, comprising: (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; and (d) identifying a characteristic that a subset or all of the identified compounds have in common in addition to the ability to preferentially decrease the level of association of the first macromolecule with the one or more target condensates. Also provided herein are methods of identifying a compound characteristic associated with preferentially decreasing the level of association of a first macromolecule with a first set of one or more target condensates, wherein the method comprises performing the steps of a method disclosed herein of identifying a plurality of compounds that preferentially decrease the level of association of a first macromolecule with the first set of one or more target condensates; and identifying a characteristic that a subset or all of the identified compounds have in common in addition to the ability to preferentially decrease the level of association of the first macromolecule with the first set of one or more target condensates.

Also provided herein are methods of identifying a compound characteristic associated with preferentially increasing the level of association of a first macromolecule with one or more target condensates, comprising: (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; and (d) identifying a characteristic that a subset or all of the identified compounds have in common in addition to the ability to preferentially increase the level of association of the first macromolecule with the one or more target condensates. Also provided herein are methods of identifying a compound characteristic associated with preferentially increasing the level of association of a first macromolecule with a first set of one or more target condensates, wherein the method comprises performing the steps of a method disclosed herein of identifying a plurality of compounds that preferentially increasing the level of association of a first macromolecule with the first set of one or more target condensates; and identifying a characteristic that a subset or all of the identified compounds have in common in addition to the ability to preferentially increasing the level of association of the first macromolecule with the first set of one or more target condensates.

Also provided herein are methods of identifying a compound characteristic associated with preferentially causing the first macromolecule to associate with one or more target condensates, comprising: (a) contacting a cellular composition with a compound, wherein (i) the cellular composition comprises one or more target condensates; and/or (ii) the one or more target condensates form simultaneously with and/or after contacting the cellular composition with the compound; (b) determining if a first macromolecule and at least one additional macromolecule are associated with the one or more target condensates; (c) performing steps (a) and (b) for a plurality of compounds; and (d) identifying a characteristic that a subset or all of the identified compounds have in common in addition to the ability to preferentially cause the first macromolecule to associate with the one or more target condensates. Also provided herein are methods of identifying a compound characteristic associated with preferentially causing the first macromolecule to associate with a first set of one or more target condensates, wherein the method comprises performing the steps of a method disclosed herein of identifying a plurality of compounds that preferentially cause the first macromolecule to associate with one or more target condensates; and identifying a characteristic that a subset or all of the identified compounds have in common in addition to the ability to preferentially cause the first macromolecule to associate with the first set of one or more target condensates.

Also provided herein are methods of identifying a compound characteristic associated with preferentially causing the first macromolecule to disassociate with one or more target condensates, comprising: (a) contacting a cellular composition with a compound, wherein (i) the cellular composition comprises one or more target condensates; and/or (ii) the one or more target condensates form simultaneously with and/or after contacting the cellular composition with the compound; (b) determining if a first macromolecule and at least one additional macromolecule are disassociated with the one or more target condensates; (c) performing steps (a) and (b) for a plurality of compounds; and (d) identifying a characteristic that a subset or all of the identified compounds have in common in addition to the ability to preferentially cause the first macromolecule to disassociate with the one or more target condensates. Also provided herein are methods of identifying a compound characteristic associated with preferentially causing the first macromolecule to disassociate with a first set of one or more target condensates, wherein the method comprises performing the steps of a method disclosed herein of identifying a plurality of compounds that preferentially cause the first macromolecule to disassociate with one or more target condensates; and identifying a characteristic that a subset or all of the identified compounds have in common in addition to the ability to preferentially cause the first macromolecule to disassociate with the first set of one or more target condensates.

In some embodiments, provided herein are methods of identifying a compound characteristic associated with preferentially affecting the level of association of a first macromolecule with a first set of one or more condensates compared to one or more other sets of one or more condensates (e.g., a second set of one or more condensates), comprising: (a) contacting a cellular composition with a compound, wherein (i) the cellular composition comprises the first set of one or more condensates and the one or more other sets of one or more condensates (e.g., the second set of one or more condensates); and/or (ii) the first set of one or more condensates and the one or more other sets of one or more condensates (e.g., the second set of one or more condensates) form simultaneously with and/or after contacting the cellular composition with the compound; (b) determining the level of association of the first macromolecule with the first set of one or more condensates and the level of association of the first macromolecule with each other set of the one or more condensates (e.g., the second set of one or more condensates); (c) performing steps (a) and (b) for a plurality of compounds; and (d) identifying a characteristic that a subset or all of the identified compounds have in common in addition to the ability to preferentially affect the level of association of the first macromolecule with the first set of one or more condensates. In some embodiments, the first (or other) set of one or more condensates are of the same type, e.g., all are stress granules. In some embodiments, the first (or other) set of one or more condensates share a common macromolecule. In some embodiments, the method further comprises determining a level of association of one or more additional macromolecule with the first set of one or more condensates and the level of association of the one or more additional macromolecule with each other set of one or more condensates. In some embodiments, the method further comprises determining a level of association of the first macromolecule with a reference condensate, and/or a level of association of one or more additional macromolecule with the reference condensate.

In some embodiments, provided herein are methods of identifying a compound characteristic associated with preferentially affecting the level of association of a first macromolecule with one or more target condensates in a first set of one or more cell/tissue types compared to one or more other sets of one or more cell/tissue types, comprising: (a) contacting a first set of one or more cellular compositions comprising one or more cell/tissue types, and one or more other sets of one or more cellular compositions comprising one or more cell/tissue types, with a compound, wherein (i) each cellular composition comprises one or more target condensates; and/or (ii) the one or more target condensates form simultaneously with and/or after contacting each cellular composition with the compound; (b) determining the level of association of the first macromolecule with the one or more target condensates in the first set of one or more cellular compositions, and the level of association of the first macromolecule with the one or more target condensates in each other set of one or more cellular compositions; (c) performing steps (a) and (b) for a plurality of compounds; and (d) identifying a characteristic that a subset or all of the identified compounds have in common in addition to the ability to preferentially affect the level of association of the first macromolecule with the one or more target condensates in the first set of one or more cellular compositions comprising one or more cell/tissue types. In some embodiments, the method further comprises determining a level of association of one or more additional macromolecule with the one or more target condensates in the first set of one or more cellular compositions, and the level of association of the one or more additional macromolecule with the one or more target condensates in each other set of one or more cellular compositions. In some embodiments, the method further comprises determining a level of association of the first macromolecule with a reference condensate in the first set of one or more cellular compositions, and a level of association of the first macromolecule with a reference condensate in each other set of one or more cellular compositions. In some embodiments, the method further comprises determining a level of association of one or more additional macromolecule with a reference condensate in the first set of one or more cellular compositions, and a level of association of the one or more additional macromolecule with a reference condensate in each other set of one or more cellular compositions.

In some embodiments, the methods described herein can further identify one or more characteristics that a subset or all of the identified compounds have in common in altering one or more of: (i) location of the one or more target condensates; (ii) distribution of the one or more target condensates and/or its component (e.g., the first macromolecule); (iii) number of the one or more target condensates; (iv) size of the one or more target condensates; (v) ratio of the amount of one or more target condensates and a reference condensate; (vi) a functional activity associated with the one or more target condensates; (vii) composition of the one or more target condensates; (viii) co-localization of the one or more target condensates with a biomolecule; (ix) diffusion coefficient of a component (e.g., the first macromolecule) of the one or more target condensates; (x) stability of the one or more target condensates; (xi) dissolution or reduction in size of the one or more target condensates; (xii) surface area of the one or more target condensates; (xiii) sphericity of the one or more target condensates; (xiv) liquidity of the one or more target condensates; (xv) solidification of the one or more target condensates; (xvi) location of a condensate component (e.g., the first macromolecule); (xvii) amount of a condensate component (e.g., the first macromolecule) or a precursor thereof; (xviii) condensate partitioning of a biomolecule (e.g., the first macromolecule) into the one or more target condensates; (xix) a functional activity associated with a condensate component (e.g., the first macromolecule); (xx) aggregation of a condensate component (e.g., the first macromolecule); (xxi) post-translational modification status of a condensate component (e.g., the first macromolecule); and (xxii) amount of a degradation product of a condensate component (e.g., the first macromolecule).

Methods of Designing a Compound

Also provided herein are methods of designing a compound having one or more of the following specificities: macromolecule specificity, condensate specificity, and tissue specificity. In some embodiments, the method of designing comprises selecting and/or assembling one or more moieties having a desired specificity.

In some embodiments, the method of designing a compound that preferentially affects the level association of a first macromolecule with one or more target condensates comprising (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; (d) identifying a characteristic that a subset or all of the identified compounds have in common in addition to the ability to preferentially affect the level of association of the first macromolecule with one or more target condensates; and (e) designing a compound that comprises the identified characteristic, thereby designing a compound that preferentially affects the level of association of the first macromolecule with one or more target condensates.

Also provided herein are methods of designing a compound that preferentially decreases the level of association of a first macromolecule with one or more target condensates comprising (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; (d) identifying a characteristic that a subset or all of the identified compounds have in common in addition to the ability to preferentially decrease the level of association of the first macromolecule with one or more target condensates; and (e) designing a compound that comprises the identified characteristic, thereby designing a compound that preferentially decreases the level of association of the first macromolecule with one or more target condensates.

Also provided herein are methods of designing a compound that preferentially increases the level of association of a first macromolecule with one or more target condensates comprising (a) contacting a cellular composition with a compound, wherein (i) the cellular composition comprises one or more target condensates; and/or (ii) the one or more target condensates form simultaneously with and/or after contacting the cellular composition with the compound; (b) determining the level of association of the first macromolecule with the one or more target condensates and a level of association of at least one additional macromolecule with the one or more target condensates; (c) performing steps (a) and (b) for a plurality of compounds; (d) identifying a characteristic that a subset or all of the identified compounds have in common in addition to the ability to preferentially increase the level of association of the first macromolecule with one or more target condensates; and (e) designing a compound that comprises the identified characteristic, thereby designing a compound that preferentially increases the level of association of the first macromolecule with one or more target condensates.

Also provided herein are methods of designing a compound that preferentially causes the first macromolecule to associate with one or more target condensates comprising (a) contacting a cellular composition with a compound, wherein (i) the cellular composition comprises one or more target condensates; and/or (ii) the one or more target condensates form simultaneously with and/or after contacting the cellular composition with the compound; (b) determining if a first macromolecule and at least one additional macromolecule are associated with the one or more target condensates; (c) performing steps (a) and (b) for a plurality of compounds; (d) identifying a characteristic that a subset or all of the identified compounds have in common in addition to the ability to preferentially cause the first macromolecule to associate with one or more target condensates; and (e) designing a compound that comprises the identified characteristic, thereby designing a compound that preferentially causes the first macromolecule to associate with one or more target condensates.

Also provided herein are methods of designing a compound that preferentially causes the first macromolecule to disassociate with one or more target condensates comprising (a) contacting a cellular composition with a compound, wherein (i) the cellular composition comprises one or more target condensates; and/or (ii) the one or more target condensates form simultaneously with and/or after contacting the cellular composition with the compound; (b) determining if a first macromolecule and at least one additional macromolecule are disassociated with the one or more target condensates; (c) performing steps (a) and (b) for a plurality of compounds; (d) identifying a characteristic that a subset or all of the identified compounds have in common in addition to the ability to preferentially cause the first macromolecule to disassociate with one or more target condensates; and (e) designing a compound that comprises the identified characteristic, thereby designing a compound that preferentially causes the first macromolecule to disassociate with one or more target condensates.

In some embodiments, provided herein are methods of identifying a compound characteristic associated with preferentially affecting the level of association of a first macromolecule with a first set of one or more condensates compared to one or more other sets of one or more condensates (e.g., a second set of one or more condensates), comprising: (a) contacting a cellular composition with a compound, wherein (i) the cellular composition comprises the first set of one or more condensates and the one or more other sets of one or more condensates (e.g., the second set of one or more condensates); and/or (ii) the first set of one or more condensates and the one or more other sets of one or more condensates (e.g., the second set of one or more condensates) form simultaneously with and/or after contacting the cellular composition with the compound; (b) determining the level of association of the first macromolecule with the first set of one or more condensates and the level of association of the first macromolecule with each other set of the one or more condensates (e.g., the second set of one or more condensates); (c) performing steps (a) and (b) for a plurality of compounds; (d) identifying a characteristic that a subset or all of the identified compounds have in common in addition to the ability to preferentially affects the level of association of the first macromolecule with the first set of one or more condensates; and (e) designing a compound that comprises the identified characteristic, thereby designing a compound that preferentially affects the level of association of the first macromolecule with the first set of one or more condensates. In some embodiments, the first (or other) set of one or more condensates are of the same type, e.g., all are stress granules. In some embodiments, the first (or other) set of one or more condensates share a common macromolecule.

In some embodiments, provided herein are methods of identifying a compound characteristic associated with preferentially affecting the level of association of a first macromolecule with one or more target condensates in a first set of one or more cell/tissue types compared to one or more other sets of one or more cell/tissue types, comprising: (a) contacting a first set of one or more cellular compositions comprising one or more cell/tissue types, and one or more other sets of one or more cellular compositions comprising one or more cell/tissue types, with a compound, wherein (i) each cellular composition comprises one or more target condensates; and/or (ii) the one or more target condensates form simultaneously with and/or after contacting each cellular composition with the compound; (b) determining the level of association of the first macromolecule with the one or more target condensates in the first set of one or more cellular compositions, and the level of association of the first macromolecule with the one or more target condensates in each other set of one or more cellular compositions; (c) performing steps (a) and (b) for a plurality of compounds; (d) identifying a characteristic that a subset or all of the identified compounds have in common in addition to the ability to preferentially affects the level of association of the first macromolecule with the one or more target condensates in the first set of one or more cellular compositions comprising one or more cell/tissue types; and (e) designing a compound that comprises the identified characteristic, thereby designing a compound that preferentially affects the level of association of the first macromolecule with the one or more target condensates in the first set of one or more cellular compositions comprising one or more cell/tissue types.

In some embodiments, the methods described herein further comprise identify one or more characteristics that a subset or all of the identified compounds have in common in altering one or more of: (i) location of the one or more target condensates; (ii) distribution of the one or more target condensates and/or its component (e.g., the first macromolecule); (iii) number of the one or more target condensates; (iv) size of the one or more target condensates; (v) ratio of the amount of one or more target condensates and a reference condensate; (vi) a functional activity associated with the one or more target condensates; (vii) composition of the one or more target condensates; (viii) co-localization of the one or more target condensates with a biomolecule; (ix) diffusion coefficient of a component (e.g., the first macromolecule) of the one or more target condensates; (x) stability of the one or more target condensates; (xi) dissolution or reduction in size of the one or more target condensates; (xii) surface area of the one or more target condensates; (xiii) sphericity of the one or more target condensates; (xiv) liquidity of the one or more target condensates; (xv) solidification of the one or more target condensates; (xvi) location of a condensate component (e.g., the first macromolecule); (xvii) amount of a condensate component (e.g., the first macromolecule) or a precursor thereof; (xviii) condensate partitioning of a biomolecule (e.g., the first macromolecule) into the one or more target condensates; (xix) a functional activity associated with a condensate component (e.g., the first macromolecule); (xx) aggregation of a condensate component (e.g., the first macromolecule); (xxi) post-translational modification status of a condensate component (e.g., the first macromolecule); and (xxii) amount of a degradation product of a condensate component (e.g., the first macromolecule). In some embodiments, the methods described herein further comprise designing the compound that further comprises one or more of the above identified characteristics (in addition to preferentially affecting the level of association of the macromolecule with the one or more target condensates), thereby designing a compound that not only preferentially affects the level of association of the macromolecule with the one or more target condensates, but also can alter one or more of the above mentioned condensate/condensate component characteristics.

In some embodiments, the methods described herein may be used to develop one or more rule sets based on achieved desired alteration of the association of a macromolecule with one or more target condensates (and/or desired alteration of one or more above mentioned condensate/condensate component characteristics). In some embodiments, the one or more rule sets can be used as a basis for the identification and/or design of one or more compounds using an approach comprising modeling, computer and/or calculation-based techniques, e.g., bioinformatic, cheminformatic, and/or artificial intelligence (AI)-based identification of a compound having a desired modulation of one or more characteristics described herein. Also provided are computer software for determining and/or applying the one or more rule sets.

Those skilled in the art will recognize that several embodiments are possible within the scope and spirit of the disclosure of this application. The disclosure is illustrated further by the examples below, which are not to be construed as limiting the disclosure in scope or spirit to the specific procedures described therein.

Exemplary Embodiments

Among the provided embodiments are:

Embodiment 1. A method of identifying a compound that preferentially affects a level of association of a first macromolecule with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially affects the level of association of the first macromolecule with the one or more target condensates if the compound alters the level of the first macromolecule as compared to a first reference level more than the compound alters the level of each additional macromolecule as compared to a reference level for each additional macromolecule.

Embodiment 2. The method of embodiment 1, wherein the compound does not measurably alter the level of each additional macromolecule compared to the reference level for each additional macromolecule.

Embodiment 3. A method of identifying a compound that preferentially increases a level of association of a first macromolecule with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially increases the level of association of the first macromolecule with the one or more target condensates if the compound increases the level of the first macromolecule as compared to a first reference level more than the compound increases the level of each additional macromolecule as compared to a reference level for each additional macromolecule.

Embodiment 4. The method of embodiment 3, wherein the compound does not measurably increase the level of each additional macromolecule compared to the reference level for each additional macromolecule.

Embodiment 5. A method of identifying a compound that preferentially decreases a level of association with one or more target condensates of a first macromolecule, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining the level of association of the first macromolecule with the one or more target condensates and a level of association of at least one additional macromolecule with the one or more target condensates, wherein the compound preferentially decreases the level of association of the first macromolecule with the one or more target condensates if the compound alters the level of the first macromolecule as compared to a first reference level more than the compound decreases the level of each additional macromolecule as compared to a reference level for each additional macromolecule.

Embodiment 6. The method of embodiment 5, wherein the compound does not measurably decrease the level of each additional macromolecule compared to the reference level for each additional macromolecule.

Embodiment 7. The method of any one of embodiments 1-6, wherein the first reference level is a level of association of the first macromolecule with one or more reference condensates determined in the absence of the compound.

Embodiment 8. The method of any one of embodiments 1-7, wherein the reference level for each additional macromolecule is a level of association for each additional macromolecule with one or more reference condensates determined in the absence of the compound.

Embodiment 9. A method of identifying a compound that preferentially causes a first macromolecule to associate with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining if a first macromolecule and at least one additional macromolecule are associated with the one or more target condensates, wherein the compound preferentially causes the first macromolecule to associate with the one or more target condensates if: (1) the compound causes the first macromolecule to associate with the one or more target condensates; (2) the compound does not cause each additional macromolecule to associate with the one or more target condensates; and (3) the first macromolecule would not be associated with the one or more target condensates in the absence of the compound.

Embodiment 10. The method of embodiment 9, wherein the compound preferentially causes the first macromolecule to associate with the one or more target condensates if (4) one or more of the at least one additional macromolecule would not be associated with the one or more target condensates in the absence of the compound.

Embodiment 11. The method of embodiment 9, wherein the compound preferentially causes the first macromolecule to associate with the one or more target condensates if (4)

each of the at least one additional macromolecule would not be associated with the one or more target condensates in the absence of the compound.

Embodiment 12. A method of identifying a compound that preferentially causes a first macromolecule to disassociate with one or more target condensates, the method comprising: (a) contacting a cellular composition with a compound, wherein (i) the cellular composition comprises the one or more target condensates; and/or (ii) the one or more target condensates form simultaneously with and/or after contacting the cellular composition with the compound; and (b) determining if a first macromolecule and at least one additional macromolecule are associated with the one or more target condensates, wherein the compound preferentially causes the first macromolecule to disassociate with the one or more target condensates if: (1) the compound causes the first macromolecule not to associate with the one or more target condensates; (2) the compound does not cause each additional macromolecule not to associate with the one or more target condensates; and (3) the first macromolecule would be associated with the one or more target condensates in the absence of the compound.

Embodiment 13. The method of embodiment 12, wherein the compound preferentially causes the first macromolecule to associate with the one or more target condensates if (4) one or more of the at least one additional macromolecule would be associated with the one or more target condensates in the absence of the compound.

Embodiment 14. The method of embodiment 12, wherein the compound preferentially causes the first macromolecule to associate with the one or more target condensates if (4) each of the at least one additional macromolecule would be associated with the one or more target condensates in the absence of the compound.

Embodiment 15. The method of any one of embodiments 1-14, wherein step (a) comprises contacting a cellular composition with a compound, wherein the cellular composition comprises the one or more target condensates, and the method further comprises causing the formation of the one or more target condensates prior to step (a).

Embodiment 16. The method of any one of embodiments 1-14, wherein step (a) comprises contacting a cellular composition with a compound, wherein the one or more target condensates form after contacting the cellular composition with the compound, and the method further comprises causing the formation of the one or more target condensates.

Embodiment 17. The method of any one of embodiments 1-16, wherein the at least one additional macromolecule is 2 or more, 3 or more, 4 or more, or 5 or more macromolecules.

Embodiment 18. The method of any one of embodiments 1-16, wherein the at least one additional macromolecule is 1-10 macromolecules.

Embodiment 19. The method of any one of embodiments 1-18, wherein the first macromolecule is aberrantly expressed in a disease state.

Embodiment 20. The method of any one of embodiments 1-19, wherein a disease state level of association of the first macromolecule with the one or more target condensates is altered compared to a normal state level of association of the first macromolecule with the one or more target condensates.

Embodiment 21. The method of any one of embodiments 1-20, wherein one or more of the at least one additional macromolecule is aberrantly expressed in a disease state.

Embodiment 22. The method of any one of embodiments 1-21, wherein the first macromolecule is DNA or RNA.

Embodiment 23. The method of any one of embodiments 1-22, wherein one or more of the at least one additional macromolecule is DNA or RNA.

Embodiment 24. The method of any one of embodiments 1-21 or 23, wherein the first macromolecule is a protein.

Embodiment 25. The method of embodiment 24, wherein the first macromolecule comprises a mutation that alters the level of association of the first macromolecule with the one or more target condensates compared to a related protein that does not comprise the mutation.

Embodiment 26. The method of embodiment 24 or 25, wherein the first macromolecule is FUS or eIF3.

Embodiment 27. The method of any one of embodiments 1-26, wherein one or more of the at least one additional macromolecule is a protein.

Embodiment 28. The method of any one of embodiments 1-27, wherein one or more of the at least one additional macromolecule comprise a mutation that alters its corresponding level of association with the one or more target condensates compared to a related protein that does not comprise the mutation.

Embodiment 29. The method of any one of embodiments 1-28, wherein one or more of the at least one additional macromolecule is FUS, eIF3, G3BP1, FUS and G3BP1, or eIF3 and G3BP1.

Embodiment 30. The method of any one of embodiments 24-29, wherein the first macromolecule and/or one or more of the at least one additional macromolecule is a fusion protein.

Embodiment 31. The method of any one of embodiments 1-30, wherein the first macromolecule and/or one or more of the at least one additional macromolecule comprises a label.

Embodiment 32. The method of any one of embodiments 1-31, further comprising labeling the first macromolecule and/or one or more of the at least one additional macromolecule.

Embodiment 33. The method of embodiment 32, wherein the labeling comprises contacting the cellular composition with an antibody or antigen-binding fragment thereof comprising a label.

Embodiment 34. The method of any one of embodiments 31-33, wherein the label is a radioactive label, a colorimetric label, or a fluorescent label.

Embodiment 35. The method of any one of embodiments 1-34, wherein the cellular composition comprises a microorganism or an animal cell.

Embodiment 36. The method of embodiment 35, wherein the cellular composition comprises an animal cell.

Embodiment 37. The method of embodiment 36, wherein the animal cell that has one or more features of a neurodegenerative, proliferative, immunological, cardiac, or metabolic disease.

Embodiment 38. The method of any one of embodiments 35-37, wherein the animal cell is a HeLa cell, a HEK293 cell, an induced pluripotent stem cell (iPSC cell), a cardiomyocyte, a myocyte, a stem cell-derived cell, a neuron, a cancer cell, an immune cell, or an adipocyte.

Embodiment 39. The method of any one of embodiments 1-38, wherein the one or more target condensates is a cellular condensate.

Embodiment 40. The method of any one of embodiments 1-39, wherein the one or more target condensates is a nuclear condensate or a cytoplasmic condensate.

Embodiment 41. The method of embodiment 39, wherein the cellular condensate is a cleavage body, a p-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

Embodiment 42. The method of any one of embodiments 1-41, wherein the one or more target condensates is a single target condensate.

Embodiment 43. The method of embodiment 42, wherein the compound does not measurably alter one or more of: size of the target condensate, location of the target condensate, surface area of the target condensate, and dissolution of the target condensate.

Embodiment 44. The method of any one of embodiments 1-41, wherein the one or more target condensates is a plurality of target condensates.

Embodiment 45. The method of embodiment 44, wherein the plurality of target condensates is all or a subset of a class of condensates in a portion of the cellular composition.

Embodiment 46. The method of embodiment 44 or 45, wherein the plurality of target condensates is all or a subset of a class of condensates in a cell in the cellular composition.

Embodiment 47. The method of any one of embodiments 44-46, wherein the plurality of target condensates is all or a subset of a class of condensates in a portion of a cell in the cellular composition.

Embodiment 48. The method of embodiment 47, wherein the portion of the cell is the cytoplasm, the nucleus, or an organelle.

Embodiment 49. The method of any one of embodiments 45-48, wherein the class of condensates comprises condensates which comprise a specific macromolecule.

Embodiment 50. The method of any one of embodiments 45-49, wherein the class of condensates comprises condensates which are cleavage bodies; wherein the class of condensates comprises condensates which are p-granules; wherein the class of condensates comprises condensates which are histone locus bodies; wherein the class of condensates comprises condensates which are multivesicular bodies; wherein the class of condensates comprises condensates which are neuronal RNA granules; wherein the class of condensates comprises condensates which are nuclear gems; wherein the class of condensates comprises condensates which are nuclear pores; wherein the class of condensates comprises condensates which are nuclear speckles; wherein the class of condensates comprises condensates which are nuclear stress bodies; wherein the class of condensates comprises condensates which are nucleoli; wherein the class of condensates comprises condensates which are Oct1/PTF/transcription (OPT) domains; wherein the class of condensates comprises condensates which are paraspeckles; wherein the class of condensates comprises condensates which are perinucleolar compartments; wherein the class of condensates comprises condensates which are PML nuclear bodies; wherein the class of condensates comprises condensates which are PML oncogenic domains; wherein the class of condensates comprises condensates which are polycomb bodies; wherein the class of condensates comprises condensates which are processing bodies; wherein the class of condensates comprises condensates which are Sam68 nuclear bodies; wherein the class of condensates comprises condensates which are stress granules; or wherein the class of condensates comprises condensates which are splicing speckles.

Embodiment 51. The method of any one of embodiments 44-50, wherein the compound does not measurably alter one or more of: total number of the plurality of target condensates; size of the plurality of target condensates, location of the plurality of target condensates, surface area of the plurality of target condensates, and dissolution of the plurality of target condensates.

Embodiment 52. A method of identifying a plurality of compounds that preferentially affect the level, decrease the level, or increase the level of association of a first macromolecule with one or more target condensates, or that preferentially cause the first macromolecule to associate or disassociate with one or more target condensates, the method comprising performing the method of any one of embodiments 1-51 with a plurality of compounds.

Embodiment 53. The method of embodiment 52, further comprising identifying a characteristic that a subset or all of the identified compounds have in common in addition to ability to preferentially affect the level, decrease the level, or increase the level of association of the first macromolecule with the one or more target condensates, or the ability to preferentially cause the first macromolecule to associate or disassociate with one or more target condensates.

Embodiment 54. The method of embodiment 53, further comprising performing the method of any one of embodiments 1-51 for one or more additional test compounds that comprise the identified characteristic.

Embodiment 55. The method of embodiment 53 or 54, further comprising performing the method of any one of embodiments 1-51 for one or more additional test compounds that do not comprise the identified characteristic.

Embodiment 56. A method of identifying a compound characteristic associated with preferentially affecting the level, decreasing the level, or increasing the level of association of a first macromolecule with one or more target condensates, or with preferentially causing the first macromolecule to associate or disassociate with one or more target condensates, the method comprising: (a) performing the method of embodiment 52; and (b) identifying a characteristic that a subset or all of the identified compounds have in common in addition to the ability to preferentially affect the level, decrease the level, or increase the level of association of the first macromolecule with one or more target condensates, or the ability to preferentially cause the first macromolecule to associate or disassociate with one or more target condensates.

Embodiment 57. A method of designing a compound that preferentially affects the level, decreases the level, or increases the level of association of a first macromolecule with one or more target condensates, or that preferentially causes the first macromolecule to associate or disassociate with one or more target condensates, the method comprising: (a) performing the method of embodiment 52; (b) identifying a characteristic that a subset or all of the identified compounds have in common in addition to the ability to preferentially affect the level, decrease the level, or increase the level of association of the first macromolecule with one or more target condensates, or the ability to preferentially cause the first macromolecule to associate or disassociate with one or more target condensates; and (c) designing a compound that comprises the identified characteristic, thereby designing a compound that preferentially affects the level, decreases the level, or increases the level of association of the first macromolecule with one or more target condensates or preferentially causes the first macromolecule to associate or disassociate with one or more target condensates.

Embodiment 58. A method of identifying a compound useful for treating a disease in an individual in need thereof, the method comprising: performing the method of any one of embodiments 1-51, wherein the one or more target condensates is associated with the disease, and identifying the compound that preferentially affects the level, decreases the level, or increases the level of association of the first macromolecule with the one or more target condensates or that that preferentially causes the first macromolecule to associate or disassociate with one or more target condensates for being useful for treating the disease.

Embodiment 59. The method of embodiment 58, wherein the disease is a neurodegenerative, proliferative, immunological, cardiac, or metabolic disease.

Embodiment 60. A method of identifying a compound that preferentially affects a level of association of a first macromolecule with a first set of one or more target condensates, the method comprising: performing the method of any one of embodiments 1-51 with the first set of one or more target condensates; and performing the method of any one of embodiments 1-51 with a second set of one or more target condensates wherein the compound preferentially affects the level of association of the first macromolecule with the first set of one or more target condensates if the compound preferentially affects the level of association of the first macromolecule with the first set of one or more target condensates more than the compound preferentially affects the level of association of the first macromolecule with the second set of one or more target condensates.

Embodiment 61. The method of embodiment 60, wherein the compound does not affect the level of association of the first macromolecule with the second set of one or more target condensates.

Embodiment 62. A method of identifying a compound that preferentially increases a level of association of a first macromolecule with a first set of one or more target condensates, the method comprising: performing the method of any one of embodiments 1-51 with the first set of one or more target condensates; and performing the method of any one of embodiments 1-51 with a second set of one or more target condensates, wherein the compound preferentially increases the level of association of the first macromolecule with the first set of one or more target condensates if the compound preferentially increases the level of association of the first macromolecule with the first set of one or more target condensates more than the compound preferentially increases the level of association of the first macromolecule with the second set of one or more target condensates.

Embodiment 63. The method of embodiment 62, wherein the compound does not increase the level of association of the first macromolecule with the second set of one or more target condensates.

Embodiment 64. A method of identifying a compound that preferentially decreases a level of association of a first macromolecule with a first set of one or more target condensates, the method comprising: performing the method of any one of embodiments 1-51 with the first set of one or more target condensates; and performing the method of any one of embodiments 1-51 with a second set of one or more target condensates, wherein the compound preferentially decreases the level of association of the first macromolecule with the first set of one or more target condensates if the compound preferentially decreases the level of association of the first macromolecule with the first set of one or more target condensates more than the compound preferentially decreases the level of association of the first macromolecule with the second set of one or more target condensates.

Embodiment 65. The method of embodiment 64, wherein the compound does not decrease the level of association of the first macromolecule with the second set of one or more target condensates.

Embodiment 66. A method of identifying a compound that preferentially causes a first macromolecule to associate with a first set of one or more target condensates, the method comprising: performing the method of any one of embodiments 1-51 with the first set of one or more target condensates; and performing the method of any one of embodiments 1-51 with a second set of one or more target condensates, wherein the compound preferentially causes the first macromolecule to associate with the first set of one or more target condensates if the compound preferentially causes the first macromolecule to associate with the first set of one or more target condensates more than the compound preferentially causes the first macromolecule to associate with the second set of one or more target condensates.

Embodiment 67. A method of identifying a compound that preferentially causes a first macromolecule to disassociate with a first set of one or more target condensates, the method comprising: performing the method of any one of embodiments 1-51 with the first set of one or more target condensates; and performing the method of any one of embodiments 1-51 with a second set of one or more target condensates, wherein the compound preferentially causes the first macromolecule to disassociate with the first set of one or more target condensates if the compound preferentially causes the first macromolecule to associate with the first set of one or more target condensates more than the compound preferentially causes the first macromolecule to associate with the second set of one or more target condensates.

Embodiment 68. The method of any one of embodiments 60-67, wherein the first and/or second set of one or more target condensates is a cellular condensate.

Embodiment 69. The method of any one of embodiments 60-68, wherein the first and/or second set of one or more target condensates is a nuclear condensate or a cytoplasmic condensate.

Embodiment 70. The method of any one of embodiments 60-68, wherein the first and/or second set of one or more target condensates is a cleavage body, a p-granule, a histone locus body, a multivesicular body, a neuronal RNA granule, a nuclear gem, a nuclear pore, a nuclear speckle, a nuclear stress body, a nucleolus, a Oct1/PTF/transcription (OPT) domain, a paraspeckle, a perinucleolar compartment, a PML nuclear body, a PML oncogenic domain, a polycomb body, a processing body, a Sam68 nuclear body, a stress granule, or a splicing speckle.

Embodiment 71. The method of any one of embodiments 60-70, wherein the first and/or second set of one or more target condensates is a single target condensate.

Embodiment 72. The method of any one of embodiments 60-70, wherein the first and/or second set of one or more target condensates is a plurality of target condensates.

Embodiment 73. The method of embodiment 60-70 or 72, wherein the first and/or second set of one or more target condensates is all or a subset of a class of condensates in a portion of the cellular composition.

Embodiment 74. The method of any one of embodiments 60-70 or 72-73, wherein the first and/or second set of one or more target condensates is all or a subset of a class of condensates in a cell in the cellular composition.

Embodiment 75. The method of any one of embodiments 60-70 or 72-74, wherein the first and/or second set of one or more target condensates is all or a subset of a class of condensates in a portion of a cell in the cellular composition.

Embodiment 76. The method of embodiment 75, wherein the portion of the cell is the cytoplasm, the nucleus, or an organelle.

Embodiment 77. The method of any one of embodiments 73-76, wherein the class of condensates comprises condensates which comprise a specific macromolecule.

Embodiment 78. The method of any one of embodiments 73-77, wherein the class of condensates comprises condensates which are cleavage bodies; wherein the class of condensates comprises condensates which are p-granules; wherein the class of condensates comprises condensates which are histone locus bodies; wherein the class of condensates comprises condensates which are multivesicular bodies; wherein the class of condensates comprises condensates which are neuronal RNA granules; wherein the class of condensates comprises condensates which are nuclear gems; wherein the class of condensates comprises condensates which are nuclear pores; wherein the class of condensates comprises condensates which are nuclear speckles; wherein the class of condensates comprises condensates which are nuclear stress bodies; wherein the class of condensates comprises condensates which are nucleoli; wherein the class of condensates comprises condensates which are Oct1/PTF/ transcription (OPT) domains; wherein the class of condensates comprises condensates which are paraspeckles; wherein the class of condensates comprises condensates which are perinucleolar compartments; wherein the class of condensates comprises condensates which are PML nuclear bodies; wherein the class of condensates comprises condensates which are PML oncogenic domains; wherein the class of condensates comprises condensates which are polycomb bodies; wherein the class of condensates comprises condensates which are processing bodies; wherein the class of condensates comprises condensates which are Sam68 nuclear bodies; wherein the class of condensates comprises condensates which are stress granules; or wherein the class of condensates comprises condensates which are splicing speckles.

Embodiment 79. The method of any one of embodiments 73-78, wherein the class of the first set of one or more target condensates is the same as the class of second set of one or more target condensates.

Embodiment 80. The method of any one of embodiments 73-78, wherein the class of the first set of one or more target condensates is different than the class of second set of one or more target condensates.

Embodiment 81. The method of any one of embodiments 60-80, wherein the first set of one or more target condensates is in the same cellular composition as the second set of one or more target condensates.

Embodiment 82. The method of any one of embodiments 60-81, wherein the cellular composition comprises a cell comprising the first set of condensate of one or more target condensates and the second set of one or more target condensates.

Embodiment 83. The method of any one of embodiments 60-80, wherein the first set of condensate of one or more target condensates is in a first cellular composition, and the second set of one or more target condensates is in a second cellular composition.

Embodiment 84. The method of any one of embodiments 60-83, wherein the first set of condensate of one or more target condensates are in a cell in the cellular composition, and the cell has one or more features of a disease.

Embodiment 85. The method of embodiment 84, wherein the disease is a neurodegenerative, proliferative, immunological, cardiac, or metabolic disease.

Embodiment 86. A method of identifying a plurality of compounds that preferentially affect the level, decrease the level, or increase the level of association of a first macromolecule with a first set of one or more target condensates, or that preferentially cause the first macromolecule to associate or disassociate with the first set of one or more target condensates, the method comprising performing the method of any one of embodiments 60-85 with a plurality of compounds.

Embodiment 87. The method of embodiment 86, further comprising identifying a characteristic that a subset or all of the identified compounds have in common in addition to ability to preferentially affect the level, decrease the level, or increase the level of association of the first macromolecule with the first set of one or more target condensates, or the ability to preferentially cause the first macromolecule to associate or disassociate with the first set of one or more target condensates.

Embodiment 88. The method of embodiment 87, further comprising performing the method of any one of embodiments 60-85 for one or more additional test compounds that comprise the identified characteristic.

Embodiment 89. The method of embodiment 87 or 88, further comprising performing the method of any one of embodiments 60-85 for one or more additional test compounds that do not comprise the identified characteristic.

Embodiment 90. A method of identifying a compound characteristic associated with preferentially affecting the level, decreasing the level, or increasing the level of association of a first macromolecule with a first set of one or more target condensates, or with preferentially causing the first macromolecule to associate or disassociate with the first set of one or more target condensates, the method comprising: (a) performing the method of embodiment 86; and (b) identifying a characteristic that a subset or all of the identified compounds have in common in addition to the ability to preferentially affect the level, decrease the level, or increase the level of association of the first macromolecule with the first set of one or more target condensates, or the ability to preferentially cause the first macromolecule to associate or disassociate with the first set of one or more target condensates.

Embodiment 91. A method of designing a compound that preferentially affects the level, decreases the level, or increases the level of association of a first macromolecule with a first set of one or more target condensates, or that preferentially causes the first macromolecule to associate or disassociate with the first set of one or more target condensates, the method comprising: (a) performing the method of embodiment 86; (b) identifying a characteristic that a subset or all of the identified compounds have in common in addition to the ability to preferentially affect the level, decrease the level, or increase the level of association of the first macromolecule with the first set of one or more target condensates, or the ability to preferentially cause the first macromolecule to associate or disassociate with the first set of one or more target condensates; and (c) designing a compound that comprises the identified characteristic, thereby designing a compound that preferentially affects the level, decreases the level, or increases the level of association of the first macromolecule with the first set of one or more target condensates or preferentially causes the first macromolecule to associate or disassociate with the first set of one or more target condensates.

Embodiment 92. A method of identifying a compound useful for treating a disease in an individual in need thereof, the method comprising: performing the method of any one of embodiments 60-85, wherein the first set of one or more target condensates is associated with the disease, and identifying the compound that preferentially affects the level, decreases the level, or increases the level of association of the first macromolecule with the first set of one or more target condensates or that that preferentially causes the first macromolecule to associate or disassociate with the first set of one or more target condensates for being useful for treating the disease.

Embodiment 93. The method of embodiment 92, wherein the disease is a neurodegenerative, proliferative, immunological, cardiac, or metabolic disease.

EXAMPLES

Example 1

Screening for Compounds that Cause Alterations in Condensate Protein Levels

Stress granules are condensates that form in the cytoplasm of cells under stress. Multiple proteins are known to be concentrated in stress granules, including FUS, eukaryotic initiation factor 3 (eIF3), and G3BP1. FUS is involved in pre-mRNA maturation, and various mutations in FUS have been associated with ALS. Although FUS is found in stress granules, it is not believed to be critical for formation of stress granules. Like FUS, eIF3 is also not believed to be critical for formation of stress granules. As the name indicates, eIF3 is a eukaryotic initiation factor, but it is also involved in translational recycling. By contrast, G3BP1 is believed to initiate formation of stress granules and is potentially critical to maintaining their structure. G3BP1 is an RNA binding protein and an element of the Ras signaling transduction pathway. These three proteins were tracked within cells to determine if compounds could preferentially exclude one of these proteins from stress granules without dissolving the stress granule.

Methods

Three cell lines (HeLa Kyoto, HeLa comprising a bacterial artificial chromosome (BAC) encoding FUS-GFP, and induced pluripotent stem cells (iPS) expressing FUS-GFP) were separately grown in culture. 1200 compounds from a compound library were exposed individually at concentrations of 1 µM, 5 µM, or 25 µM to one of the cell lines for one hour. For some compounds, this procedure was repeated for one or both of the other cell lines. Cells that were not exposed to the compounds (DMSO-only vehicle treatment) were used as controls. The cells were then exposed to arsenate stress for 1 hour to stimulate the formation of stress granules, using a final concentration of 2 mM Potassium Arsenate (Sigma A6631, diluted in PBS).

After stress treatment, the cells were fixed with a final concentration of 3.7% Formaldehyde (FA) for 15 minutes at room temperature. Subsequently, cells were washed using a plate washer, permeabilized (10 min at RT using 0.1% Triton X/PBS) and blocked (30 min with 0.2% Fish skin gelatin/PBS). For cells expressing FUS-GFP, GFP fluorescence was observed directly. For the other protein markers of interest a combination of anti-FUS (Sigma AMAb90549; 1:500), anti-eIF3 (Santa Cruz sc-137214; 1:500), and anti-G3BP1 (Invitrogen PAS-29455; 1:4000) antibodies and appropriate secondary antibodies (Life Technologies; Alexa 594 and 647) was applied to visualize FUS, eIF3, and G3BP1 protein in the cells.

A spinning disk confocal microscope was used to acquire images of the samples using confocal fluorescence at 405/488/561/640 nm. 40× air objective lenses were used to capture the images. The gain was set to 1.4 and binning to 1. The exposure times were adjusted to the fluorescence emission intensity specific for each label. Exposure times ranged from 100-300 ms. Appropriate filter settings were used, matching the excitation and emission spectra of the label. Image acquisition was automated, and the resulting data were analyzed using KNIME (Berthold et al., 2008, Data Analysis, Machine Learning and Applications. Studies in Classification, Data Analysis, and Knowledge Organization. Springer, Berlin, Heidelberg) and CellProfiler (Carpenter et al., 2006, Genome Biol 7:R100). Twenty-five imaging parameters were extracted for each image, including marker signal droplet count, area, shape, etc. For each imaging parameter, the Z' factor for the entire plate was calculated according to the following formula:

$$Z'=1-[3*(SD(pos)+SD(neg))/(Avg(pos)-Avg(neg))]$$

where SD(pos) is the standard deviation of the positive control, SD(neg) is the standard deviation of the negative control, Avg(pos) is the average of the positive control and Avg(neg) is the average of the negative control.

In addition, z-scores were calculated for every test compound using the formula:

$$z=(x-\underline{x})/S$$

where $\underline{x}$ is the mean of the sample, and S is the standard deviation of the sample. Compounds were classified as "hits" if the plate Z' was at least 0.1, and if at least two imaging parameters had a z-score≥3.0 standard deviations from the median parameter value.

Results

Figure 2:
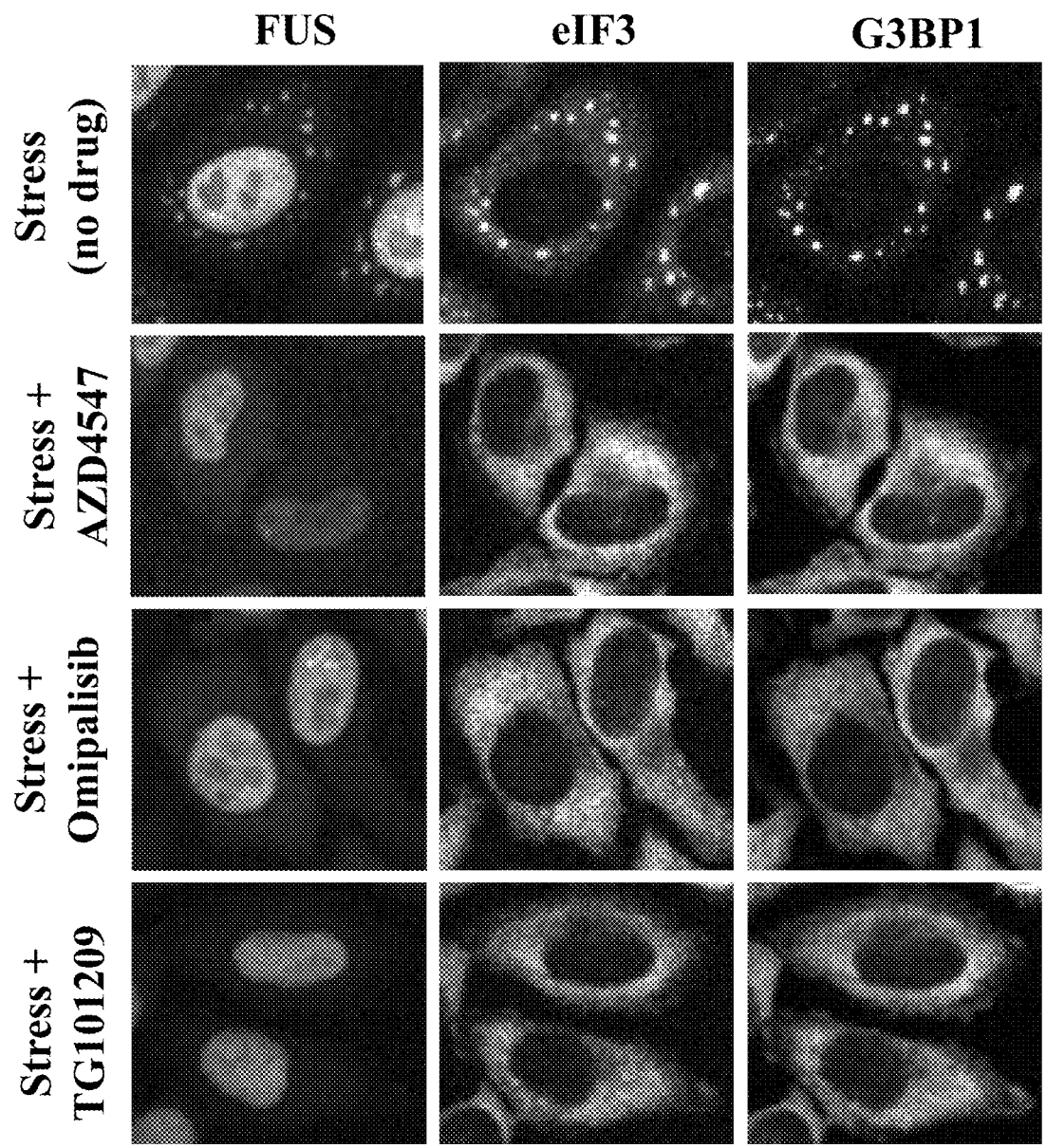
FIG. 2 is fluorescent micrographs showing the levels of FUS, eIF3, and G3BP1 in stressed cells with or without treatment with AZD4547, Omipalisib, and TG101209.
Figure 3:
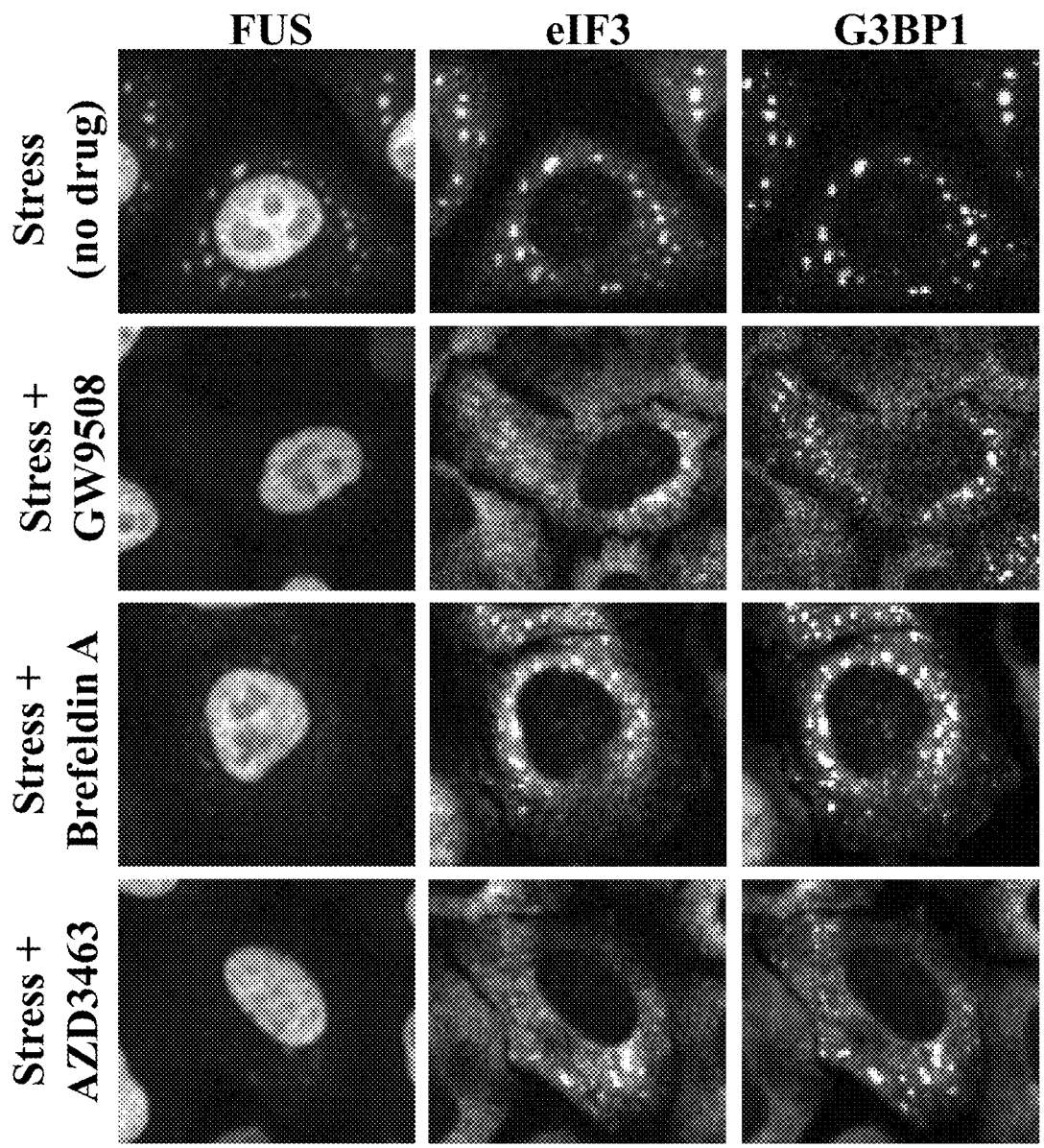
FIG. 3 is fluorescent micrographs showing the levels of FUS, eIF3, and G3BP1 in stressed cells with or without treatment with GW9508, Brefeldin A, AZD3463 and Ketanserin.
Figure 4:
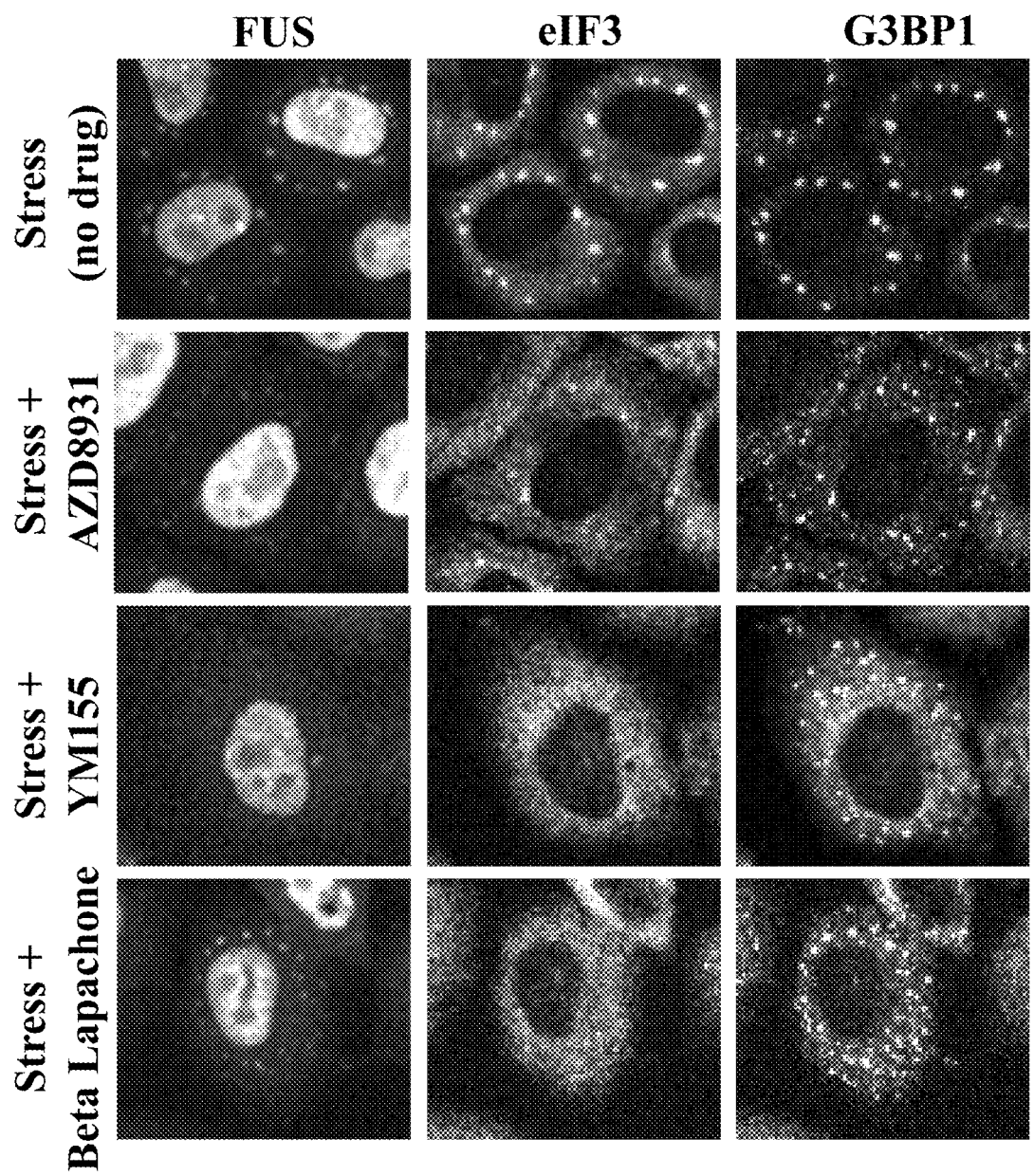
FIG. 4 is fluorescent micrographs showing the levels of FUS, eIF3, and G3BP1 in stressed cells with or without treatment with AZD8931, YM155 and Beta-Lapachone.
Figure 5:
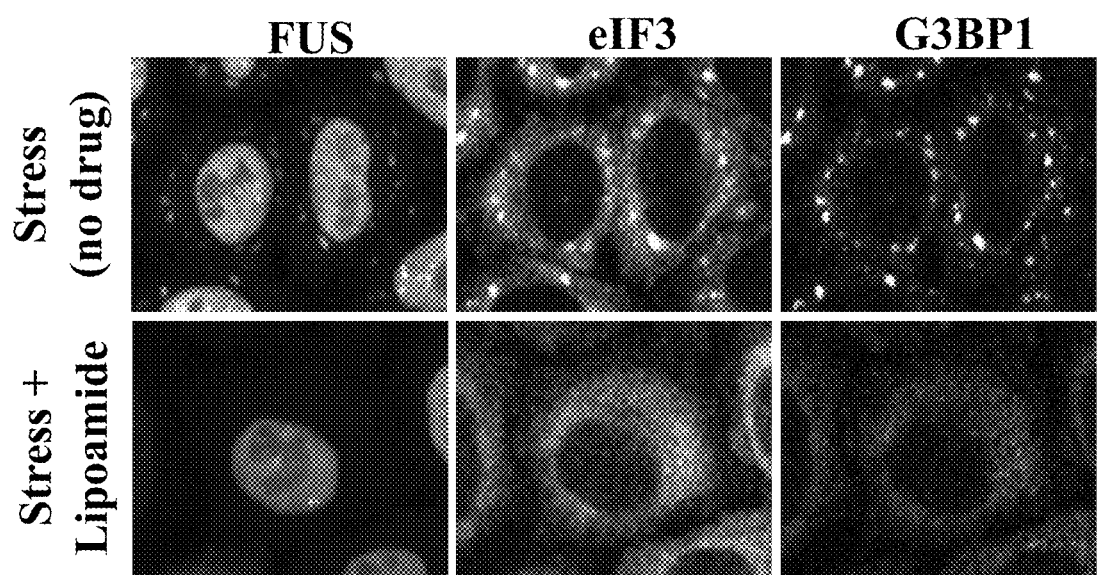
FIG. 5 is fluorescent micrographs showing the levels of FUS, eIF3, and G3BP1 in stressed cells with or without treatment with lipoamide.
Figure 6:
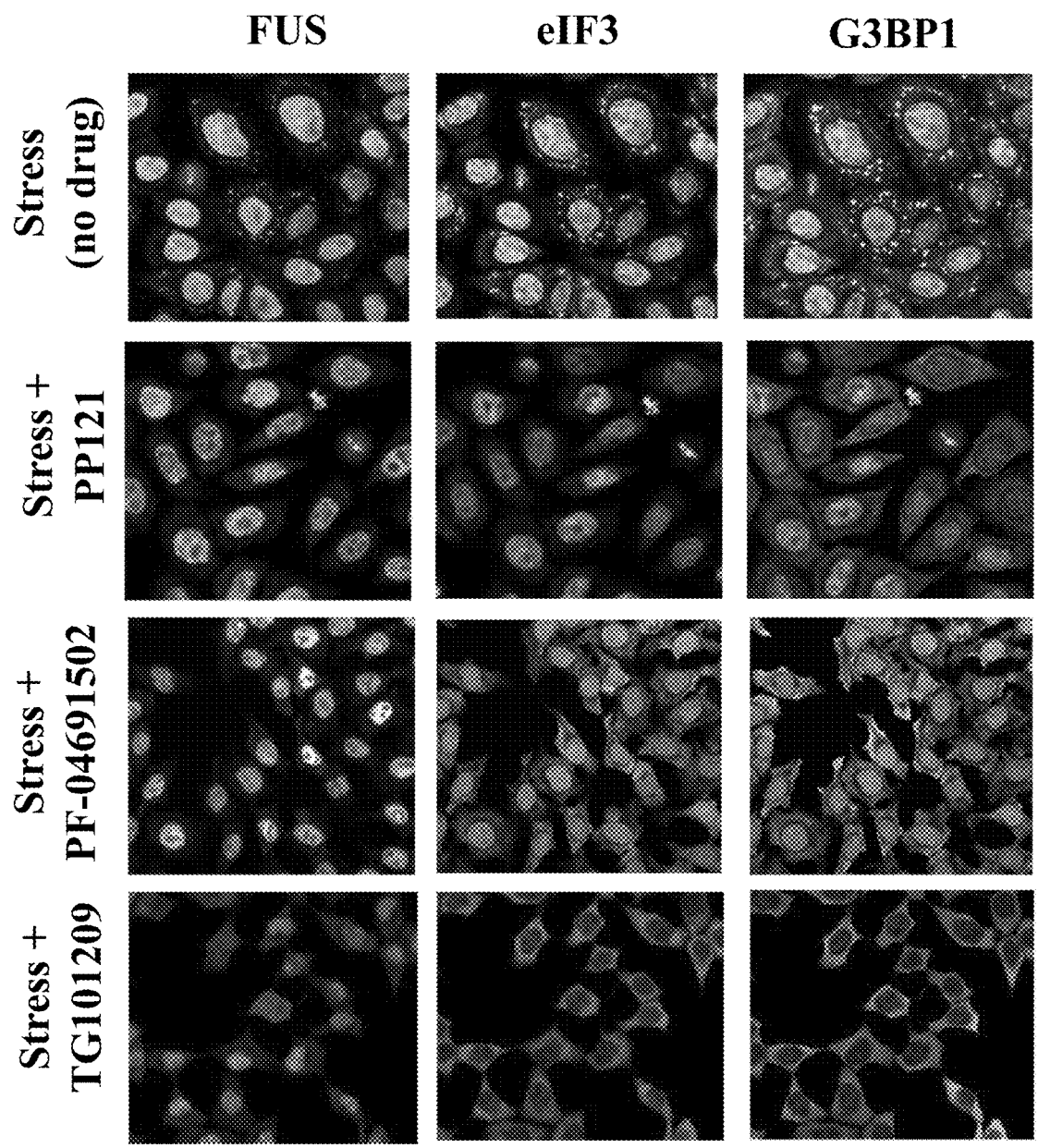
FIG. 6 is fluorescent micrographs showing the levels of FUS, eIF3, and G3BP1 in stressed cells with or without treatment with P121, PF-04691502, and TG101209.
Figure 7:
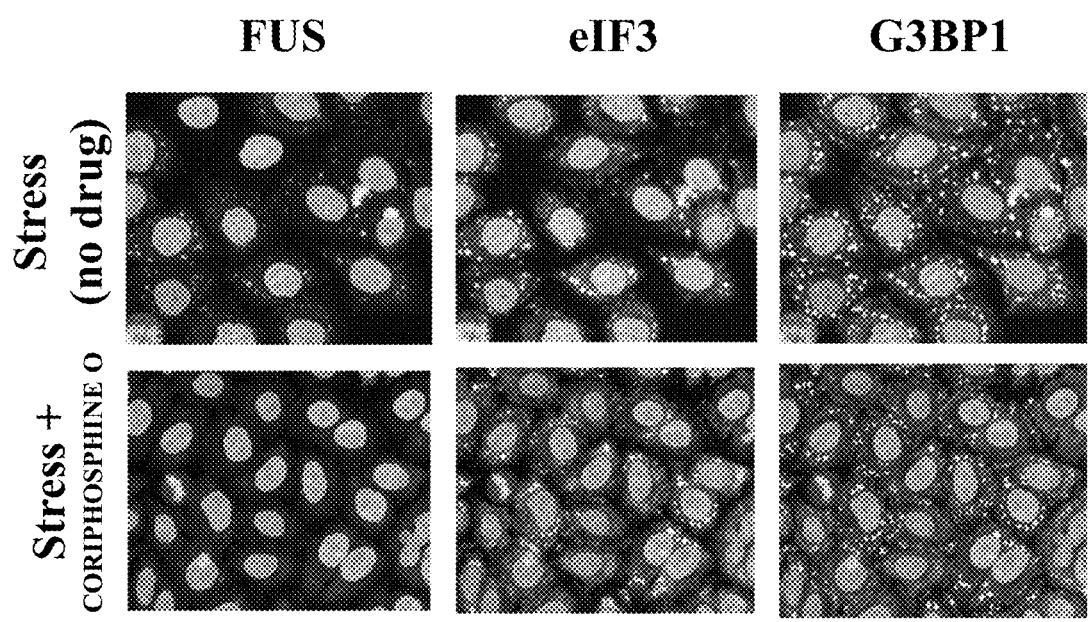
FIG. 7 is fluorescent micrographs showing the levels of FUS, eIF3, and G3BP1 in stressed cells with or without treatment with Coriphosphine O.
Figure 8:
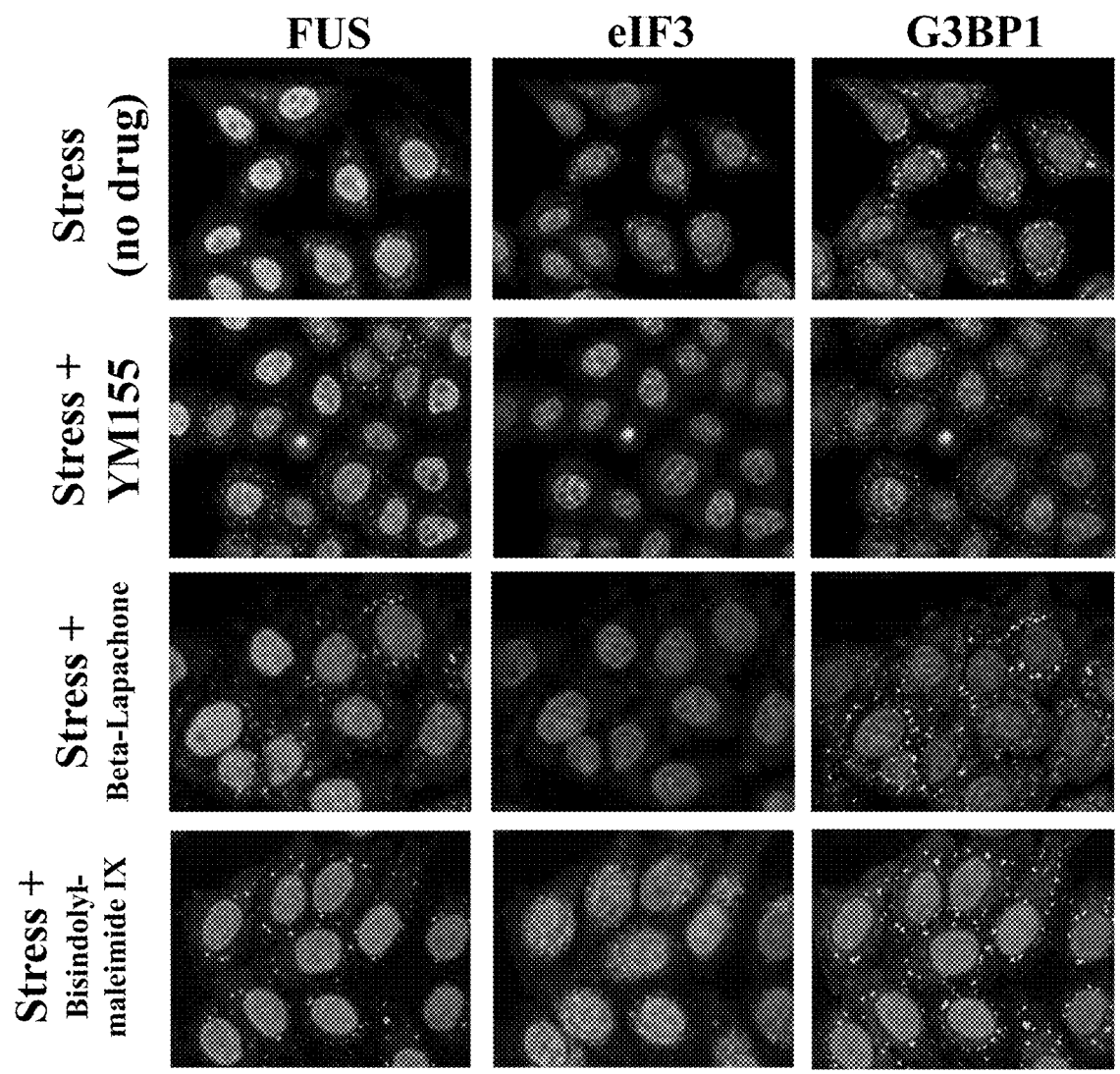
FIG. 8 is fluorescent micrographs showing the levels of FUS, eIF3, and G3BP1 in stressed cells with or without treatment with YM155, Beta-Lapachone, and Bisindolylmaleimide IX.
Figure 9:
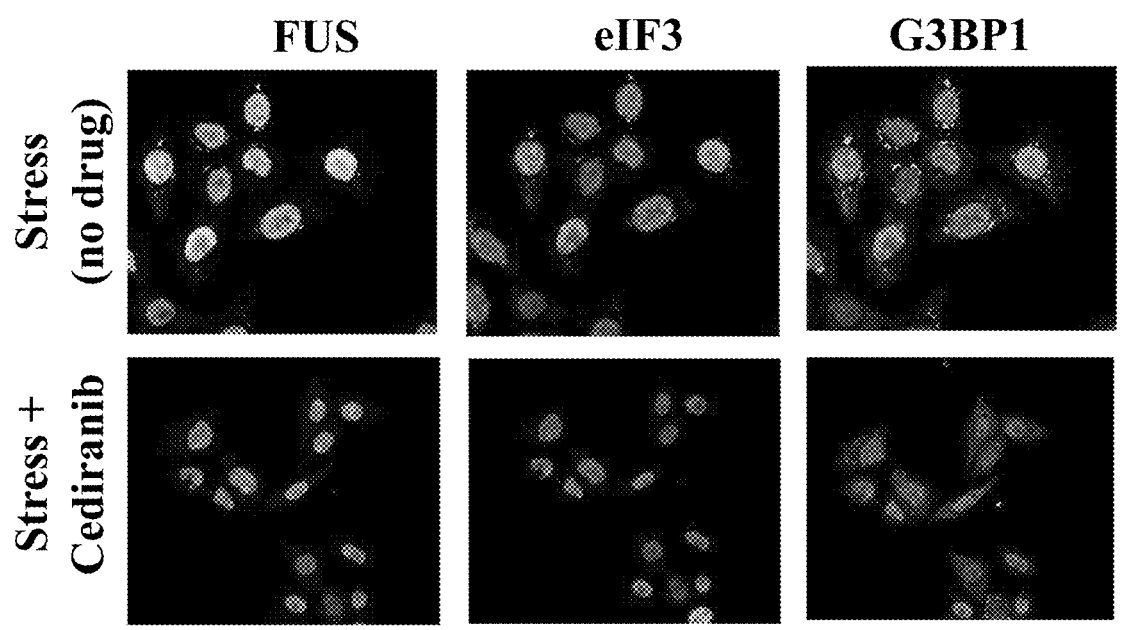
FIG. 9 is fluorescent micrographs showing the levels of FUS, eIF3, and G3BP1 in stressed cells with or without treatment with Cediranib.
Figure 10:
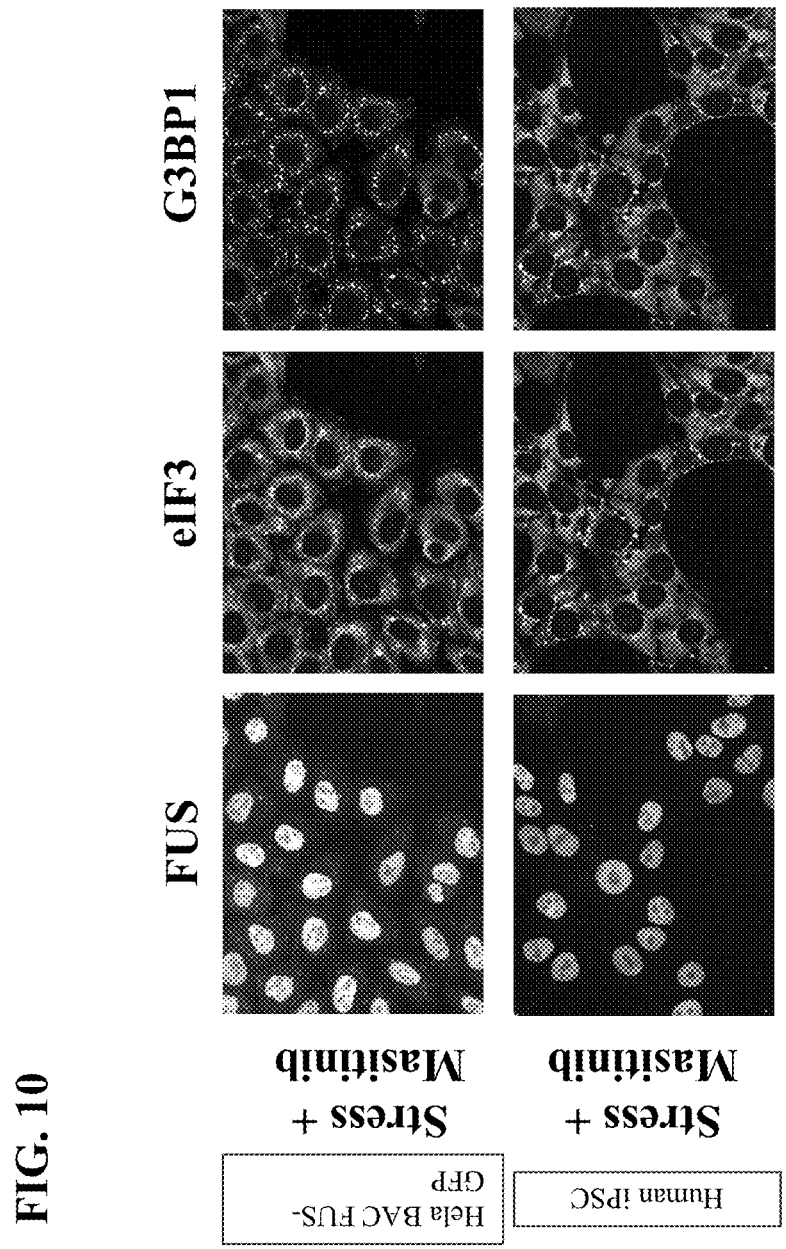
FIG. 10 is fluorescent micrographs showing the levels of FUS, eIF3, and G3BP1 in stressed HeLa cells carrying BAC FUS-GFP and stressed human iPSC cells with or without treatment with Matisinib.

In the absence of the compounds, FUS, eIF3, and G3BP1 all appeared to co-localize into the same condensates in all three cell lines tested when stressed, see FIGS. 1-4, no compound treatment. Additionally, many of the compounds did not appear to alter the localization or the level of FUS, eIF3, and G3BP1. Several compounds were found that appeared to dissolve the stress granules entirely, exemplary images shown in FIGS. 1 and 2 and compounds used in FIGS. 1 and 2 are shown in Table 1. No compounds were found that selectively excluded G3BP1 from the stress granules. Whenever G3BP1 was found to not be localized to stress granules after treatment with the compound, neither FUS nor eIF3 were found to be localized to the stress granules after treatment. By contrast, at least four compounds were found that caused partial or complete exclusion of FUS from stress granules, but did not reduce the level of either other protein assayed or appear to dissolve the stress granule, see FIG. 3 for exemplary images and compounds used in FIG. 3 are shown in Table 1. Also in contrast to G3BP1, at least three compounds were found that caused partial or complete exclusion of eIF3 from stress granules, but did not reduce the level of either other protein assayed or appear to dissolve the stress granule, see FIG. 4 for exemplary images and compounds used in FIG. 4 are shown in Table 1.

TABLE 1
Selective and Non-Selective Condensate Disrupters
| | | |
|---|---|---|
| Lipoamide | Non-selective | 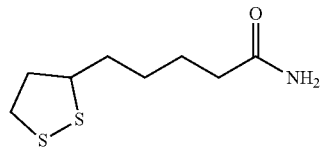 [SMILES: NC(=O)CCCCC1CCSS1] |
| AZD4547 | Non-selective | 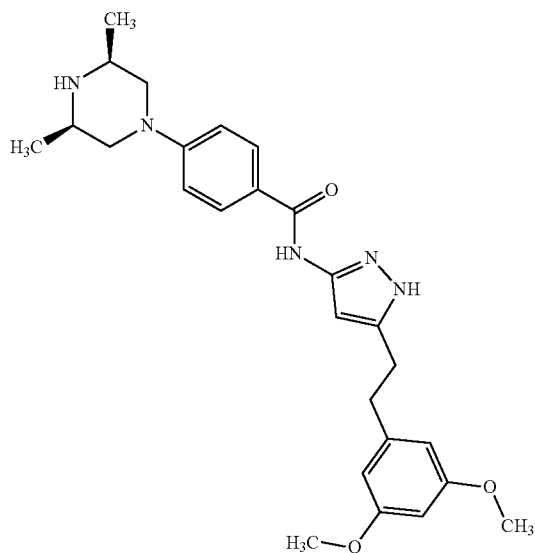 |
| Omipalisib | Non-selective | 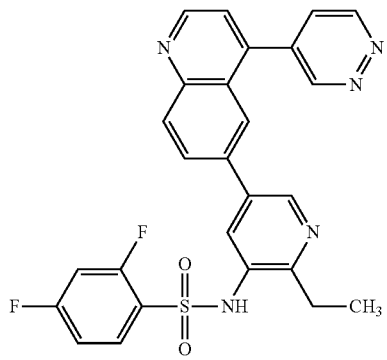 [SMILES: CCc1ncc(-c2ccc3nccc(-c4ccnnc4)c3c2)cc1NS(=O)(=O)c1ccc(F)cc1F] |
| TG101209 | Non-selective | 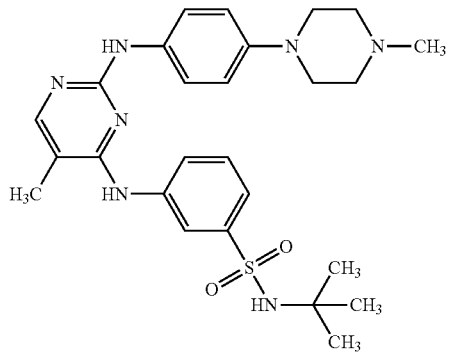 [SMILES: Cc1cnc(Nc2ccc(N3CCN(C)CC3)cc2)nc1Nc1cccc(S(=O)(=O)NC(C)(C)C)c1] |

TABLE 1-continued
Selective and Non-Selective Condensate Disrupters
GW9508  FUS-selective
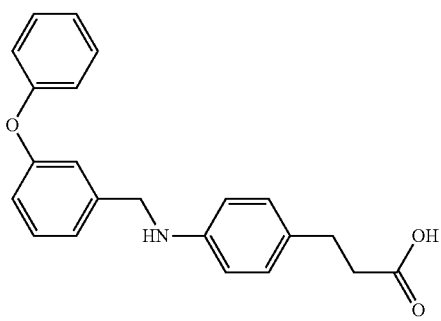 [SMILES: O=C(O)CCc1ccc(NCc2cccc(Oc3ccccc3)c2)cc1]
Brefeldin A  FUS-selective
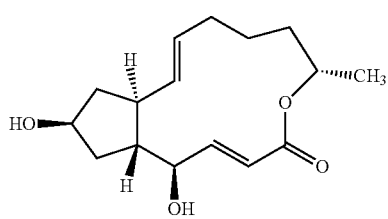 [SMILES: C[C@H]1CCC/C=C/[C@@H]2C[C@H](O)C[C@H]2[C@H](O)/C=C/C(=O)O1]
AZD3463  FUS-selective
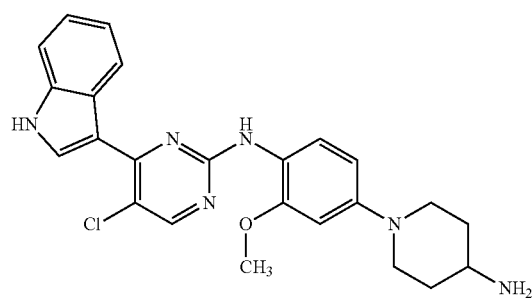 [SMILES: COc1cc(N2CCC(N)CC2)ccc1Nc1ncc(Cl)c(-c2c[nH]c3ccccc23)n1]
Ketanserin  FUS-selective
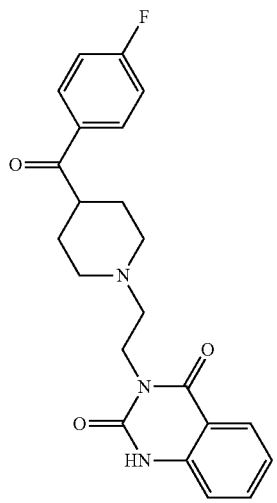 [SMILES: O=C(c1ccc(F)cc1)C1CCN(CCn2c(=O)[nH]c3ccccc3c2=O)CC1]
AZD8931  eIF3-selective
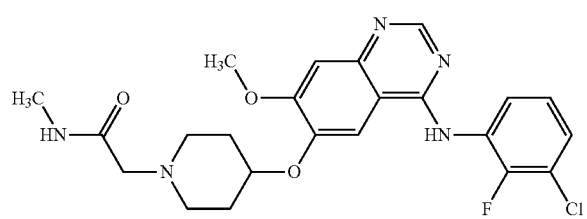 [SMILES: CNC(=O)CN1CCC(Oc2cc3c(Nc4cccc(Cl)c4F)ncnc3cc2OC)CC1]

TABLE 1-continued

Selective and Non-Selective Condensate Disrupters

YM155 (Sepantronium Bromide) — eIF3-selective

Beta-Lapachone — eIF3-selective

Example 2

This example demonstrates a method of identifying compounds having macromolecule specificity and tissue specificity.

Methods

The methods used in this example were similar to those discussed in Example 1. In brief, three cell lines (HeLa Kyoto, HeLa comprising a bacterial artificial chromosome (BAC) encoding FUS-GFP, and induced pluripotent stem cells (iPS) expressing FUS-GFP) were separately grown in culture. 1200 compounds from a compound library were exposed individually at concentrations of 1 µM, 5 µM, or 25 µM to one of the cell lines for one hour. For some compounds, this procedure was repeated for one or both of the other cell lines. Hits from the screen were further characterized by compound treatments at 0.0021 µM, 0.0062 µM, 0.017 µM, 0.065 µM, 0.131 µM, 0.196 µM, 0.52 µM, 3.3 µM, 10 µM, and 30 µM, with the resulting dose-response data analyzed using the four parameter logistic equation to calculate the potency (similar to $IC_{50}$) of the compound. Cells that were not exposed to the compounds (DMSO-only vehicle treatment) were used as controls. The cells were then exposed to arsenate stress for 1 hour to stimulate the formation of stress granules, using a final concentration of 2 mM Potassium Arsenate (Sigma A6631, diluted in PBS).

After stress treatment, the cells were fixed with a final concentration of 3.7% Formaldehyde (FA) for 15 minutes at room temperature. Subsequently, cells were washed using a plate washer, permeabilized (10 min at RT using 0.1% Triton X/PBS) and blocked (30 min with 0.2% Fish skin gelatin/PBS). For cells expressing FUS-GFP, GFP fluorescence was observed directly. For the other protein markers of interest a combination of anti-FUS (Sigma AMAb90549; 1:500), anti-eIF3 (Santa Cruz sc-137214; 1:500), and anti-G3BP1 (Invitrogen PAS-29455; 1:4000) antibodies and appropriate secondary antibodies (Life Technologies; Alexa 594 and 647) was applied to visualize FUS, eIF3, and G3BP1 protein in the cells.

A spinning disk confocal microscope was used to acquire images of the samples using confocal fluorescence at 405/488/561/640 nm. 40× (primary screen) and 20× (potency testing) air objective lenses were used to capture the images. The gain was set to 1.4 and binning to 1. The exposure times were adjusted to the fluorescence emission intensity specific for each label. Exposure times ranged from 100-300 ms. Appropriate filter settings were used, matching the excitation and emission spectra of the label. Image acquisition was automated, and the resulting data were analyzed using KNIME (Berthold et al., 2008, Data Analysis, Machine Learning and Applications. Studies in Classification, Data Analysis, and Knowledge Organization. Springer, Berlin, Heidelberg), CellProfiler (Carpenter et al., 2006, Genome Biol 7:R100); or, for potency testing, data were analyzed using Harmony (PerkinElmer, Waltham Mass.) and Vault (Collaborative Drug Discovery, Burlingame Calif.). Twenty-five imaging parameters were extracted for each image, including marker signal droplet count, area, shape, etc. For each imaging parameter, the Z' factor for the entire plate was calculated according to the following formula:

$$Z'=1-[3*(SD(pos)+SD(neg))/(Avg(pos)-Avg(neg))]$$

where SD(pos) is the standard deviation of the positive control, SD(neg) is the standard deviation of the negative control, Avg(pos) is the average of the positive control and Avg(neg) is the average of the negative control.

In addition, z-scores were calculated for every test compound using the formula:

$$z=(x-\bar{x})/S$$

where $\bar{x}$ is the mean of the sample, and S is the standard deviation of the sample.

Compounds were classified as "hits" if the plate Z' was at least 0.1, and if at least two imaging parameters had a z-score≥3.0 standard deviations from the median parameter value.

Potency calculations for screening hits (similar to inhibition concentration 50; $IC_{50}$) were made using measured value of number of cytoplasmic drops per cell and the the four parameter logistic equation for analysis. Briefly, the % effect of compound treatment was first plotted as a function of the log 10(molar concentration) of compound. Next, the data was fit via least squares minimization to the 4 parameter logistic equation to calculate the 50% inhibition constant ($IC_{50}$).

% effect=(measured value−negative control)/(positive control−negative control)*100

Logistic equation:
y=lower+(upper−lower)/(1+10^((log $IC_{50}$−x)*HS))
wherein:
x=$\log_{10}$(molar concentration of compound)
lower=lower baseline of the dose response
upper=upper baseline of the dose response
HS=the Hill Slope of the dose response Results In the absence of the compounds, FUS, eIF3, and G3BP1 all appeared to co-localize into the same condensates in all three cell lines tested when stressed (see FIGS. 5-10, no compound treatment). As shown in FIGS. 5-10, many of the compounds did not appear to alter the localization or the level of FUS, eIF3, and G3BP1, and certain compounds were found that appeared to dissolve the stress granules entirely. Compounds used in FIGS. 5-10 and their macromolecule specificity are shown in Table 2. No compounds were found that selectively excluded G3BP1 from the stress granules. Whenever G3BP1 was found to not be localized to stress granules after treatment with the compound, neither FUS nor eIF3 were found to be localized to the stress granules after treatment. By contrast, a compound was found that caused exclusion of FUS from stress granules, but did not reduce the level of either other proteins assayed or appear to dissolve the stress granule (see, e.g., FIG. 7). Also in contrast to G3BP1, at least three compounds were found that caused partial or complete exclusion of eIF3 from stress granules, but did not reduce the level of either other protein assayed or appear to dissolve the stress granule (see, e.g., FIG. 8). One compound was found that caused exclusion of both eIF3 and FUS, but not G3BP1 (see FIG. 9). One compound was also observed that excluded FUS selectively in human iPSC cells but not in HeLa BAC FUS-GFP cells (see FIG. 10).

Figure 11:
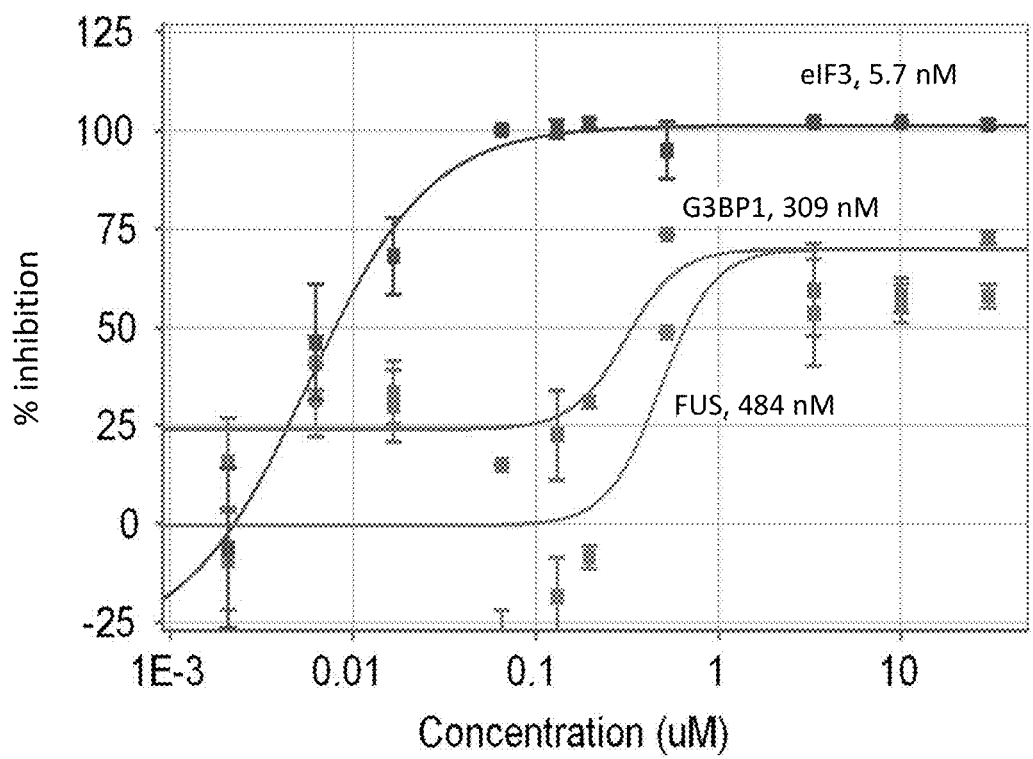
FIG. 11 is a plot of dose-response curves for FUS, eIF3, and G3BP1 in stress granules of stressed HeLa cells carrying BAC FUS-GFP treated with YM155.

Compound selectivity for exclusion of a given protein relative to other proteins can be further quantified by calculating the potency for the exclusion of a specific protein relative to others (similar to inhibition constant 50% ($IC_{50}$)). FIG. 11 contains example dose-dependent curves and potency values for YM155, demonstrating the exclusion of eIF3 at lower concentration of compound relative to FUS and G3BP1. This information provides additional means for comparison, e.g., dose-dependent curves and/or potency values, to identify compound specificity.

TABLE 2

| | Selective and Non-Selective Condensate Disrupters | |
|---|---|---|
| Compound | Selectivity | Molecular Structure |
| Lipoamide | Non-selective | |
| PP121 | Non-selective | 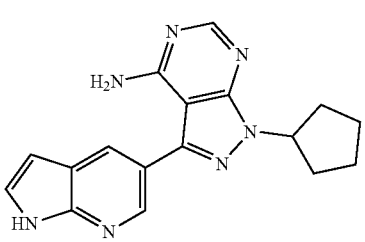 [SMILES: Nc1ncnc2c1c(-c1cnc3[nH]ccc3c1)nn2C1CCCC1] |
| PF-04691502 | Non-selective | 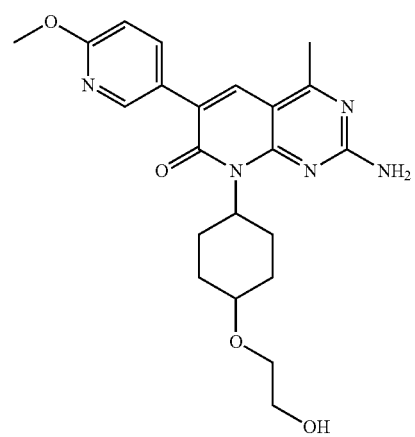 [SMILES: COc1ccc(-c2cc3c(C)nc(N)nc3n(C3CCC(OCCO)CC3)c2=O)cn1] |
| TG101209 | Non-selective | |
| Coriphosphine O | FUS-selective | 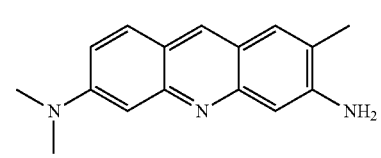 |

TABLE 2-continued
Selective and Non-Selective Condensate Disrupters
| Compound | Selectivity | Molecular Structure |
| --- | --- | --- |
| YM155 (Sepantronium Bromide) | eIF3-selective | |
| Beta-Lapachone | eIF3-selective | |
| Bisindolylmaleimide IX | eIF3-selective | 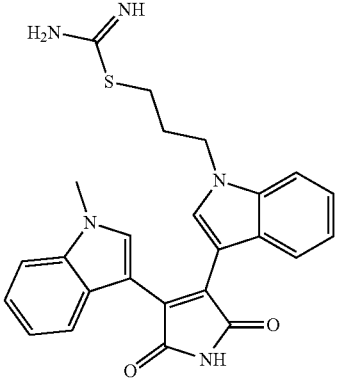 [SMILES: Cn1cc(C2=C(c3cn(CCCSC(=N)N)c4ccccc34)C(=O)NC2=O)c2ccccc21] |
| Cediranib | eIF3 and FUS-selective | 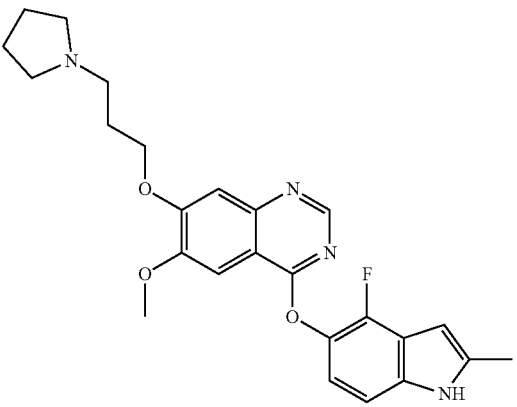 [SMILES: COc1cc2c(Oc3ccc4[nH]c(C)cc4c3F)ncnc2cc1OCCCN1CCCC1] |
| Masitinib | FUS protein and iPSC cell selective | 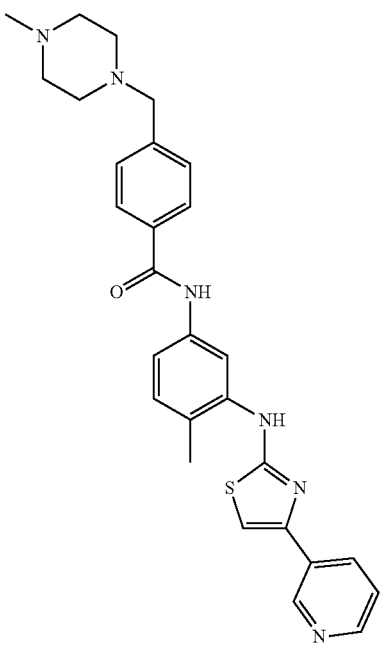 [SMILES: Cc1ccc(NC(=O)c2ccc(CN3CCN(C)CC3)cc2)cc1Nc1nc(-c2cccnc2)cs1] |

What is claimed is:

1. A method of identifying a compound that preferentially affects a level of association of a first macromolecule with one or more target condensates as compared to another macromolecule associated with the one or more target condensates, the method comprising:
(a) contacting a cellular composition with a compound, wherein
(i) the cellular composition comprises the one or more target condensates; and/or
(ii) the one or more target condensates form simultaneously with and/or after contacting the cellular composition with the compound;
(b) measuring, after contacting the cellular composition with the compound, co-localization of the first macromolecule and the other macromolecule via the level of association of the first macromolecule with the one or more target condensates and a level of association of the other macromolecule with the one or more target condensates,
wherein the one or more target condensates are the same class of condensate; and
(c) determining whether the compound preferentially affects the level of association of the first macromolecule with the one or more target condensates,
wherein the determining is by comparing the level of association of the first macromolecule as compared to a reference level for the first macromolecule and the level of association of the other macromolecule as compared to a reference level for the other macromolecule,
wherein the compound preferentially affects the level of association of the first macromolecule with the one or more target condensates when the compound alters the level of the first macromolecule as compared to all the reference level for the first macromolecule more than the compound alters the level of the other macromolecule as compared to the reference level for the other macromolecule, and
wherein the reference level for the first macromolecule is the level of association of the first macromolecule with the one or more target condensates in the absence of the compound, and the reference level for the other macromolecule is the level of association of the other macromolecule with the one or more target condensates in the absence of the compound.

2. The method of claim 1, wherein the one or more target condensates are in the same cell type.

3. The method of claim 1, further comprising measuring the reference level for the first macromolecule.

4. The method of claim 1, further comprising measuring the reference level for the other macromolecule.

5. The method of claim 1, wherein the compound preferentially increases the level of association of the first macromolecule with the one or more target condensates if the compound increases the level of association of the first macromolecule as compared to the reference level for the first macromolecule more than the compound increases the level of association of the other macromolecule as compared to the reference level for the other macromolecule.

6. The method of claim 5, wherein the compound results in the first macromolecule associating with the one or more target condensates.

7. The method of claim 1, wherein the compound preferentially decreases the level of association of the first macromolecule with the one or more target condensates if the compound decreases the level of association of the first macromolecule as compared to the reference level for the first macromolecule more than the compound decreases the level of association of the other macromolecule as compared to the reference level for the other macromolecule.

8. The method of claim 7, wherein the compound results in the first macromolecule not associating with the one or more target condensates.

9. The method of claim 1, wherein the compound alters the level of association of the first macromolecule with the one or more target condensates as compared to the reference level for the first macromolecule at least about 0.25 fold.

10. The method of claim 1, further comprising assessing at least one characteristic of the one or more target condensates.

11. The method of claim 10, wherein the characteristic of the one or more target condensates is selected from the group consisting of: size, number, shape, composition, surface area, location, functional activity, stability, liquidity, and solidification.

12. The method of claim 10, wherein the assessing the at least one characteristic of the one or more target condensates is performed using a microscopy technique.

13. The method of claim 1, further comprising causing the formation of the one or more target condensates.

14. The method of claim 1, wherein the first macromolecule and the other macromolecule are each independently selected from the group consisting of: a polypeptide, a DNA, and an RNA.

15. The method of claim 14, wherein the first macromolecule or the other macromolecule is aberrantly present in a disease state.

16. The method of claim 14, wherein the first macromolecule or the other macromolecule comprises a mutation.

17. The method of claim 1, wherein the first macromolecule comprises a first label.

18. The method of claim 17, wherein the other macromolecule comprises a second label.

19. The method of claim 18, wherein the first label and the second label are distinguishable.

20. The method of claim 19, wherein the first macromolecule and the first label are a fusion protein, and the other macromolecule and the second label are a fusion protein.

21. The method of claim 19, further comprising labeling the first macromolecule and the other macromolecule.

22. The method of claim 21, wherein the labeling comprises contacting the first macromolecule with an antibody or antigen-binding fragment thereof comprising the first label, and contacting the other macromolecule with another antibody or antigen-binding fragment thereof comprising the second label.

23. The method of claim 19, wherein the first label and the second label are each independently selected from the group consisting of: a radioactive label, a colorimetric label, and a fluorescent label.

24. The method of claim 1, wherein measuring the co-localization of the first macromolecule and the other macromolecule comprises use of an imaging technique.

25. The method of claim 1, wherein the cellular composition comprises an animal cell.

26. The method of claim 25, wherein the animal cell has one or more features of a neurodegenerative, proliferative, immunological, cardiac, or metabolic disease.

* * * * *